US011389236B2

(12) United States Patent
Melsky et al.

(10) Patent No.: US 11,389,236 B2
(45) Date of Patent: Jul. 19, 2022

(54) ABLATION SYSTEM WITH AUTOMATED ABLATION ENERGY ELEMENT

(71) Applicant: CardioFocus, Inc., Marlborough, MA (US)

(72) Inventors: Gerald Melsky, Lexington, MA (US); Brian Estabrook, Foxboro, MA (US); Lincoln Baxter, Centerville, MA (US); Sergei Babko-Malyi, Winchester, MA (US); Ronald Green, Bethel, CT (US); Paul DiCesare, Marlborough, MA (US)

(73) Assignee: CARDIOFOCUS, INC., Marlborough, MA (US)

( * ) Notice: Subject to any disclaimer, the term of this patent is extended or adjusted under 35 U.S.C. 154(b) by 351 days.

(21) Appl. No.: 16/248,545

(22) Filed: Jan. 15, 2019

(65) Prior Publication Data

US 2019/0216540 A1    Jul. 18, 2019

Related U.S. Application Data

(60) Provisional application No. 62/691,864, filed on Jun. 29, 2018, provisional application No. 62/617,483, filed on Jan. 15, 2018.

(51) Int. Cl.
*A61B 18/18* (2006.01)
*A61B 18/24* (2006.01)
(Continued)

(52) U.S. Cl.
CPC ...... *A61B 18/18* (2013.01); *A61B 17/320068* (2013.01); *A61B 18/1815* (2013.01);
(Continued)

(58) Field of Classification Search
None
See application file for complete search history.

(56) References Cited

U.S. PATENT DOCUMENTS 4,445,892 A    2/1984   Hussein et al.
4,718,417 A    1/1988   Kittrell et al.
(Continued)

FOREIGN PATENT DOCUMENTS

AU    741167      11/2001
EP    0292695     11/1988
(Continued)

OTHER PUBLICATIONS

Tanaka, Kazushi et al., "A New Radiofrequency Thermal Balloon Catheter for Pulmonary Vein Isolation", Journal of the American College of Cardiology, vol. 38, No. 7, Aug. 28, 2001.

*Primary Examiner* — Michael W Kahelin
*Assistant Examiner* — Elizabeth K So
(74) *Attorney, Agent, or Firm* — Leason Ellis LLP

(57) ABSTRACT

An ablation instrument (e.g., an ablation balloon catheter system) includes an elongate catheter having a housing with a window formed therein. An energy emitter is coupled to the elongate catheter and is configured to deliver ablative energy. A controller is received within the window and is coupled to the energy emitter such that axial movement of the controller within the window is translated to axial movement of the energy emitter and rotation of the controller within the window is translated into rotation of the energy emitter. The instrument includes a motor that is at least partially disposed within the housing of the catheter; a first gear that is operatively connected to and driven by the motor; and a second gear that is coupled to the energy emitter and is driven by the first gear to cause rotation of the energy emitter, while allowing the energy emitter to move axially.

19 Claims, 43 Drawing Sheets

(51) Int. Cl.

| | | |
|---|---|---|
| *A61B 17/32* | (2006.01) | |
| *A61B 18/00* | (2006.01) | |
| *A61B 90/00* | (2016.01) | |
| *A61B 34/10* | (2016.01) | |
| *A61B 90/30* | (2016.01) | |
| *A61B 18/20* | (2006.01) | |
| *A61B 17/22* | (2006.01) | |
| *A61B 17/00* | (2006.01) | |
| *A61B 18/22* | (2006.01) | |

(52) U.S. Cl.
CPC ........ *A61B 18/24* (2013.01); *A61B 17/22012* (2013.01); *A61B 34/10* (2016.02); *A61B 90/30* (2016.02); *A61B 90/361* (2016.02); *A61B 90/37* (2016.02); *A61B 2017/00017* (2013.01); *A61B 2017/00128* (2013.01); *A61B 2017/00247* (2013.01); *A61B 2017/22069* (2013.01); *A61B 2017/320069* (2017.08); *A61B 2017/320098* (2017.08); *A61B 2018/0066* (2013.01); *A61B 2018/00196* (2013.01); *A61B 2018/00208* (2013.01); *A61B 2018/00232* (2013.01); *A61B 2018/00351* (2013.01); *A61B 2018/00577* (2013.01); *A61B 2018/00684* (2013.01); *A61B 2018/00702* (2013.01); *A61B 2018/00761* (2013.01); *A61B 2018/00785* (2013.01); *A61B 2018/00839* (2013.01); *A61B 2018/00898* (2013.01); *A61B 2018/00904* (2013.01); *A61B 2018/00982* (2013.01); *A61B 2018/1823* (2013.01); *A61B 2018/1861* (2013.01); *A61B 2018/2025* (2013.01); *A61B 2018/20357* (2017.05); *A61B 2018/20361* (2017.05); *A61B 2018/20553* (2017.05); *A61B 2018/2272* (2013.01); *A61B 2018/2277* (2013.01); *A61B 2034/107* (2016.02); *A61B 2090/306* (2016.02); *A61B 2090/3614* (2016.02)

(56) References Cited

U.S. PATENT DOCUMENTS

| | | |
|---|---|---|
| 4,862,886 A | 9/1989 | Clarke et al. |
| 4,878,725 A | 11/1989 | Hessel et al. |
| 4,913,142 A | 4/1990 | Kittrell et al. |
| 4,961,738 A | 10/1990 | Mackin |
| 5,030,201 A | 7/1991 | Palestrant |
| 5,053,033 A | 10/1991 | Clarke |
| 5,078,681 A | 1/1992 | Kawashima et al. |
| 5,109,859 A | 5/1992 | Jenkins |
| 5,125,925 A | 6/1992 | Lundahl |
| 5,133,709 A | 7/1992 | Prince |
| 5,188,632 A | 2/1993 | Goldenberg |
| 5,188,634 A | 2/1993 | Hussein et al. |
| RE34,544 E | 2/1994 | Spears |
| 5,318,024 A | 6/1994 | Kittrell et al. |
| 5,395,362 A | 3/1995 | Sacharoff et al. |
| 5,409,483 A | 4/1995 | Campbell et al. |
| 5,417,653 A | 5/1995 | Sahota et al. |
| 5,496,305 A | 3/1996 | Kittrell et al. |
| 5,575,766 A | 11/1996 | Swartz et al. |
| 5,632,767 A | 5/1997 | Sinofsky |
| 5,643,253 A | 7/1997 | Baxter et al. |
| 5,680,860 A | 10/1997 | Imran |
| 5,693,043 A | 12/1997 | Kittrell et al. |
| 5,722,401 A | 3/1998 | Pietroski et al. |
| 5,725,522 A | 3/1998 | Sinofsky |
| 5,769,843 A | 6/1998 | Abela et al. |
| 5,772,590 A | 6/1998 | Webster, Jr. |
| 5,773,835 A | 6/1998 | Sinofsky |
| 5,782,239 A | 7/1998 | Webster, Jr. |
| 5,782,899 A | 7/1998 | Imran |
| 5,800,482 A | 9/1998 | Pomeranz et al. |
| 5,807,395 A | 9/1998 | Mulier et al. |
| 5,833,682 A | 11/1998 | Amplatz et al. |
| 5,843,073 A | 12/1998 | Sinofsky |
| 5,846,223 A | 12/1998 | Swartz et al. |
| 5,860,974 A | 1/1999 | Abele |
| 5,891,133 A | 4/1999 | Murphy-Chutorian |
| 5,891,134 A | 4/1999 | Goble et al. |
| 5,904,651 A | 5/1999 | Swanson et al. |
| 5,908,415 A | 6/1999 | Sinofsky |
| 5,908,448 A | 6/1999 | Roberts et al. |
| 5,967,984 A | 10/1999 | Chu et al. |
| 6,004,269 A | 12/1999 | Crowley et al. |
| 6,012,457 A | 1/2000 | Lesh |
| 6,024,740 A | 2/2000 | Lesh et al. |
| 6,056,744 A | 5/2000 | Edwards |
| 6,071,281 A | 6/2000 | Burnside et al. |
| 6,086,581 A | 7/2000 | Reynolds et al. |
| 6,102,905 A | 8/2000 | Baxter et al. |
| 6,117,101 A | 9/2000 | Diederich et al. |
| 6,120,496 A | 9/2000 | Whayne et al. |
| 6,159,203 A | 12/2000 | Sinofsky |
| 6,164,283 A | 12/2000 | Lesh |
| 6,179,835 B1 | 1/2001 | Panescu et al. |
| 6,245,064 B1 | 6/2001 | Lesh et al. |
| 6,251,109 B1 | 6/2001 | Hassett et al. |
| 6,254,599 B1 | 7/2001 | Lesh et al. |
| 6,270,492 B1 | 8/2001 | Sinofsky |
| 6,305,378 B1 | 10/2001 | Lesh |
| 6,314,962 B1 | 11/2001 | Vaska et al. |
| 6,325,797 B1 | 12/2001 | Stewart et al. |
| 6,375,654 B1 | 4/2002 | Mcintyre |
| 6,383,151 B1 | 5/2002 | Diederich et al. |
| 6,416,511 B1 | 7/2002 | Lesh et al. |
| 6,423,055 B1 | 7/2002 | Farr et al. |
| 6,423,058 B1 | 7/2002 | Edwards et al. |
| 6,471,697 B1 | 10/2002 | Lesh |
| 6,500,174 B1 | 12/2002 | Maguire et al. |
| 6,502,576 B1 | 1/2003 | Lesh |
| 6,514,249 B1 | 2/2003 | Maguire et al. |
| 6,547,780 B1 | 4/2003 | Sinofsky |
| 6,558,375 B1 | 5/2003 | Sinofsky et al. |
| 6,572,609 B1 | 6/2003 | Farr et al. |
| 6,579,285 B2 | 6/2003 | Sinofsky |
| 6,605,055 B1 | 8/2003 | Sinofsky |
| 6,605,084 B2 | 8/2003 | Acker et al. |
| 6,626,900 B1 | 9/2003 | Sinofsky et al. |
| 6,635,054 B2 | 10/2003 | Fjield et al. |
| 6,652,515 B1 | 11/2003 | Maguire et al. |
| 6,676,656 B2 | 1/2004 | Sinofsky |
| 6,771,996 B2 | 8/2004 | Bowe et al. |
| 6,796,972 B1 | 9/2004 | Sinofsky et al. |
| 6,932,809 B2 | 8/2005 | Sinofsky |
| 6,942,657 B2 | 9/2005 | Sinofsky et al. |
| 6,953,457 B2 | 10/2005 | Farr et al. |
| 6,964,660 B2 | 11/2005 | Maguire et al. |
| 6,971,394 B2 | 12/2005 | Sliwa, Jr. et al. |
| 6,997,924 B2 | 2/2006 | Schwartz et al. |
| 7,137,395 B2 | 11/2006 | Fried et al. |
| 7,207,984 B2 | 4/2007 | Farr et al. |
| 7,357,796 B2 | 4/2008 | Farr et al. |
| 7,540,846 B2 | 6/2009 | Harhen et al. |
| 7,655,005 B2 | 2/2010 | Bhola |
| 7,935,108 B2 | 5/2011 | Baxter et al. |
| 7,952,718 B2 | 5/2011 | Li et al. |
| 8,025,661 B2 | 9/2011 | Arnold et al. |
| 8,114,073 B2 | 2/2012 | Whayne et al. |
| 8,152,795 B2 | 4/2012 | Farr et al. |
| 8,231,613 B2 | 7/2012 | Baxter et al. |
| 8,241,272 B2 | 8/2012 | Arnold et al. |
| 8,267,932 B2 | 9/2012 | Baxter et al. |
| 8,277,444 B2 | 10/2012 | Arnold et al. |
| 8,366,705 B2 | 2/2013 | Arnold et al. |
| 8,444,639 B2 | 5/2013 | Arnold et al. |
| 8,540,704 B2 | 9/2013 | Melsky et al. |
| 8,617,150 B2 | 12/2013 | Tsoref et al. |
| 8,696,653 B2 | 4/2014 | Melsky et al. |
| 8,702,688 B2 | 4/2014 | Melsky |
| 8,805,466 B2 | 8/2014 | Salahieh et al. |

(56) References Cited

U.S. PATENT DOCUMENTS

| | | |
|---|---|---|
| 8,900,219 B2 | 12/2014 | Sinofsky et al. |
| 9,033,961 B2 | 5/2015 | Melsky et al. |
| 9,421,066 B2 | 8/2016 | Melsky et al. |
| 9,492,231 B2 | 11/2016 | Cisel et al. |
| 9,622,706 B2 | 4/2017 | Dick et al. |
| 10,105,184 B2 | 10/2018 | Beck et al. |
| 10,349,966 B2 | 7/2019 | Thapliyal et al. |
| 10,517,669 B2 | 12/2019 | Peled et al. |
| 2002/0019627 A1 | 2/2002 | Maguire et al. |
| 2002/0029062 A1 | 3/2002 | Satake |
| 2002/0052621 A1 | 5/2002 | Fried et al. |
| 2002/0065512 A1 | 5/2002 | Fjield et al. |
| 2002/0091383 A1 | 7/2002 | Hooven |
| 2002/0107511 A1 | 8/2002 | Collins et al. |
| 2002/0115995 A1 | 8/2002 | Lesh et al. |
| 2003/0050632 A1 | 3/2003 | Fjield et al. |
| 2003/0065307 A1 | 4/2003 | Lesh |
| 2003/0069620 A1 | 4/2003 | Li |
| 2003/0109778 A1 | 6/2003 | Rashidi |
| 2003/0111085 A1 | 6/2003 | Lesh |
| 2003/0120270 A1 | 6/2003 | Acker |
| 2004/0006333 A1 | 1/2004 | Arnold et al. |
| 2004/0059397 A1 | 3/2004 | Sinofsky et al. |
| 2005/0038419 A9 | 2/2005 | Arnold et al. |
| 2005/0065504 A1 | 3/2005 | Melsky et al. |
| 2005/0222558 A1 | 10/2005 | Baxter et al. |
| 2005/0234436 A1 | 10/2005 | Baxter et al. |
| 2005/0234437 A1 | 10/2005 | Baxter et al. |
| 2006/0122584 A1 | 6/2006 | Bommannan et al. |
| 2006/0253113 A1 | 11/2006 | Arnold et al. |
| 2007/0078451 A1 | 4/2007 | Arnold et al. |
| 2008/0015569 A1 | 1/2008 | Saadat et al. |
| 2008/0097476 A1 | 4/2008 | Peh et al. |
| 2008/0300588 A1 | 12/2008 | Groth et al. |
| 2009/0131931 A1 | 5/2009 | Lee et al. |
| 2009/0221996 A1 | 9/2009 | Lesh et al. |
| 2009/0221997 A1 | 9/2009 | Arnold et al. |
| 2009/0275934 A1 | 11/2009 | Baxter et al. |
| 2009/0299354 A1 | 12/2009 | Melsky et al. |
| 2009/0326320 A1 | 12/2009 | Sinofsky et al. |
| 2010/0042084 A1 | 2/2010 | Nogawa |
| 2010/0168624 A1 | 7/2010 | Sliwa |
| 2010/0198065 A1 | 8/2010 | Thapliyal et al. |
| 2010/0317962 A1 | 12/2010 | Jenkins |
| 2011/0082449 A1 | 4/2011 | Melsky et al. |
| 2011/0082450 A1 | 4/2011 | Melsky et al. |
| 2011/0082451 A1 | 4/2011 | Melsky |
| 2011/0082452 A1 | 4/2011 | Melsky et al. |
| 2011/0245822 A1 | 10/2011 | Baxter et al. |
| 2011/0245828 A1 | 10/2011 | Baxter et al. |
| 2011/0301508 A1 | 12/2011 | Sethuraman et al. |
| 2012/0157981 A1 | 6/2012 | Evans et al. |
| 2012/0289950 A1 | 11/2012 | Neuberger |
| 2013/0012923 A1 | 1/2013 | Baxter et al. |
| 2013/0035537 A1* | 2/2013 | Wallace ............ A61B 34/30 600/8 |
| 2013/0289358 A1 | 10/2013 | Melsky et al. |
| 2013/0345541 A1 | 12/2013 | Nau, Jr. |
| 2014/0005706 A1 | 1/2014 | Gelfand et al. |
| 2014/0031802 A1 | 1/2014 | Melsky et al. |
| 2014/0081254 A1 | 3/2014 | Rudie |
| 2014/0081302 A1 | 3/2014 | Thapliyal et al. |
| 2014/0276398 A1* | 9/2014 | Goodman ......... A61M 25/0136 604/95.04 |
| 2015/0182275 A1 | 7/2015 | Tsoref et al. |
| 2015/0182284 A1 | 7/2015 | Peled et al. |
| 2015/0257830 A1 | 9/2015 | Tyc et al. |
| 2015/0305604 A1 | 10/2015 | Melsky |
| 2016/0157954 A1 | 6/2016 | Sagon et al. |
| 2017/0189108 A1 | 7/2017 | Melsky et al. |
| 2018/0193078 A1 | 7/2018 | Rajagopalan et al. |
| 2018/0271581 A1 | 9/2018 | Ouyang et al. |

FOREIGN PATENT DOCUMENTS

| | | |
|---|---|---|
| EP | 0439629 | 8/1991 |
| EP | 1 009 303 | 6/2000 |
| EP | 1207788 | 5/2002 |
| EP | 1289439 | 3/2003 |
| EP | 1331893 | 12/2004 |
| EP | 1758518 A2 | 3/2007 |
| GB | 2453601 B | 1/2009 |
| JP | 2001-504363 | 4/2001 |
| JP | 2005237827 A | 9/2005 |
| JP | 2006-516465 | 7/2006 |
| JP | 2009543607 | 12/2009 |
| JP | 2016-502892 | 2/2016 |
| WO | WO 9607451 | 3/1996 |
| WO | WO 9640342 | 12/1996 |
| WO | WO 9737714 | 10/1997 |
| WO | WO 00/67656 | 11/2000 |
| WO | WO 00/67832 | 11/2000 |
| WO | WO 01/03599 A2 | 1/2001 |
| WO | WO 01/64123 | 9/2001 |
| WO | WO 03090835 | 11/2003 |
| WO | WO 2004-110258 | 12/2004 |
| WO | WO 2010/120881 | 10/2010 |
| WO | WO 2010/120883 | 10/2010 |
| WO | WO 2011/041629 | 4/2011 |
| WO | WO 2011/041635 | 4/2011 |
| WO | WO 2011/041638 | 4/2011 |
| WO | WO 2011/044248 | 4/2011 |
| WO | WO 2014/109879 | 7/2014 |
| WO | WO 2015/167929 | 11/2015 |
| WO | WO 2016/089900 | 6/2016 |

\* cited by examiner

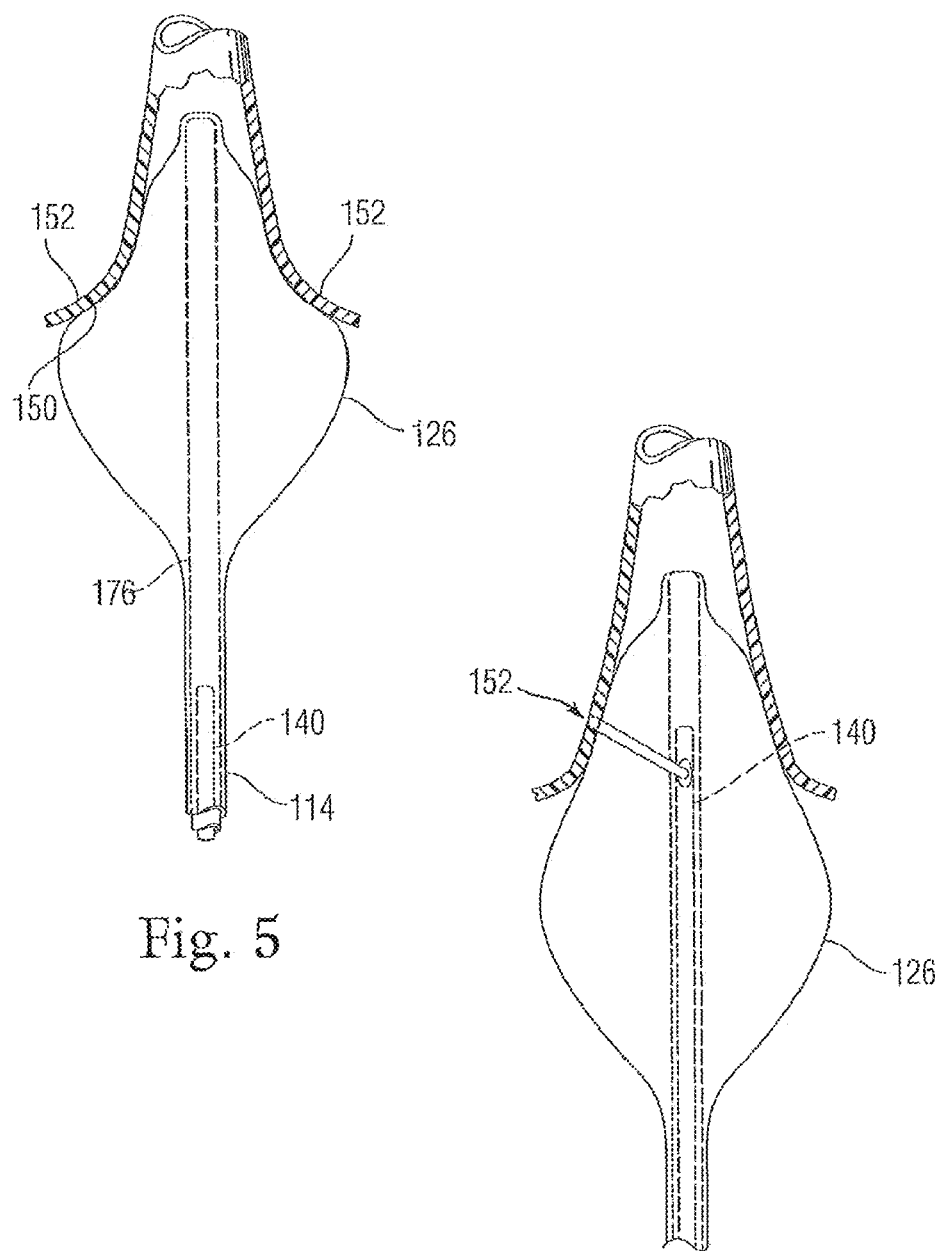

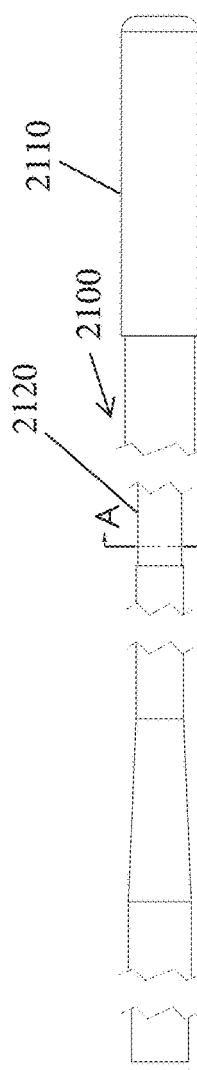
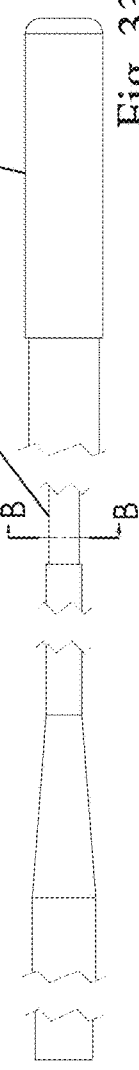
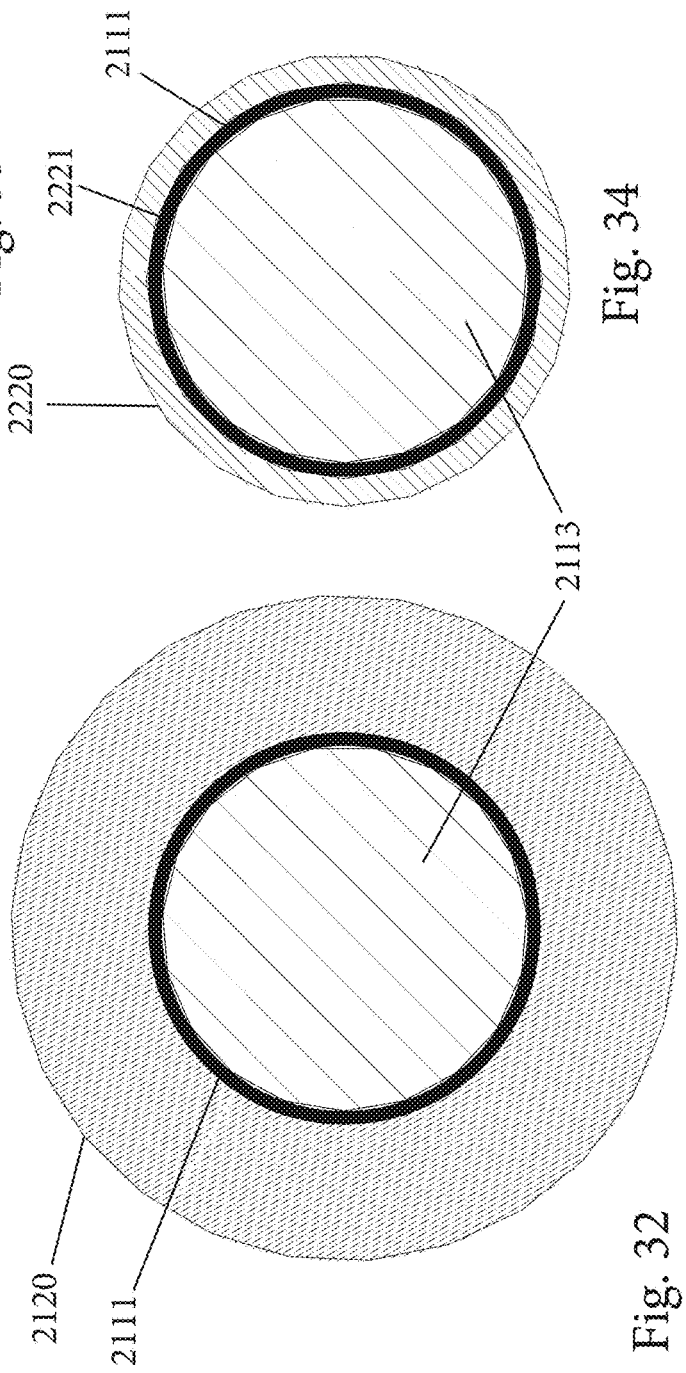

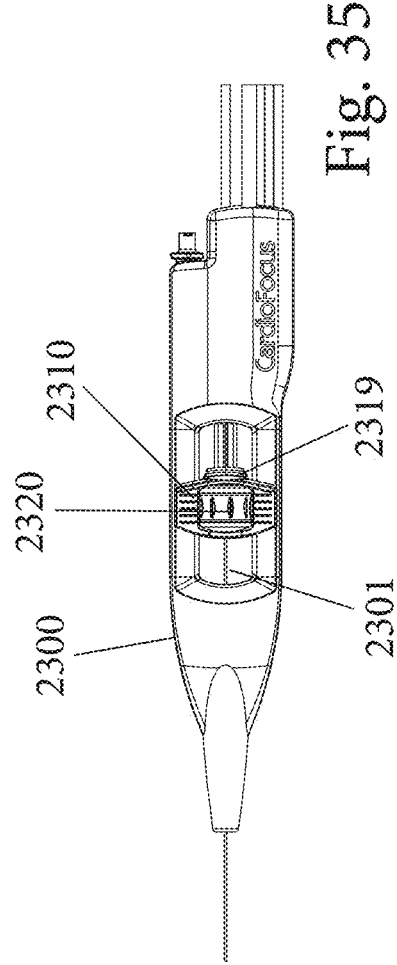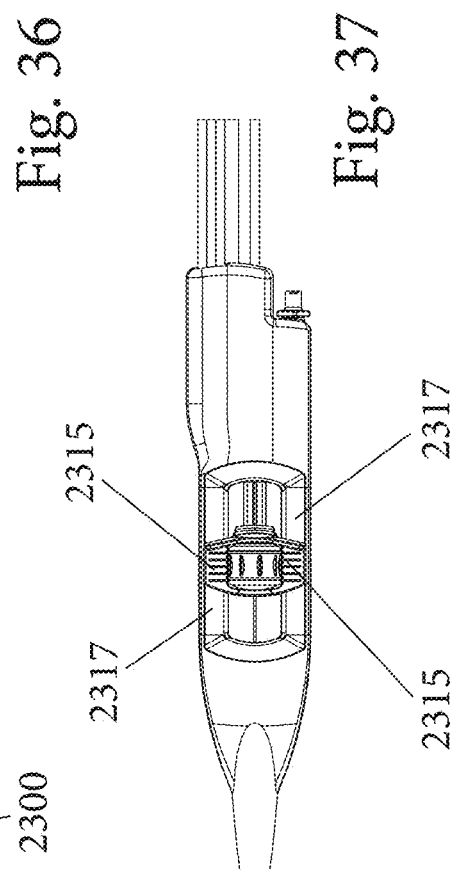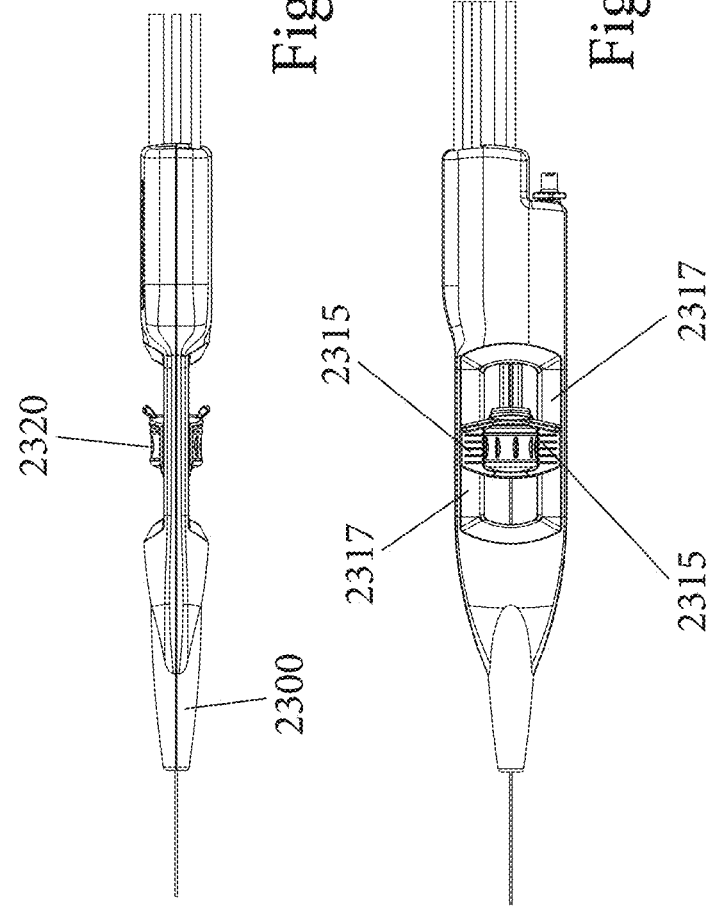

ABLATION SYSTEM WITH AUTOMATED ABLATION ENERGY ELEMENT

CROSS REFERENCE TO RELATED APPLICATIONS

The present invention claims the benefit of and priority to U.S. patent application Ser. No. 62/617,483, filed Jan. 15, 2018, and U.S. patent application Ser. No. 62/691,864, filed Jun. 29, 2018, each of which is hereby incorporated by reference in its entirety.

TECHNICAL FIELD

The present disclosure relates to ablation instruments and methods of use thereof, in particular to ablation catheters and methods for performing ablation procedures utilizing an ablation element (an energy emitter) that can be automated and moves in a sweeping motion and in overlapping increments to provide a customizable scope of coverage of the ablation energy. A geared arrangement with the motor is provided that allows the energy emitter to both rotate and move in an axial direction.

BACKGROUND

Cardiac arrhythmias (e.g., fibrillation) are irregularities in the normal beating pattern of the heart and can manifest themselves in either the atria or the ventricles of the heart. For example, atrial fibrillation is a form of arrhythmia characterized by rapid randomized contractions of atrial myocardium, causing an irregular, often rapid ventricular response. The regular pumping function of the atria is replaced by a disorganized, ineffective quivering as a result of chaotic conduction of electrical signals through the upper chambers of the heart. Atrial fibrillation is often associated with other forms of cardiovascular disease, including congestive heart failure, rheumatic heart disease, coronary artery disease, left ventricular hypertrophy, cardiomyopathy, or hypertension.

It is now understood that recurrent atrial fibrillation (paroxysmal and persistent) is triggered by rapidly firing tissue, (called "ectopic foci"), that are principally located in one or more of the four pulmonary veins, which attach to the rear of the left atrium. It has been found that atrial fibrillation may be prevented by electrically isolating the pulmonary veins from the rest of the left atrium.

Various techniques have been employed for pulmonary vein isolation. A common purpose of each of these techniques is to replace cardiac muscle cells with scar tissue, which scar tissue cannot conduct normal electrical activity within the heart.

In one known approach, circumferential ablation of tissue surrounding the junction of the pulmonary veins and the left atrium has been practiced to treat atrial fibrillation. By ablating the heart tissue at this location transmurally and circumferentially, electrical conductivity between the pulmonary veins and the remainder of the left atrium can be blocked as a result of creating this scar or durable barrier, preventing the initiation of the fibrillatory process.

Several types of ablation devices have recently been proposed for creating lesions to treat cardiac arrhythmias. Many of the recently proposed ablation instruments are percutaneous devices that are designed to create individual lesions from within the heart. Such devices are positioned in the heart by catheterization of the patient, e.g., by passing the ablation instrument into the heart via a blood vessel, such as the femoral vein and then gaining transseptal access to the left atrium.

Typically, percutaneous devices are positioned with the assistance of a guide catheter, which is first advanced into the left side of the heart through a hole made in the intraatrial septum. In one increasingly common approach, a guide catheter or similar guide device is advanced through the vasculature and into the left atrium of the heart. A catheter instrument with an expandable element is then advanced through the guide catheter and into each one of the ostia of pulmonary veins where the expandable element (e.g., a balloon) is inflated. The balloon includes a moveable ablation element, e.g., an energy emitting device, such as a laser, disposed in the inner surface of the balloon, which allows the physician to sequentially position and control the application of energy in the area of the junction between the vein ostium and the left atrium to create a durable barrier which is the objective of the ablation procedure.

A number of ablation systems operate by emitting ablation energy, such as a laser beam, that has a circumferential shape or has a shape that is less than a complete circumference (i.e., arc shaped). While these systems are effective, in the case of devices which emit arc-shaped ablation energy, the user may have to incrementally move the ablation element using a significant number of steps to complete the lesion. This process can be time consuming since the ablation element may be configured to only emit a small arc of energy (e.g., subtending at an angle from about 5 to 30 degrees relative to the energy emitter in one embodiment).

Thus, there remains a need in the art for systems and methods configured to accurately and immediately confirm whether the pulmonary vein isolation procedure was successful, thereby allowing the user (electrophysiologist, more specifically an electrophysiologist or interventional cardiologist) to take corrective action in real time to ensure a complete circumferential barrier has been durably formed. There also remains a need in the art for systems and methods configured to more efficiently complete the lesion.

SUMMARY

An ablation instrument (e.g., ablation balloon catheter system) includes an elongate catheter having a housing with a window formed therein. An energy emitter is coupled to the elongate catheter and is configured to deliver ablative energy. A controller is received within the window and is coupled to the energy emitter such that axial movement of the controller within the window is translated to axial movement of the energy emitter and rotation of the controller within the window is translated into rotation of the energy emitter. The instrument includes a motor that is at least partially disposed within the housing of the catheter; a first gear that is operatively connected to and driven by the motor; and a second gear that is coupled to the energy emitter and is driven by the first gear to cause rotation of the energy emitter, while allowing the energy emitter to move axially.

These and other aspects, features and benefits of the invention can be further appreciated from the accompanying drawings, which illustrate certain embodiments of the invention together with the detailed description thereof.

BRIEF DESCRIPTION OF THE DRAWINGS

The objects and features of the invention may be understood with reference to the following detailed description of an illustrative embodiment of the present invention taken together in conjunction with the accompanying drawings in which:

FIG. 5 is a schematic view of the cardiac ablation instrument of FIG. 2 shown in a treatment position within the ostium for treatment of the pulmonary vein;

FIG. 6 is a schematic view of the cardiac ablation instrument of FIG. 2 with its compliant balloon inflated and its ablation element deployed at one of a plurality of locations;

FIG. 31 is a partial side elevation view of a distal portion of a lesion generator (ablation element) according to one embodiment;

FIG. 32 is a cross-sectional view taken along the line A-A of FIG. 31;

FIG. 33 is a partial side elevation view of a distal portion of a lesion generator according to yet another embodiment;

FIG. 34 is a cross-sectional view taken along the line B-B of FIG. 33;

FIG. 35 is a first side elevation view of a portion of a catheter handle that includes a movable rotatable knob and a slider part;

FIG. 36 is a top plan view thereof;

FIG. 37 is a second side elevation view thereof;

DETAILED DESCRIPTION OF CERTAIN EMBODIMENTS OF THE INVENTION

The present invention will now be described more fully with reference to the accompanying drawings, in which illustrated embodiments of the present invention are shown. The present invention is not limited in any way to any of the illustrated embodiments.

As described in detail below, the present invention relates to ablation equipment/ablation system, such as an ablation catheter, that is configured to have a visualization feature (functionality) that allows the user to determine, in real-time, whether a complete lesion has been formed by monitoring the state of the electrical activity at the target site and more specifically, by monitoring a visual change in a pool of blood that is located distal to the target site. In one embodiment, the visual change in the pool of blood (e.g., blood in the pulmonary vein) is represented by a change in the visible pattern of perturbation of the blood pool since at an initial pre-procedure point (i.e., a baseline), vigorous activation is visible in the blood pool (i.e., a high degree of perturbation of the blood pool) and as the ablation procedure progresses, incremental lessening in the vigorous nature of blood pool movement becomes visible (due to the progressive formation of a circumferential lesion and a concomitant reduction in electrical activity distal to the target site).

A display, such as a computer monitor, presents images in real time that allow the user to determine whether the formed lesion has had the desired effect on the electrical activity at the target site (i.e., electrical isolation). In other words, the system of the present invention is configured to provide the user with real-time visualization information that allows the user to determine whether a complete lesion has been formed at the target site. In addition, a visualization module can be provided along with software that allows a comparison between two or more images of the target site.

Since the sufficiency of the lesion is immediately and readily determinable, the user (electrophysiologist) can detect whether a complete lesion has been formed and in the event that there are any deficiencies in the lesion, such as gaps or breaks in the lesion, the user can take immediate corrective measures.

Figure 1:
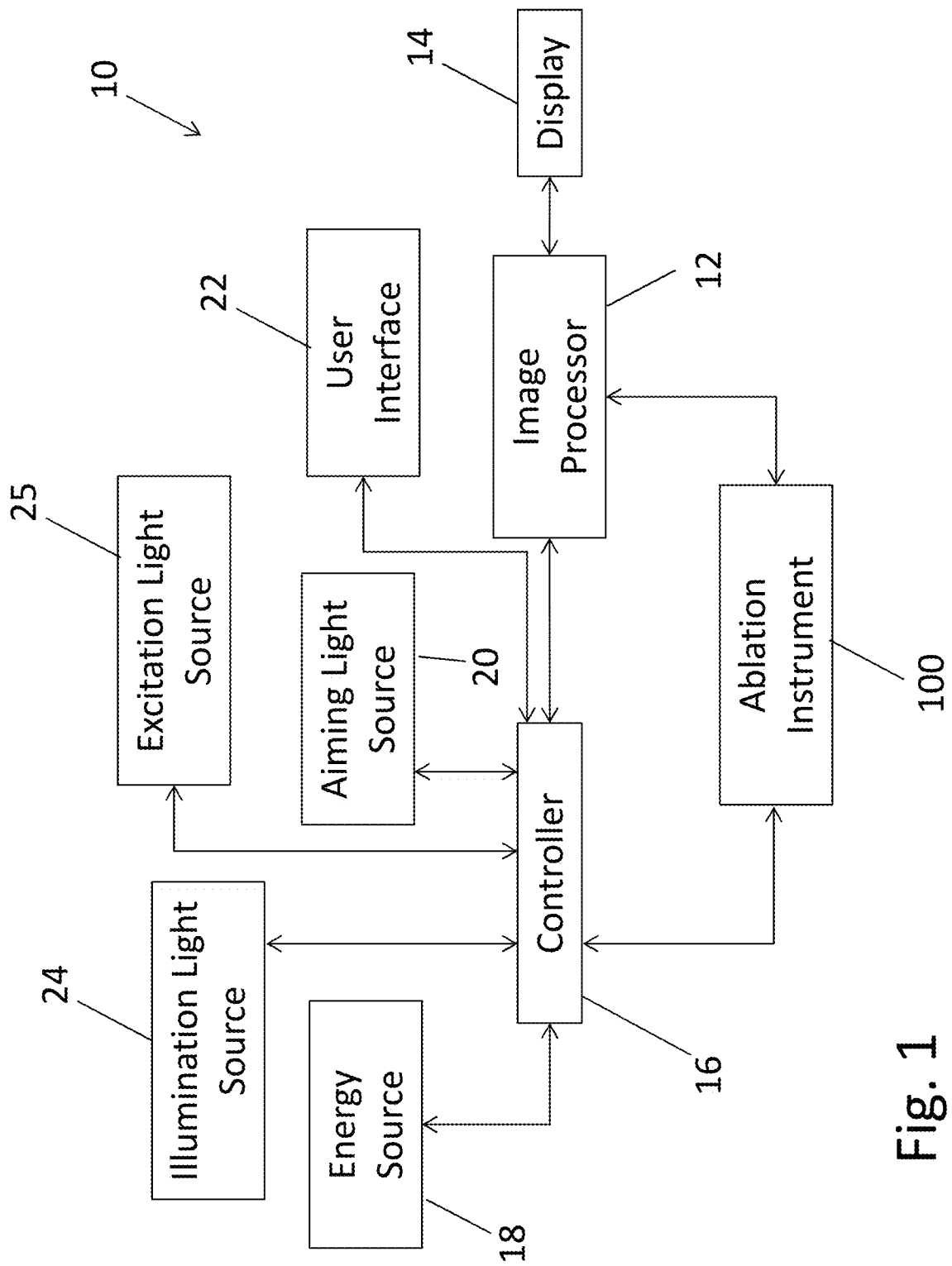
FIG. 1 is a block diagram depicting the components of an endoscope-guided cardiac ablation system according to the invention.

FIG. 1 is a schematic block diagram illustrating an ablation/endoscopic system in accordance with the invention, designated generally by reference numeral 10. Ablation system 10 preferably includes a treatment ablation instrument 100 preferably including an endoscope and ablation device (energy emitter) as discussed below. The treatment ablation instrument 100 can be any number of different ablation instruments that are commercially available including those disclosed by Applicant in previous U.S. patents and patent applications (e.g., U.S. patent application publication Nos. 2009/0326320 and 2011/0082451, each of which is hereby incorporated by reference in its entirety). In general, the ablation instrument 100 is of a type that emits ablation energy sufficient to cause formation of an ablation at a tissue target site.

The ablator system 10 further preferably includes an aiming light source 20 and an illumination light source 24. A processor 12 designed to accept input and output data from the connected instruments, a display 14, and a controller 16 and process that data into visual information.

As will also be appreciated from the below discussion, an endoscope is preferably provided in ablation instrument 100 and has the capability of capturing both live images and recording still images. An illumination light 24 is used to provide operating light to the treatment site. The illumination light is of a frequency that allows the user to differentiate between different tissues present at the operating site. An aiming light source 20 is used to visualize the location where energy will be delivered by the ablation instrument 100 to tissue. It is envisioned that the aiming light 20 will be of a wavelength that can be recorded by an image capture device and visible on a display.

Composite Imaging System

The processor 12 is preferably designed to process live visual data as well as data from the ablation instrument controllers and display. The processor 12 is configured execute a series of software and/or hardware modules configured to interpret, manipulate and record visual information received from the treatment site. The processor 12 is further configured to manipulate and provide illustrative and graphical overlays and composite or hybrid visual data to the display device.

As seen in FIG. 1, the system 10 further includes the controller 16, an energy source 18, the aiming light source 20 and a user interface 22. Controller 16 is preferably configured to control the output of the energy source 18 and the illumination and excitation sources 24 and 25 of an energy transmitter, as well as being configured to determine the distance and movement of an energy transmitter relative to tissue at an ablation treatment site (as discussed further below). As will also be appreciated from the below discussion, an endoscope is preferably supported by the ablation instrument 100 and captures images that can be processed by the processor 12 to determine whether sufficient ablative energy deliveries have been directed to a specific area of a treatment site. Data obtained from the endoscope includes real-time video or still images of the treatment site as seen from the ablation instrument. As discussed herein, these images/videos can be stored in memory for later use.

The aiming light source 20 is used to visualize the treatment site location 120 where energy will be delivered by the ablation instrument 100 to tissue 130. Preferably, the aiming light source 20 outputs light in a visible region of the electromagnetic spectrum. If a suitable ablation path is seen by the user, the controller 16 transmits radiant energy, via energy source 18, from the ablation instrument 100 to a target tissue site 152 (FIG. 8) to effect ablation by lesions. It is to be appreciated that the term "radiant energy" as used herein is intended to encompass energy sources that do not rely primarily on conductive or convective heat transfer. Such sources include, but are not limited to, acoustic, laser and electromagnetic radiation sources and, more specifically, include microwave, x-ray, gamma-ray, ultrasonic and radiant light sources. Additionally, the term "light" as used herein is intended to encompass electromagnetic radiation including, but not limited to, visible light, infrared and ultraviolet radiation.

The illumination light source 24 is a light source used to provide proper illumination to the treatment site. The illuminate is configured so that natural biological tones and hues can be easily identifiable by an operator.

The controller 16 can provide the user with the ability to control the function of the aiming light source, the user input devices, and the ablation instrument. The controller 16 serves as the primary control interface for the ablation system. Through the controller 16, the user can turn on and off both the aiming and illumination lights 20, 24. Furthermore the controller 16 possesses the ability to change the illumination and aiming light intensity. The ability to switch user interfaces or display devices is also envisioned. Additionally, the controller 16 gives access to the ablation instrument 100, including control over the intensity of the discharge, duration and location of ablative energy discharges. The controller 16 can further provide a safety shutoff to the system in the event that a clear transmission pathway between the radiant energy source and the target tissue is lost during energy delivery (e.g., see commonly owned U.S. patent application Ser. No. 12/896,010, filed Oct. 1, 2010, which is hereby incorporated by reference in its entirety).

The controller can be a separate microprocessor based control interface hardware or it can be a portion of a configured as a module operating through a processor based computer system configured to accept and control inputs from various physical devices.

Figure 3:
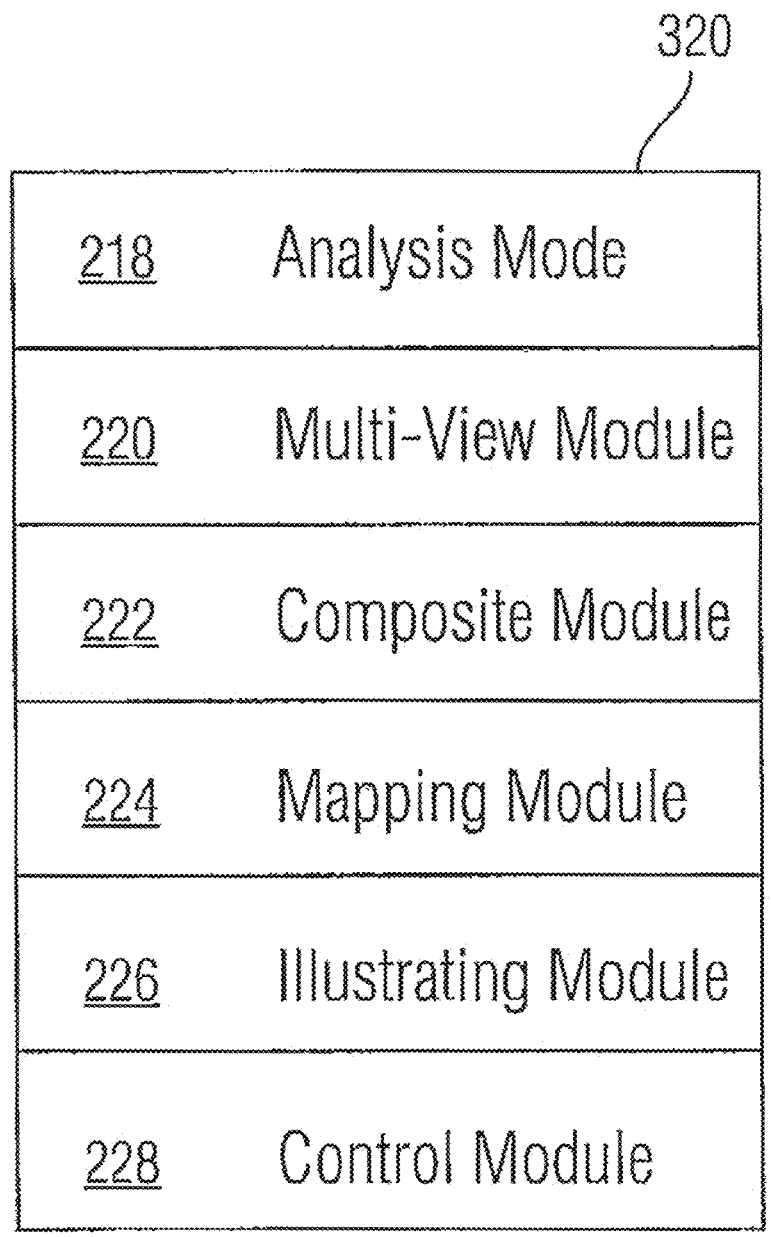
FIG. 3 is a block diagram of the processor modules used in the cardiac ablation instrument.

As shown in FIG. 3, a set of modules cooperate with one another to provide the information presented through the interface 22 of the system of FIG. 1. Thus, for example, there can be an analysis module 218, a multiple view module 220, a composite module 222, a mapping module 224, an illustrating module 226, and a control interface module 228. Each of these modules can comprise hardware, code executing in a processor, or both, that configures a machine, such as a workstation, to implement the functionality described herein.

With further reference to FIG. 3, the analysis module 218 includes instructions for analyzing a lesion and determining if it is sufficient for the desired treatment. The analysis module 218 can be configured to inspect the image data captured by the image capture device (e.g., an endoscope) and determine whether a lesion of sufficient dimensions and quality has been formed based in part on an analysis of pre-procedure motion (electrical activity) at the target site and post-procedure motion (electrical activity). The analysis module 218 can be implemented as discrete sub-modules to provide functions such as receiving data on the duration and intensity of an ablative emission. An additional submodule is capable of evaluating the duration of the energy emission and comparing it to a look up table of sufficient duration and intensity values suitable to form a proper lesion.

The multiple view module 220 includes instructions for configuring the processor 12 to provide multiple images to the display. The multiple view module configures the display to depict at least two image depiction areas. In a first image depiction area, the live video stream of the treatment site is displayed to the user. In a second image depiction area, a still image, highlighting the last target of ablative energy is depicted or depicting other information such as a baseline image as described below.

The composite module 222 includes instructions for combining a series of still images and producing a composite image that depicts the target location of the ablative emission in each still image. The compositing module 222 can be implemented as discrete sub-modules to provide functions such as altering the transparency of each still image layer of the composite image so that a time-based map of ablation locations can be produced. Another function implemented by the submodules is construction of a video or slideshow from a sequence of still images. It will be understood that the composite module 222 is optional.

The mapping module 224 includes instructions for overlaying proposed treatment paths on the live image. The mapping module can be configured to show colored markers indicating acceptable levels of ablative energy depositing. For example the mapping module is capable of generating a colored visual marker and superposing it over the live image to indicate areas that have yet to receive levels of ablative energy necessary for treatment. Conversely, the mapping module 224 is also capable of simultaneously generating a red colored (or other color) visual marker and superimposing it over the live image to indicate areas that have received sufficient quantities of ablative energy suitable lesions. The mapping module 224 can be implemented as discrete sub-modules to provide functions such as receiving data on the duration and intensity of an ablative emission and correlating that specific instance to a specific stored image.

In accordance with one aspect of the present invention, the mapping module 224 can be configured to superimpose a live image of the distal blood pool over the pre-procedure image of the distal blood pool to allow a visual comparison therebetween (which is indicative of the sufficiency (degree of completion) of the ablation.

It will also be understood that the mapping module 224 is optional.

Figure 2:
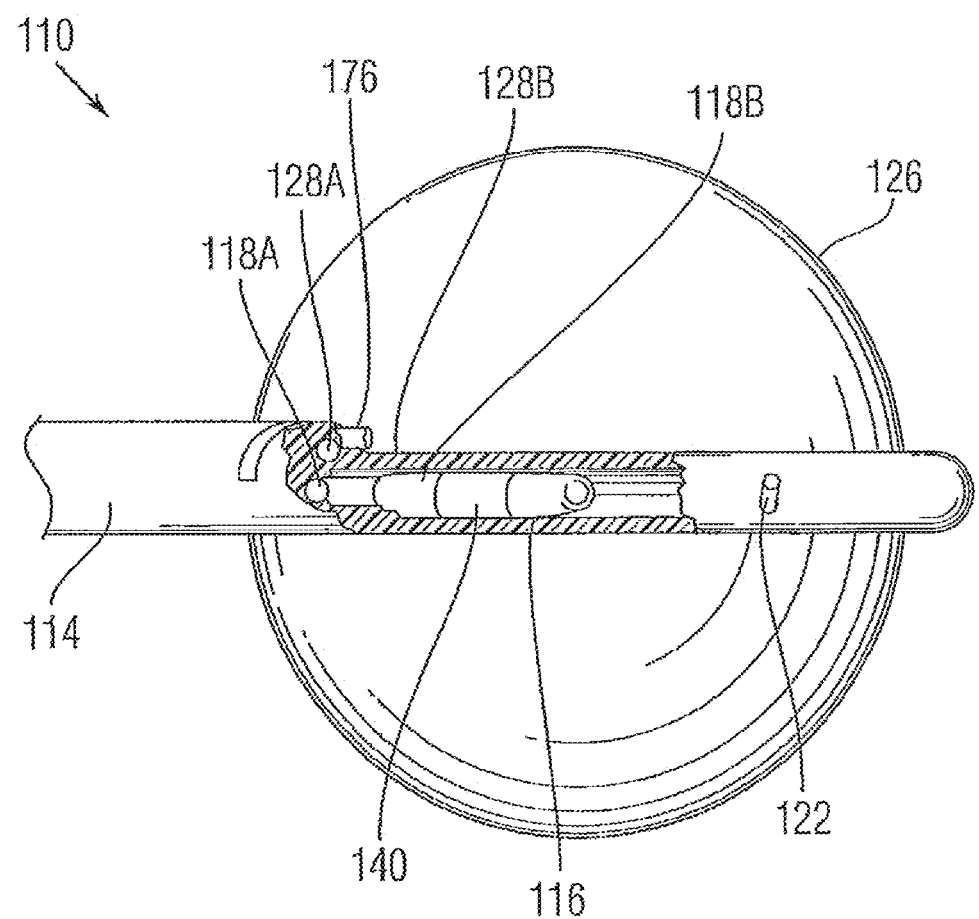
FIG. 2 is a schematic view of the of the cardiac ablation instrument of the cardiac ablation system of FIG. 1.
Figure 8:
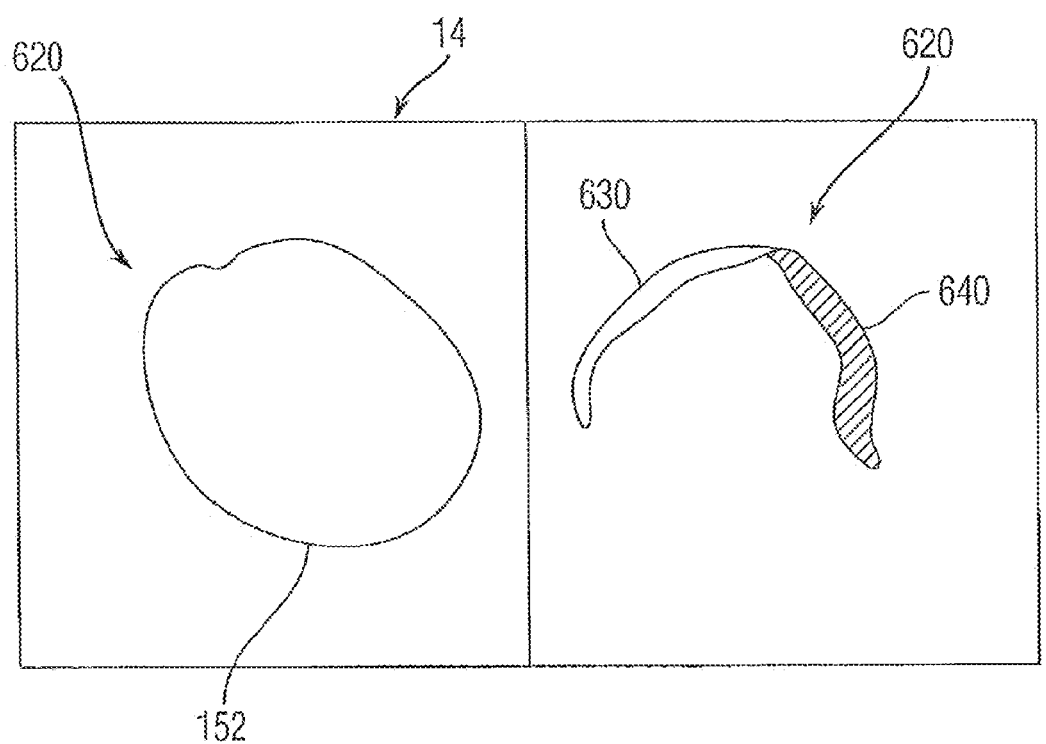
FIG. 8 is a screen shot of the display of FIG. 1 depicting visual warning signals indicative of insufficient lesions.

The illustrating module 226 includes instructions for providing an image to the display, wherein the image is an illustration or graphical representation of the treatment site. The illustrating module 226 is configured to allow annotation of the illustrated image as well as comparison between the live image and the illustrated image. For example, and as shown in FIG. 8, display 14 provides a first screen portion 610 depicting the actual treatment site 152 as viewed from endoscope 176 (FIG. 2). Display 14 can also illustrate a second screen portion 620 illustrating a graphical depiction of the treatment site 152 indicating the actual path of the energy transmitter 140 on the tissue at the treatment site wherein the path consists of a trace indicating the sufficiency of the formed lesions in which a solid trace 630 indicates sufficient lesions and a hashed trace 640 indicates insufficient lesions. The illustrating module 226 is also optional.

In one embodiment, the system can be configured so as to at least contain the analysis module 218, the multiple view module 220, the illustrating module 226, and the control interface module 228.

The control module 220 includes instruction for orientating and accessing the functions of each of the other modules, as well as communicating with the controller and inputting information or manipulating the parameters of the data being displayed during operation. The manipulation and controlling functions can be implemented as discrete sub-modules with instructions for selecting operation modes, control interfaces, display orientation, recording modes, storage device location and data entry.

Figure 4:
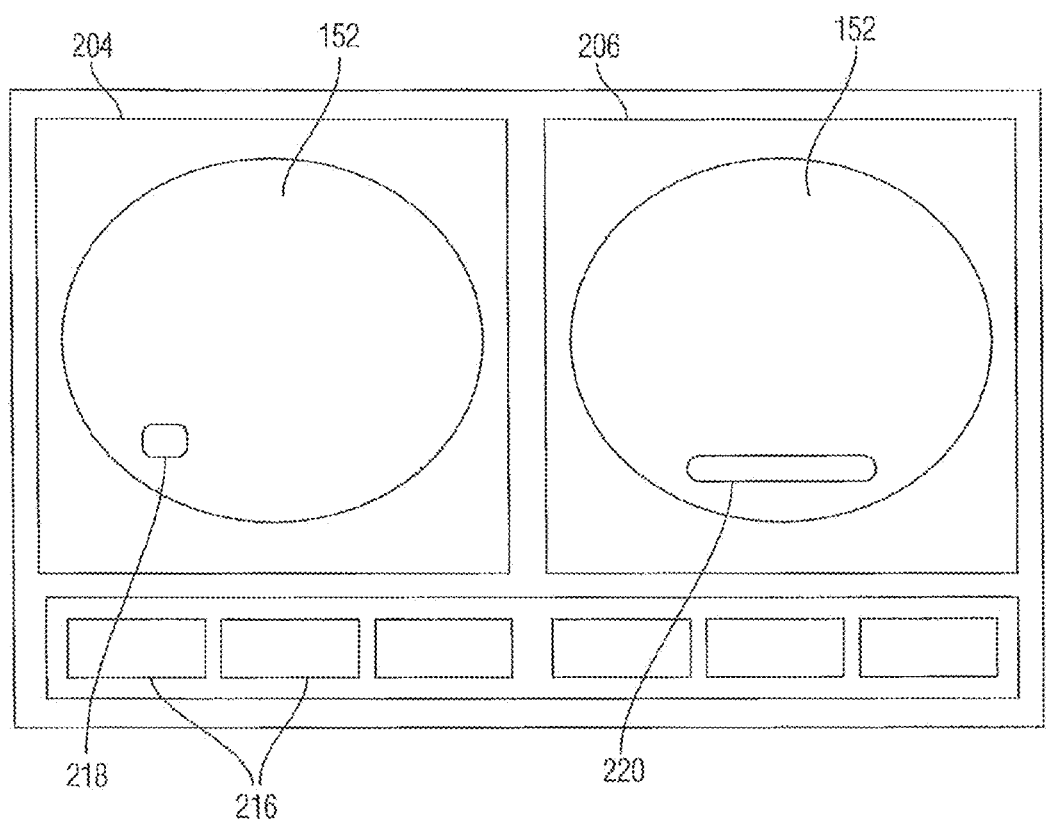
FIG. 4 illustrates a user interface in the form of a split-screen arrangement for displaying information.

The user refers to the live video feed from the image capture device to determine where to direct a radiant energy transmission. Upon first use of the device, a live video image and a still image of the treatment site are depicted on the display. As seen in FIG. 4, the processor 12 outputs to the display 14 at least two separately defined image depiction areas 204, 206. One image depiction area 204 is reserved for displaying live video transmitted from the treatment site 152. At least one other image depiction area 206 is used to depict an image or a composite image comprised of several still images representing specific moments in time during the treatment (an intracardiac procedure).

The live video shown to the user will allow the user to see the reflection of the aiming light 218 and hence direct ablative energy. It is envisioned that the first still image 210 depicted will be a still image captured at a point in time prior to the initiation of the first radiant energy emission. For instance, at a point in time prior to the emission of radiant energy, the image capture device records an image 210 of the treatment site 152 that depicts the treatment site 152 without the aiming light. By taking a still image 210 of the site, the user can record a baseline image of the treatment site before any treatment has been commenced. Furthermore, through the functions of the illustrative module, an illustration of the untouched 152 can be generated. During emission of radiant energy a still image 210 is taken of the treatment site 152. The characteristics of the ablative event (e.g. information regarding the duration and intensity of the radiance of the energy emission) are stored and associated with the image depicting that specific emission. In addition, the reflection of the aiming light will be visible in the still image, providing a location indicator as to where the energy was directed. A series of these still images can be combined by using the composite module. By modifying the opacity of each image, the reflected light of the aiming light for each ablative event will be visible in the composite image. In this way, a complete record 220 of where energy was directed will become available. Furthermore, because the composite image is composed a series of individual images representing a specific period of time during the procedure, a time-based map of the entire operation can also be produced in real time or for subsequent review.

Also visible in FIG. 4 are control interfaces 216 for accessing the control module 228. The control interfaces allow the user to select image style and opacity as well and initiating the functions of the other modules. Furthermore the functions of the controller 16 are also controllable from the control interface 228.

It is to be appreciated the invention is not to be understood to be limited to the two image depiction areas discussed above with reference to FIG. 3 or 4, but rather may encompass any number of image depiction areas in which the images and representations of the treatment site 152 can be reviewed. With reference to FIG. 8 the images shown by the display 14 can be manipulated by the modules to illustrate the presence of sufficient or insufficient lesion formation. For instance, the display 14 may illustrate the image of the treatment site 152 viewed from the endoscope 176 FIG. 2) wherein varying shades of grey and white depict tissue and lesions and in the event insufficient lesions are determined to be formed, or a red marker can be superimposed on the image of the treatment site 152 at the location where the insufficient lesion was determined. Coincidentally, an audio signal may also be emitted from ablation system 10 causing further warning to the user.

Therefore, if the user is not satisfied with the quality of the lesion produced, or the modules indicate that a sufficient lesion was not produced, the user can promptly redo the treatment of a specific tissue location (spot treatment). Conversely, if the modules indicate that a sufficient lesion was formed, the user can confidently move on to a new tissue location to continue the treatment thus saving time and effort by avoiding the need to more closely examine the tissue location that was just treated. Hence, once the entire treatment is performed, the modules of the system permit the electrophysiologist to view all treatment segments forming the entire ablation arc to see if a continuous, uninterrupted ablation has been formed (or see if the ablation has the intended, desired shape). If there are visible gaps or other imperfections with the formed ablation, the electrophysiologist can move the energy emitter (also referred to herein as an ablation element) 140 to the proper location for retreatment of these areas until the desired ablation is formed. The process can then be repeated to determine and confirm that the gap was eliminated.

As a result, the mapping, analyzing and illustrating functions performed by the ablation system of the present invention overcome the disadvantages associated with prior ablation procedures and results in increased ablation success rates due to a more optimal and more accurate viewing and quality determination of the spot lesions created to form the continuous ablation at the tissue location for the treatment site 152.

With reference now to FIGS. 2 and 5, a description of ablation instrument 100 is provided. FIG. 5 provides a schematic, cross-sectional view of an ablation instrument 100, including an elongated body 114, a central lumen tubing 116 and a compliant balloon 126 inflatable via one or more ports 122 in the central tubing 116. The central tubing 116 can also house an energy emitter 140 that is capable of both axial movement and rotation within a lumen formed in the elongate body 114. Additionally formed in the elongated body 114 (also referred to herein as the catheter body) there can be a plurality of additional lumens, through which certain devices or instruments can be passed. For example, the catheter body 114 also provides lumens 118A and 118B for extraction (or circulation) of an inflation fluid, an endoscope 176 and illumination and excitation fibers 128A and 128B.

It should be understood that the embodiments illustrated in the drawings are only a few of the cardiac ablation instruments that can be utilized in accordance with the present invention. Further descriptions of other embodiments can be found, for example, in commonly owned, U.S. patent application Ser. No. 10/357,156, filed Feb. 3, 2003, U.S. patent application Ser. No. 09/924,393, filed Aug. 7, 2001—each of which is expressly incorporated by reference.

With reference now to FIGS. 5-6, the ablation instrument 100 is preferably designed such that upon disposition within the heart (e.g., proximal to a pulmonary vein), the balloon 126 can be inflated such that a shoulder portion 150 of the balloon 126 will be urged into close proximity with a target region 152 of cardiac tissue. As shown in FIG. 4, the energy emitter (or "lesion generator") 140 can be positioned to deliver ablative energy to the target region 152 to form a continuous lesion. The term "continuous" in the context of a lesion is intended to mean a lesion that substantially blocks electrical conduction between tissue segments on opposite sides of the lesion.

The radiant energy emitter 140 is shown in FIG. 2 disposed within the balloon 126 located remotely from the target tissue (e.g., within a central lumen 116 of the catheter body 114 or otherwise disposed within the balloon). In one illustrated embodiment, the radiant energy transmitter (ablation element) 140 includes at least one optical fiber coupled to a distal light projecting, optical element, which cooperate to project a spot of ablative light energy through the instrument 100 to the target site 152 (in FIG. 6). The catheter body 114, projection balloon 126 and inflation/ablation fluids are all preferably substantially transparent to the radiant energy at the selected wavelength of the energy source to provide a low-loss transmission pathway from the radiant energy transmitter 140 to the target site 152. It should be understood that the term "balloon" encompasses deformable hollow shapes which can be inflated into various configurations including spherical, obloid, tear drop, etc., shapes dependent upon the requirements of the body cavity. Such balloon elements can be elastic or simply capable of unfolding or unwrapping into an expanded state. The balloon can further encompass multiple chamber configurations.

Also disposed within the instrument 100 is a visualization device, such as a reflectance sensor, preferably an endoscope 176 capable of capturing an image of the target site 152 and/or the instrument position. The endoscope 176 is typically an optical fiber bundle with a lens or other optical coupler at its distal end to receive light. The reflectance sensor/endoscope can also include an illumination source, such one or more optical fibers coupled to a light source or sources. Alternatively illumination and excitation light may be delivered though separate optical fibers as indicated by 128A in FIG. 2. Endoscopes are available commercially from various sources. The endoscope can further include an optical head assembly, as detailed in more detail below, to increase the field of view. In one illustrated embodiment, ablation element 140 and endoscope 176 are adapted for independent axial movement within the catheter body 14.

The term "endoscope" as used herein is intended to encompass optical imaging devices, generally, including but not limited to endoscopes, fiberscopes, cardioscopes, angioscopes and other optical fiber-based imaging devices. More generally, "endoscope" encompasses any light-guiding (or waveguide) structure capable of transmitting an "image" of an object to a location for viewing, such as display 14.

Preferably, spot lesions are formed at the target site 152 by applying radiant energy from the energy transmitter 140 to target tissue. The applied radiant energy may be applied in an energy range from about 50 Joules/cm$^2$ to about 1000 Joules/cm$^2$, or preferably from about 75 Joules/cm$^2$ to about 750 Joules/cm$^2$. The power levels applied by the energy emitter can range from about 10 Watts/cm$^2$ to about 150 Watts/cm$^2$ and the duration of energy delivery can range from about 1 second to about 1 minute, preferably from about 5 seconds to about 45 seconds, or more preferably from about 10 to about 30 seconds. For example, for power levels between 10 and 75 Watts/cm$^2$ it can be advantageous to apply the radiant energy for about 30 seconds. Lesser durations, e.g., of 10 to 20 seconds, can be used for power levels of 75 to 150 Watts/cm$^2$. In other words, the greater the power level, the lesser the residence time of the emitter at a specific location to achieve the desired ablation. It is to be understood the above figures are provided as examples and the energy, power and time duration figures set forth above are provided merely as examples and are not to be understood to be limited thereto.

In the illustrated embodiment of the ablation instrument 100 shown in FIGS. 5-6, the energy emitter 140 is a radiant energy emitter including at least one optical fiber coupled to a distal light projecting optical element, which cooperate to project a spot of ablative light energy through the instrument 100 to the target site 152. The optical element can further comprise one or more lens elements and/or refractive elements capable of projecting a spot or arc-shaped beam of radiation. Alternatively, the lesion generator may generate an annulus or partial ring of ablative radiation, as described in more detail in commonly owned U.S. Pat. No. 6,423,055 issued Jul. 22, 2002, herein incorporated by reference for its disclosure related thereto.

Automated Sweeping Motion for the Ablation Element

As described herein, the ablation element 140 not only moves axially within the balloon but also is configured to move in a rotational manner to allow a series of arc shaped energy emissions (which form arc shaped ablation segments) to be pieced together to form the completed lesion. The user may incrementally move, in a manual process, the ablation element 140 using a significant number of steps to complete the lesion when the ablation energy is emitted in an arc shaped pattern (so as to form an arc shaped ablation segment). In order to ensure a full complete lesion, the user typically at least partially overlaps a new arcuate lesion segment with a previously and immediately adjacent formed arcuate lesion segment to ensure completeness in the ablation process (i.e., no gaps in the lesion). However, as mentioned herein, this process can thus be time consuming since the user must carefully rotate the ablation element a selected number of degrees resulting in some overlap between the footprint (area) of the new ablation energy arc and the footprint of the previously formed lesion and then the ablation energy is applied.

The ablation energy is emitted for a predetermined period of time for each arcuate ablation segment that is formed. The amount of time can vary depending on a number of parameters including the size of the arcuate shaped segment being formed (e.g., the number of degrees for the arcuate shaped segment) and the degree of overlap with a previously formed arcuate shaped ablation segment and also can be based on anatomical considerations, such as the target location and the nature of the tissue landscape at the target location. For example, if the formed arcuate shaped segment has a footprint of 30 degrees, then the ablation energy may be emitted for a predetermined time period, such as 30 seconds to ensure proper ablation of the tissue. Typically, the larger the footprint of the ablated segment (i.e., the greater the number of degrees covered by the arcuate shaped ablation segment), the greater the amount of time needed to complete the tissue ablation.

In accordance with the present invention, the system includes optional functionality that allows for the ablation energy to undergo a programmed, controlled sweeping action resulting in an ablation being formed that occupies a greater surface area (larger footprint) than possible using a fixed, static energy emission. As described herein, the user can use a graphical user interface or the like to input the desired controlled parameters which are then executed and the ablation element 140 is moved in a controlled sweeping action over a predetermined number of degrees of travel. As described herein, the overall system has a number of safeguards to ensure proper ablation formation. For example, safety features, such as an emergency shut off, can be provided to allow the user to stop the ablation sweeping action at any time.

The sweeping action described herein that is provided by the automated ablation element of the present invention results in a larger arcuate shaped ablation segment being formed even though the actual ablation element is configured to emit a smaller sized arcuate shaped ablation segment as when the ablation element is held stationary.

Figure 12:
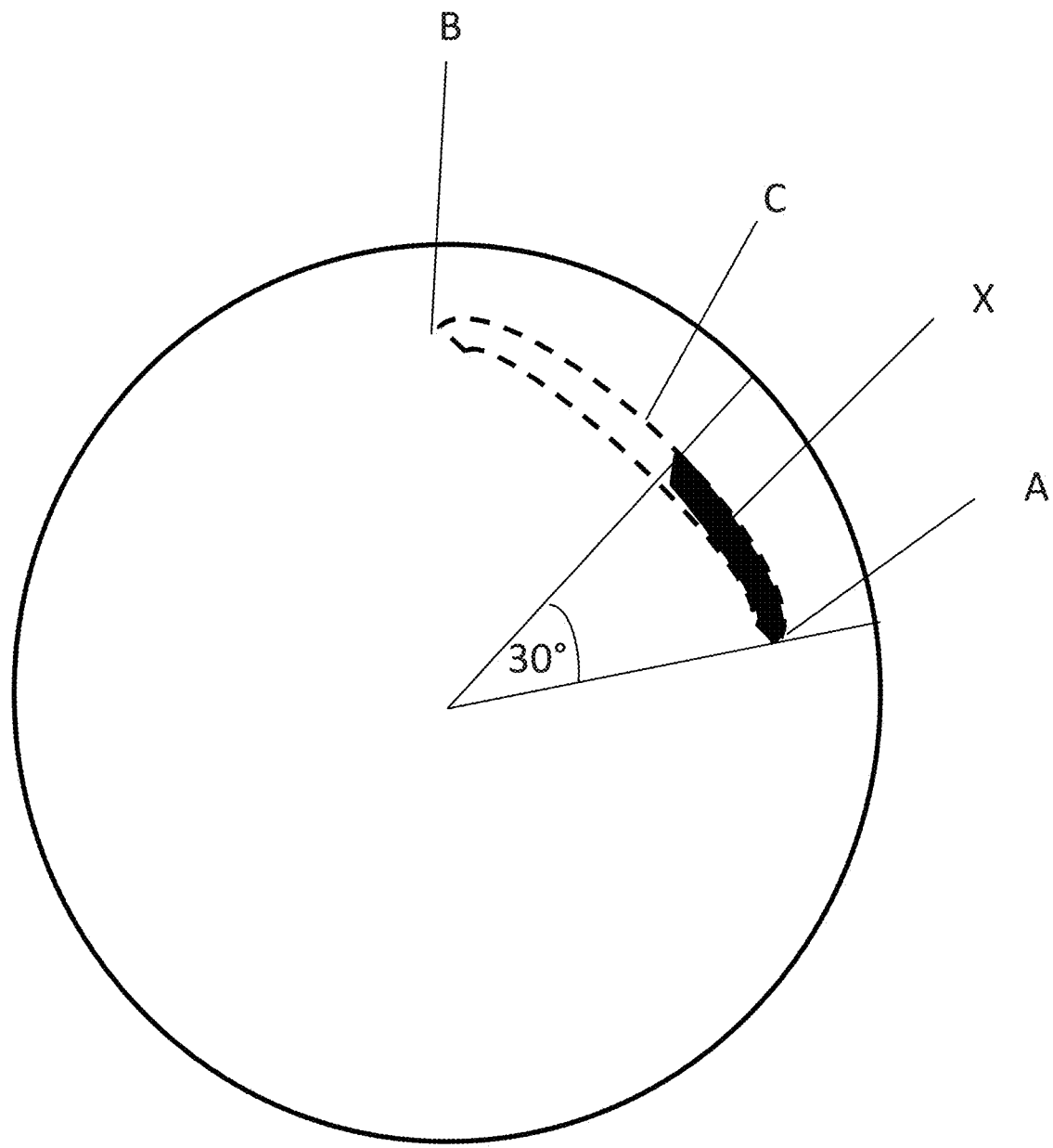
FIG. 12 illustrates the path of ablation at a treatment site using the sweeping action of the automated ablation element.

For example, FIG. 12 illustrates the path of ablation at a treatment site using the sweeping action of the automated ablation element 140. Like the embodiments discussed above, the automated ablation element 140 can be configured to emit an arcuate shaped ablation segment (X) of about 30 degrees (or another predetermined number of degrees) at any single location (as described herein, the angular measurement of the emitted energy is measured relative to the energy emitter and more specifically, the emitted energy has a prescribed subtended angle relative to the energy emitter. However, unlike the above embodiments, the sweeping action (caused by the controlled rotation of the ablation (energy) emitter) provided by the automated ablation element 140 allows it to move a predetermined number of degrees to one or both sides of the initial location of ablation in an arcuate path (sweeping motion) consistent with the initial ablation segment, thereby creating an arcuate shaped ablation segment greater than 30 degrees. In other words, the automated ablation element can be configured to sweep from the initial location of ablation (a first endpoint) to a second endpoint which is at the opposite end of the arcuate shaped ablation. In FIG. 12, while the initial arcuate shaped ablation segment X is at a first endpoint A, the sweeping action allows the automated ablation element to ablate from endpoint A to endpoint B in a sweeping motion, thereby creating a larger formed lesion segment. As described herein, one or more of the endpoints can be inputted by the user using a user interface, such as a touchscreen or other type of interface that allows the user to view the target ablation site and then mark the locations of the one or more endpoints. The coordinates of the one or more endpoints are then stored and in the case of the starting point, the ablation element is moved to the first stored coordinates (that identify and relate to the starting point) and the ablation process begins and in particular, the ablation element moves in a sweeping manner. In the case that the end point is also inputted by the user, the sweeping motion is designed so that the ablation element does not extend beyond the stored coordinates for the end point. This ensures that the formed arcuate shaped lesion is formed between the start point and the end point.

In at least one embodiment, the initial location of the automated ablation process can be the midpoint of the sweeping action for a given arcuate-shaped ablation segment. In other words, the automated ablation element can be configured to sweep left and right of the initial location of ablation (midpoint). For example, with reference to FIG. 12, the initial arcuate shaped ablation segment could begin at a midpoint C, and the automated ablation element could create a larger lesion segment by sweeping between endpoints A and B (as by rotating in a first direction toward point A and by rotating in a second direction toward point B). As such, with the automated ablation element, fewer lesion segments are needed to complete the continuous lesion and moreover, the process is more automated and requires less direct surgeon input and control over the energy emitter.

In one or more implementations, the automated ablation element 140 can be configured to sweep multiple times between endpoints of the ablation segment to complete the lesion segment. In at least one implementation, one "sweep" from one endpoint to the other endpoint of the segment is sufficient to complete the lesion segment.

Further, in the embodiments discussed above, ablative energy is directed to a single location to create a lesion segment, and once the lesion segment is created, the ablation element 140 is moved to a different (but overlapping) location, to create a second lesion segment. The movement of the ablation element to another location can be performed manually by the user or it can be part of an automated process in which based on the user's observation of the tissue at the target location and the quality and nature of the just ablated tissue (e.g., visual observations of the display of the user interface), the user can enter input commands to controllably move the ablation element to initiate the ablation process, such as a new sweeping action over a defined number of degrees. Once again, this new sweeping action can and typically does include some degree of overlap with the just previously formed lesion segment. The degree of overlap can be controlled and entered by the user as part of input control commands that control the operation (sweeping action) of the ablation element. Thus, if the ends of the arcuate shaped formed lesion include overlap from two discrete sweeping actions, the controller (related software) uses this information to calculate the degree of motion (including the residence time) of the ablation element in an intermediate region between the ends of the ablation segment.

As described herein and according to one implementation, the user begins by inputting a start point A and an endpoint B and then, the processor calculates the full path of the sweep to achieve a lesion extending between points A and B before energy delivery is initiated. The user then initiates energy delivery (via the energy emitter) and the sweeping of the energy emitter begins.

As described herein and according to another implementation, the user inputs a power level. The present system calculates an appropriate angular rate of sweep speed based on the power level. Then user then sets a start point of the sweep. Thus user initiates energy delivery (via the energy emitter) and the sweeping of the energy emitter. The user then terminates energy delivery and sweep once the desired end point is reached based on visual observation of the endoscopic image. This embodiment is thus thought of as being one in which the end point of the sweep is determined by the user "on the fly". In other words, the user set the start point but can stop the path of the sweep at any time based on information received from the visualization device or other obtained information.

This process of creating overlapping lesion segments is repeated until a continuous lesion is completed (formed). In the present embodiment for the automated ablation element, overlapping lesion segments are still formed; however, each formed lesion segment has a greater arc length due to the rotation (sweeping action) of the ablation element during ablation of the tissue. Thus, the continuous lesion can be created using fewer overlapping lesion segments as compared with the previous embodiment in which each arcuate shaped ablation segment is formed by emission of energy when the ablation element is fixed at one position. However, if the automated ablation element 140 uses the same amount of ablative energy (power) as the previous embodiment, the longer arcuate length lesion segments of the present embodiment would take longer to complete as the ablative energy is not directed to each location along the arc for as long a period of time (residence time) as compared with the stationary ablative element of the previous embodiment. As such, in one or more implementations, the power (energy) of the automated ablation element can be increased relative to the previous embodiment, such that a longer arcuate length lesion segment can be completed in a reduced amount of time. One of skill in the art will readily understand that the completeness and quality of the ablation depends largely on the level of power (energy) of the ablation element and the residence time of the ablation element over the target tissue (i.e., how long the ablation energy is emitted).

In further aspects of the automated ablation element embodiment, the overlap of the lesion segments can be minimal relative to the previous embodiment since the automated nature of the sweeping action of the ablation element allows for very precise control over the movement of the ablation element. As such, fewer lesion segments are needed to complete the continuous lesion. Further, in at least one embodiment, the automated ablation element can be configured to perform a real-time electrical assessment to confirm that a continuous lesion has been achieved. For example, the catheter can include electrodes that that are configured to provide an electrical assessment of the sufficiency and quality of the formed lesion. As is known in the art, if the formed lesion includes any defect, such as a gap or break along its circumference, an electrical transmission will pass through such gap or break and can be detected.

Figure 13:
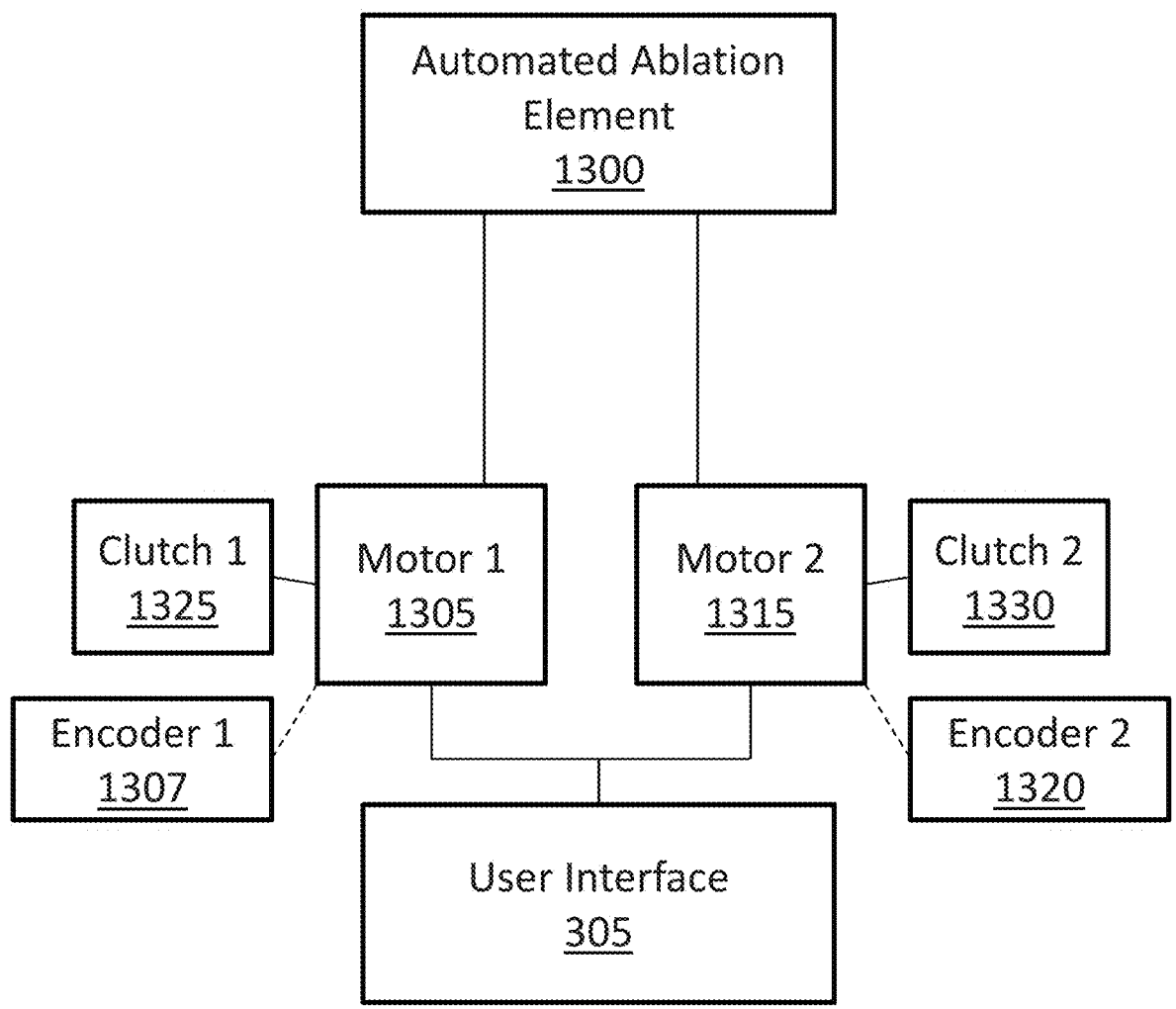
FIG. 13 is a block diagram of a computer system configured to control the motor of the automated ablation element.

The components of one exemplary automated ablation element 140, in accordance with at least one embodiment, are shown at FIG. 13. The automated ablation element 1300 can include a first motor 1305 configured to rotate the ablation element in a sweeping motion. In a preferred embodiment, the first motor 1305 is a servomotor, which allows for precise positioning, acceleration, and movement of the ablation element so as to achieve the desired sweeping motion thereof. The first motor 1305 can be coupled with a first encoder 1307, such as a rotary encoder. The first encoder 1307 is configured to provide position feedback and/or speed feedback to help control the motion and final position of the ablation element 1300. In one or more embodiments, the first motor 1305 can have a 1:1 gear ratio such that there is 1 motor rotation for every 1 rotation of the knob that is connected to a drive shaft for rotating the ablation element 1300.

It will be appreciated that the present ablation instrument can have other mechanical linkages for operatively connecting the first motor 1305 to the ablation element resulting in the controlled rotation of the ablation element in a sweeping manner (e.g., arcuate movement in a back and forth manner).

In at least one embodiment, the automated ablation element 1300 can include a second motor 1315 configured to move the ablation element axially within the catheter body and thus axially within the balloon. Accordingly, both the axial movement and rotation of the ablation element 1300 can be controlled in an automated manner as by mechanically linking the ablation element to one or more motors which control the movements of the ablation element. In certain embodiments, the second motor can also be coupled with a second encoder 1320 to control the axial movement of the ablation element.

It will be appreciated that the first and second motors 1305, 1315 can be operated successively or concurrently. When operated successively, the user first moves, in an automated manner, the energy emitter 140 either in the axial direction (which causes a change in the circumferential length of the formed lesion segment) or in a rotational direction, as described herein, and then performs the other operation. When used concurrently, the energy emitter moves axially and has a rotational movement component.

Figure 14:
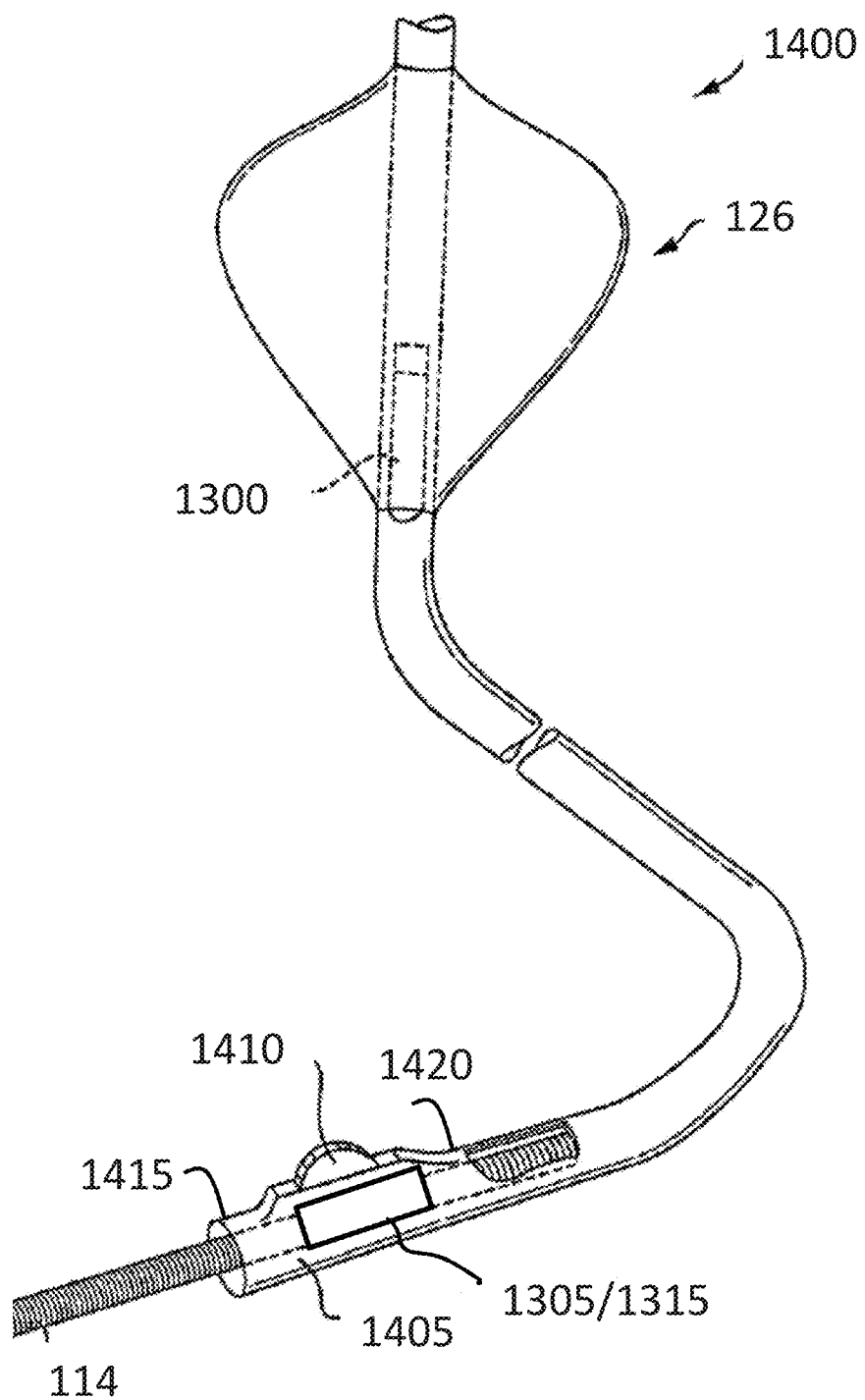
FIG. 14 is a schematic view of the cardiac ablation instrument comprising the automated ablation element, the ablation instrument further including a handle having one or more motors for controlling the movement of the automated ablation element.

The one or more motors 1305, 1315 can be located in any number of different locations. A schematic view of the cardiac ablation instrument 1400 comprising the automated ablation element 1300 including one or more motors is shown at FIG. 14. In FIG. 14, the one or more motors (1305/1315) can be located in a handle 1405 of the ablation instrument 1400. In particular, the handle 1405 can comprise an actuator 1410 for use by the operator to control the axial and/or rotational movement of the ablation element 1300 via motors 1305 and 1315. Further, the handle 1405 can be operably connected to a console at its proximal end 1415 and operably connected to the catheter (comprising the ablation element 1300) at its distal end 1420.

The console can comprise a display (display 14) and can be used to control the catheter and automated ablation element as discussed in further detail below. In implementations in which the one or more motors are located in the handle, the handle is re-sterilized following each procedure to ensure proper sanitary conditions.

Alternatively, the one or more motors (e.g., 1305/1315) can be located in the console of the instrument, or a separate unit that the handle is operatively connected to. In embodiments in which the motor(s) is located in the console or a separate unit, the motor can be connected to the ablation element via a drive shaft, which can be housed in a flexible cable. As such, in this embodiment, the motor does not need to be sterilized between uses as it will not be in contact with the patient. In this configuration, the drive shaft can be in the form of an elongated structure that is housed in the flexible cable and is operatively connected to the ablation element to cause rotation and/or axial movement thereof. The motor thus can be located remote from the catheter itself.

Referring again the FIG. 13, in one or more implementations, the ablation element 1300 can further include a first clutch 1325 and/or second clutch 1330. The one or more clutches (1325/1330) can be configured to disengage to avoid damage to the motor if the rotational or axial movement of the ablation element becomes jammed. Alternatively, the clutch (1325/1330) can be a slip-clutch, designed to slip when greater-than-normal resistance is encountered by the ablation element during rotational or axial movement. This mechanism thus protects the mechanical components of the device and prevents over internal damage due if unexpected resistance is encountered during controlled movement of the ablation element. In one or more embodiments, the pathway of the ablation for the automated ablation element can be predetermined by the operated using a graphical user interface (GUI) 305. In particular, using the GUI 305, the operator can input various parameters in order to program the pathway of the automated ablation element. The input parameters can include but are not limited to: the degree of the arc of ablation, the initial ablation location and end point(s) of the sweeping action, the power of the ablation energy for the particular ablation run, and the length of time for each sweeping motion. These parameters can be set and adjusted by the operator using the GUI 305. In at least one embodiment, software can be used to determine the pathway of the automated ablation element using certain parameters inputted by the operator, such as the initial ablation location and intermediate point, and the end point of the ablation. In this embodiment, the software (e.g. based on an algorithm), rather than the operator, can calculate the pathway of the ablation, including the degree of the arc and the power of the ablation energy, based on a few input parameters. In one or more embodiments, the input parameters can be modified by the operator before and during the process of creating a continuous lesion via ablation.

The operator can input parameters using the GUI 305 via various methods such as an input joystick or a touchscreen operatively connected to the console of the instrument. The operator can view the input parameters for the ablation element on the display of the console. Once the pathway is determined (either by the operator or by the software), the ablation instrument can be configured to perform a test run in which the ablation element is axially moved within the catheter to the desired location and rotated at the desired location, but no ablative energy is used. More specifically, the motor (via input using the GUI) can configure the automated ablation element to rotate the ablation element back and forth in a sweeping motion at the location of ablation, but without ablating the tissue. Instead, only an aiming light (beam) attached to the ablation instrument (as described in further detail below) is activated. As such, this test run can be used to confirm the pathway of the ablation using the aiming beam prior to ablating the tissue. Once the test run has confirmed the pathway, the ablation instrument can be configured to perform the ablation.

The ablation instrument can optionally feature a manual override device (e.g., knob) allowing the operator to manually control the rotational and/or axial movement of the automated ablation element. In one or more embodiments, the manual override device (knob) can be located on the console. In certain embodiments, the operator can manually override the input parameters to alter the positioning and/or pathway of ablation element. In at least one embodiment, the motor can also have an override feature to maintain the ablation power and pathway if the manual knob (that controls manual movement of the ablation element) is moved accidently during ablation.

Figure 15:
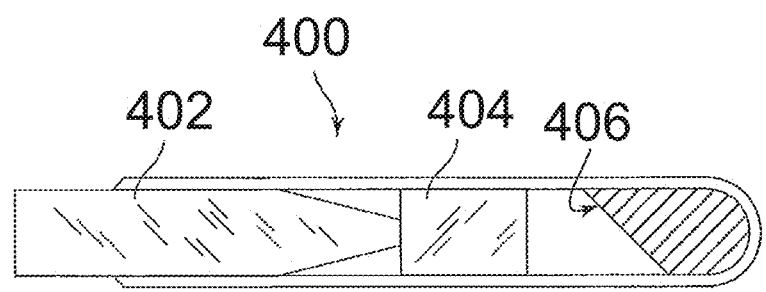
FIG. 15 is a cross-sectional view of one exemplary ablation element.
Figure 16:
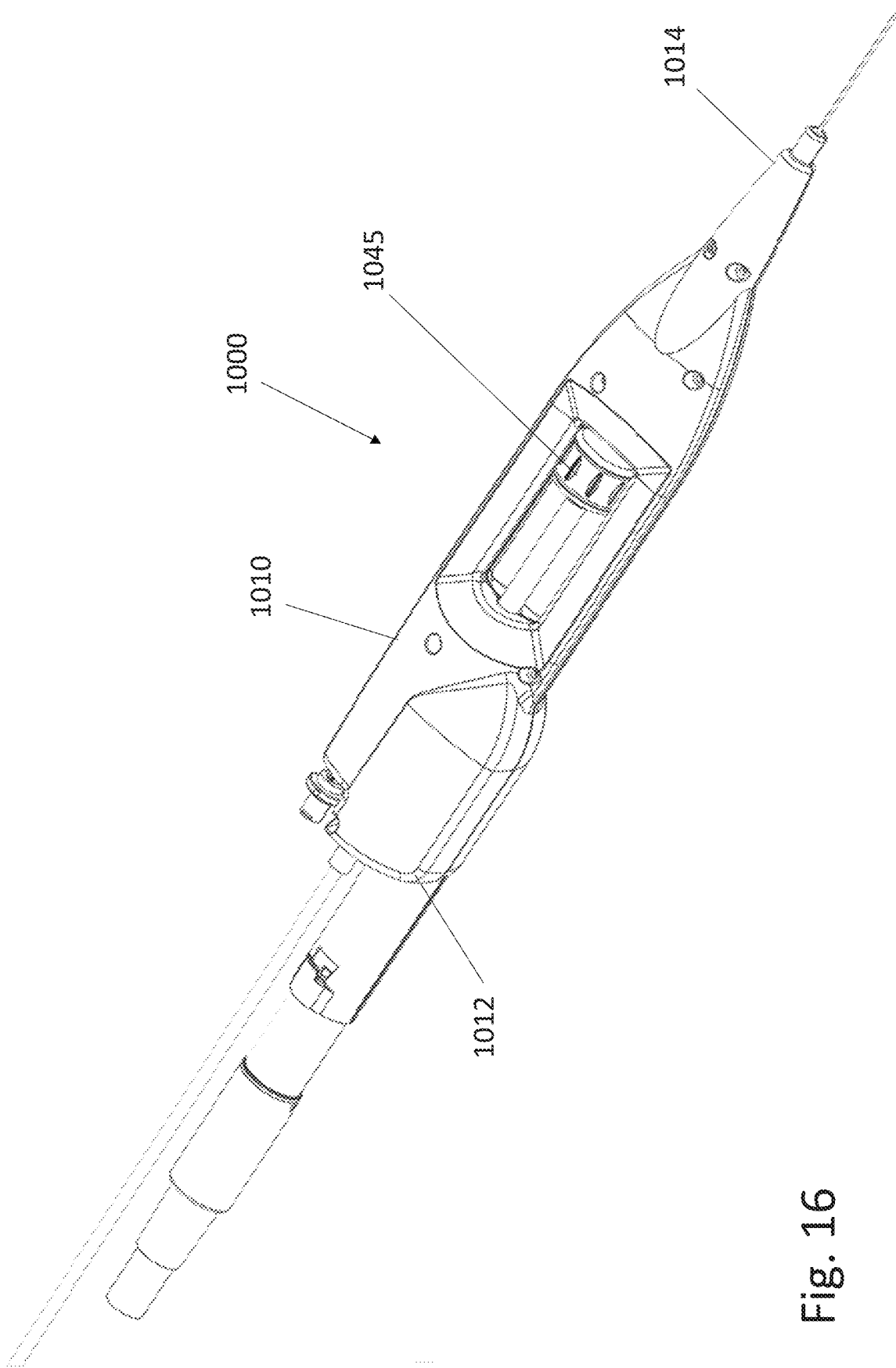
FIG. 16 is a perspective view of an ablation instrument according to another embodiment.
Figure 17:
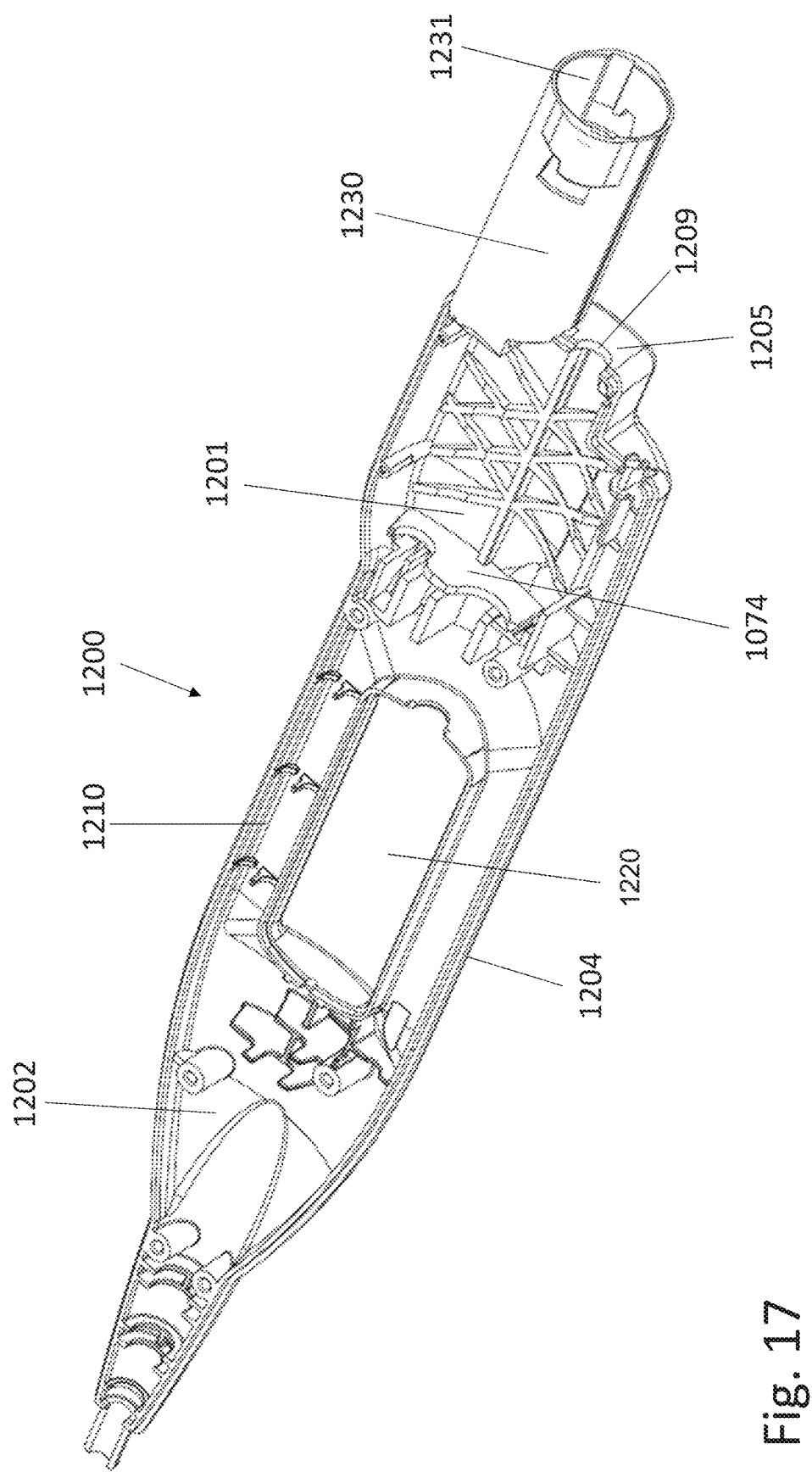
FIG. 17 is a perspective view of a bottom handle housing part.

In one or more implementations, as illustrated in FIG. 15, an automated ablation element can comprise an optical fiber, such as a chiseled-end optical fiber, a graduated refractive index (GRIN) lens and a reflector. More particularly, FIG. 15 is a schematic cross-sectional illustration of one embodiment of a radiant energy emitter 400 according to the invention. In one embodiment, the radiant energy is electromagnetic radiation, e.g., coherent or laser light, and the energy emitter 400 projects a beam of radiation that forms a spot or arc-shaped exposure pattern upon impingement with a target surface. For example, radiant energy emitter 400 can include an optical fiber 402, the distal end of which can be beveled into an energy-emitting face of reduced cross-section. The fiber 402 passes a beam of light to a gradient index (GRIN) lens 404, which serves to collimate the beam, keeping the beam width substantially the same, over the projected distance. The beam that exits the GRIN lens 404 is reflected by reflector 406 in an angular direction from about 5 degrees to about 110 degrees relative to from the light's path along the longitudinal axis of the catheter. Generally, the angle of reflection from the central axis of the optical fiber 402 can range from about 30 to nearly 90 degrees. In other words, the angle of projection, from the optical axis of the fiber 402 (or lens 404) will be between about 5 to 60 degrees forward of perpendicular. The reflector 406 can be in the form of a total internal reflecting (TIR) mirror element; however, other types of suitable reflectors can be equally used. Suitable automated ablation elements are disclosed in U.S. Pat. No. 8,696,653, which is hereby incorporated by reference in its entirety.

In one or more implementations, the automated ablation element can further comprise a foot pedal to allow for control over one or more operations of the catheter. For example, a foot pedal can be used to apply power to the ablation element and also can be used to control the operation of one or more of the motors described above.

Aiming Light

Since the radiant energy (e.g., a laser) emitted from the energy emitter 140 is typically outside the visual light spectrum that can be detected by the human eye, the ablation instrument 100 includes an aiming light preferably having a pulsed operating mode in which visible light from the aiming light unit is delivered in pulses to cause intermittent illumination of the tissue at the target site 152. This gives the aiming light an appearance of being a blinking light. By delivering the visible aiming light in pulses, the electrophysiologist is able to directly observe the tissue while it is being treated at the target site 152, using an endoscope, between the aiming light pulses.

During an ablation procedure, the endoscope 176 is used to determine the extent of tissue ablation by sensing the change in appearance of the tissue as it is ablated and at a time when the aiming beam is in an off cycle via the display 14. In other words, between the blinking (pulses) of the aiming light, the electrophysiologist can observe the treated tissue to determine how the treatment is progressing since the endoscope 176 is used to determine the extent of tissue ablation by sensing the change in appearance of the tissue as it is ablated and at a time when the aiming beam is in an off cycle. However, many conditions may cause the actual detection of change in appearance of the tissue being ablated to be difficult and/or unreliable in regards to whether proper spot lesions are formed by the energy transmitter 140 on the tissue at the ablation treatment site 152. For instance, insufficient illumination at the treatment site 152 can make it difficult, if not impossible, to ascertain whether proper spot lesions were formed at the treatment site as viewed on display 14.

As also described herein, the endoscope 176 is also used to sense a change in the degree of movement or perturbation in the distal pulmonary vein blood pool).

Figure 7:
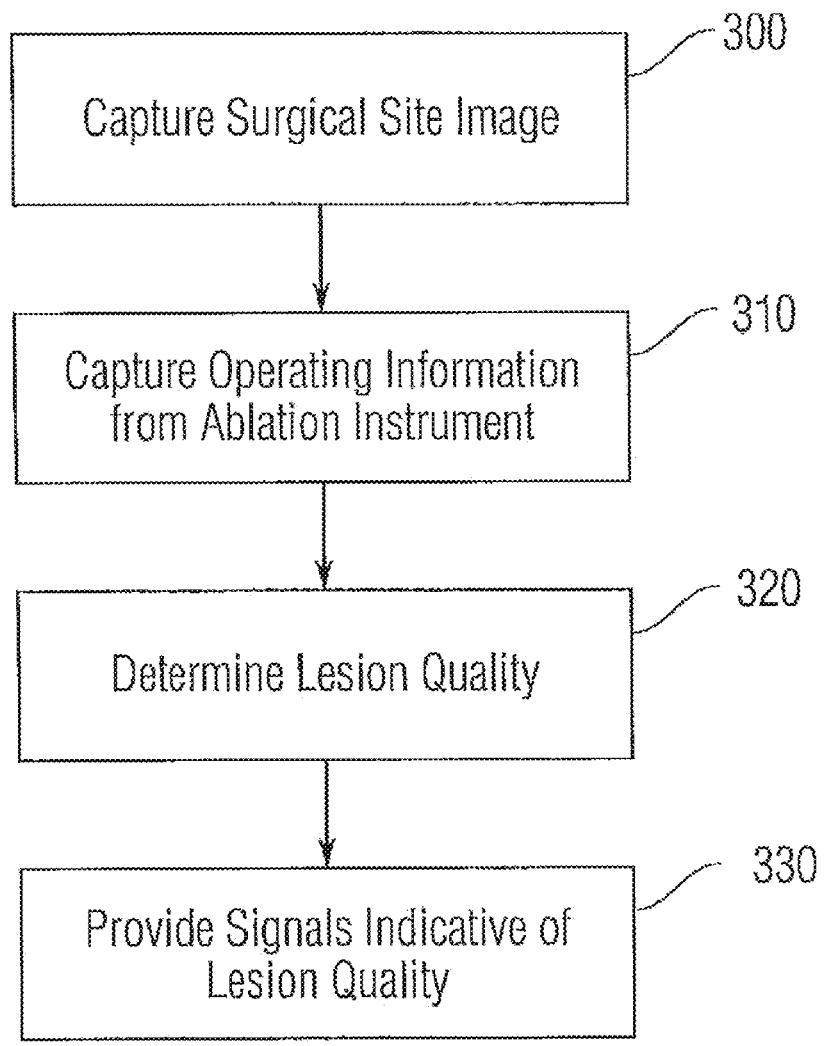
FIG. 7 is a flow diagram illustrating the steps performed by the ablation system of FIG. 1 for determining the quality of lesions formed during treatment that entails an intracardiac ablation procedure.

The processor 12 of ablator system 10 obviates this problem by determining the quality of the lesion formed on the tissue at the target site 152 which may be viewed on monitor 14 and/or indicated to an electrophysiologist via visual overlay or audio cues. With reference now to the flow diagram of FIG. 7, the method of operation for determining the quality of spot lesions at an ablation treatment site 152 will now be discussed.

Starting at step 300, the processor 12 captures the image from endoscope 176 of the tissue being ablated at the treatment site. At step 310, the processor 12 also captures information relating to the energy transmitter 140 from controller 16. The captured energy transmitter 140 information includes: the amount of radiant energy (power) applied by energy transmitter 140 on the tissue at the treatment site 152 to form spot lesions; the distance the energy transmitter 140 is from tissue to be ablated via spot lesions; and the rate of movement of energy transmitter 140 relative to the tissue at the treatment site 152. It is to be appreciated that aforesaid information captured regarding energy transmitter 140 is not to be understood to be limited thereto as more or less information may be captured that is necessary to determine the quality of the spot lesions formed on the tissue at the treatment site and/or visually determine the completion of the procedure by observation of a change in the characteristics of the blood pool in the pulmonary vein.

The processor 12 then preferably uses algorithmic techniques to determine whether a sufficient spot lesion has just recently been formed on the tissue at the treatment site (step 320). In other words, given the distance the energy transmitter 140 is located from the tissue at the treatment site 152, the rate of movement of the energy transmitter 140 relative to the tissue at the treatment site 152 (e.g., the amount of time that energy is applied to the tissue at a given location), and the amount of energy being applied, a determination is made as to whether a sufficient spot lesion has been formed on the tissue at a location which the energy transmitter is applying ablation energy thereto. A lookup table or other similar means may also be used by processor 12 for determining the aforesaid lesion quality. A spot lesion is to be understood as being sufficient when it comprises enough scar tissue effective to block the transmission of electrical signals therethrough.

The processor 12 is preferably further operative and configured to provide a signal to the electrophysiologist indicative of whether a sufficient spot lesion has been formed (step 330). This indicative signal may be provided in the event an insufficient or no spot lesion was formed on the tissue at the treatment site 152 that was subject to the energy transmitter 140 dispersing energy thereto. This indicative signal may be an audio and/or visual signal. The audio signal may consist of a warning tone and the visual signal may consist of a marker (e.g., color red) superimposed on the display 14 illustrating the treatment site 152 (provided via endoscope 176) at the location at which the insufficient spot lesion was determined. Thus, when image processor 12 determines an insufficient spot lesion has been formed, the aforesaid warning signal is promptly provided to the electrophysiologist enabling the electrophysiologist to revisit the tissue having the insufficient lesion and make proper adjustments with the energy transmitter 140 (e.g., apply more energy, close the distance between energy transmitter 140 and the treatment site and/or slow the movement of energy transmitter 140 relative to the treatment site) so as to now form sufficient lesions.

Figure 9:
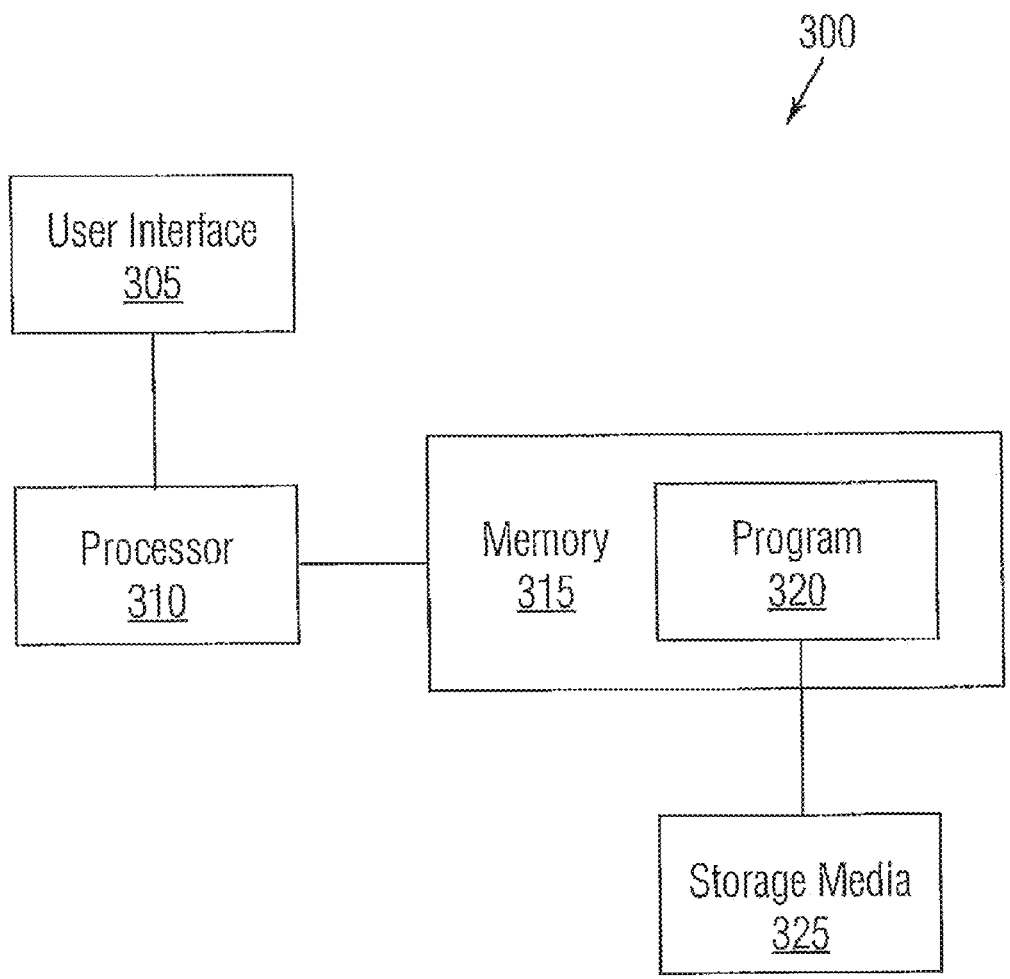
FIG. 9 is a block diagram of a computer system configured to employ one ablation method of the present invention.

FIG. 9 is a block diagram of one computer system 300 configured for employment of method 100. System 300 includes a user interface 305, a processor 310, and a memory 315. System 300 may be implemented on a general purpose microcomputer, such as one of the members of the Sun® Microsystems family of computer systems, one of the members of the IBM® Personal Computer family, one of the members of the Apple® Computer family, or a myriad other conventional workstations. Although system 300 is represented herein as a standalone system, it is not limited to such, but instead can be coupled to other computer systems via a network (not shown).

Memory 315 is a memory for storing data and instructions suitable for controlling the operation of processor 310. An implementation of memory 315 would include a random access memory (RAM), a hard drive and a read only memory (ROM). One of the components stored in memory 315 is a program 320.

Program 320 includes instructions for controlling processor 310 to execute method 100. Program 320 may be implemented as a single module or as a plurality of modules that operate in cooperation with one another. Program 320 is contemplated as representing a software embodiment of the method described hereinabove.

User interface 305 includes an input device, such as a keyboard, touch screen, tablet, or speech recognition subsystem, for enabling a user to communicate information and command selections to processor 310. User interface 305 also includes an output device such as a display or a printer. In the case of a touch screen, the input and output functions are provided by the same structure. A cursor control such as a mouse, track-ball, or joy stick, allows the user to manipulate a cursor on the display for communicating additional information and command selections to processor 310.

While program 320 is indicated as already loaded into memory 315, it may be configured on a storage media 325 for subsequent loading into memory 315. Storage media 325 can be any conventional storage media such as a magnetic tape, an optical storage media, a compact disc, or a floppy disc. Alternatively, storage media 325 can be a random access memory, or other type of electronic storage, located on a remote storage system.

The methods described herein have been indicated in connection with flow diagrams that facilitate a description of the principal processes; however, certain blocks can be invoked in an arbitrary order, such as when the events drive the program flow such as in an object-oriented program. Accordingly, the flow diagram is to be understood as an example flow and that the blocks can be invoked in a different order than as illustrated.

It should be understood that various combination, alternatives and modifications of the present invention could be devised by those skilled in the art. The present invention is intended to embrace all such alternatives, modifications and variances that fall within the scope of the appended claims.

Although described in connection with cardiac ablation procedures, it should be clear that the instruments and systems of the present invention can be used for a variety of other procedures where treatment with radiant energy is desirable, including laparoscopic, endoluminal, perivisceral, endoscopic, thoracoscopic, intra-articular and hybrid approaches.

Thus, the instrument 100 is merely exemplary of one type of ablation device that can be used in combination with the endoscope/imaging device of the present invention.

Figure 10:
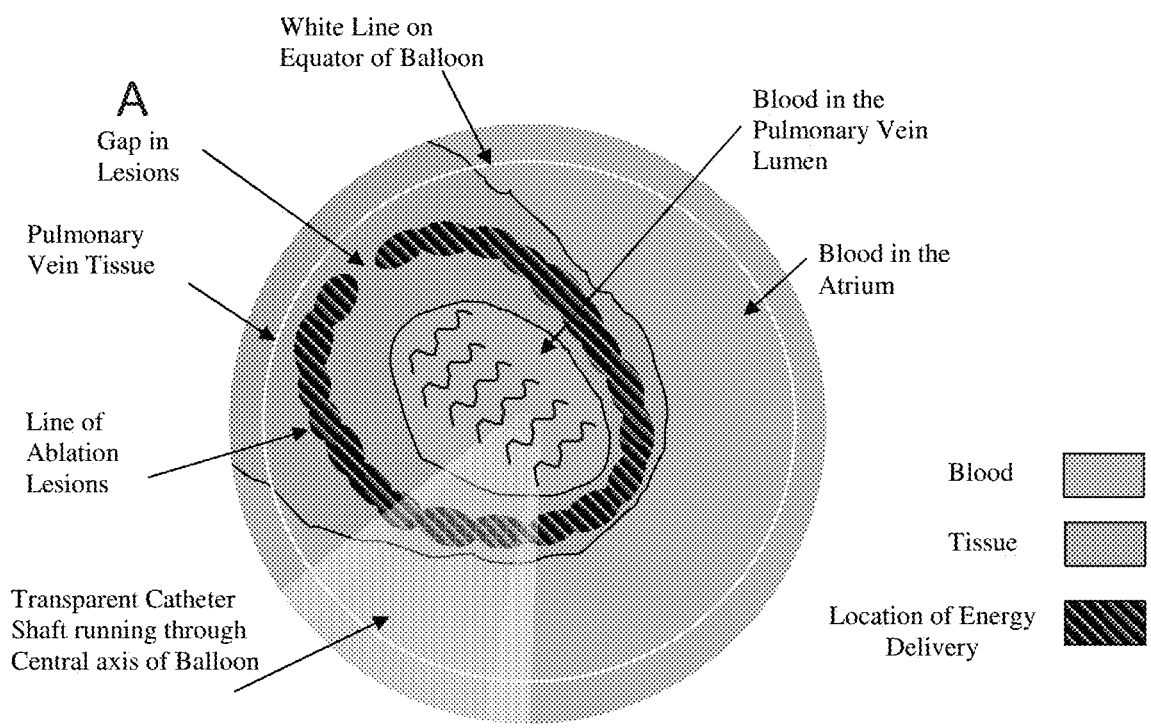
FIG. 10 is a representative view of a treatment site, prior to beginning the ablation procedure, from along a longitudinal axis of a catheter.

Visual Confirmation of Target Tissue (e.g., a Pulmonary Vein) Isolation by Monitoring Blood Pool Characteristics FIG. 10 is a representative endoscopic view of a treatment site from along a longitudinal axis of the catheter. This view is preferably displayed on a display, such as a monitor and the ablated tissue can be displayed in a visually distinguished manner relative to the de-novo (untreated) tissue.

Figure 11:
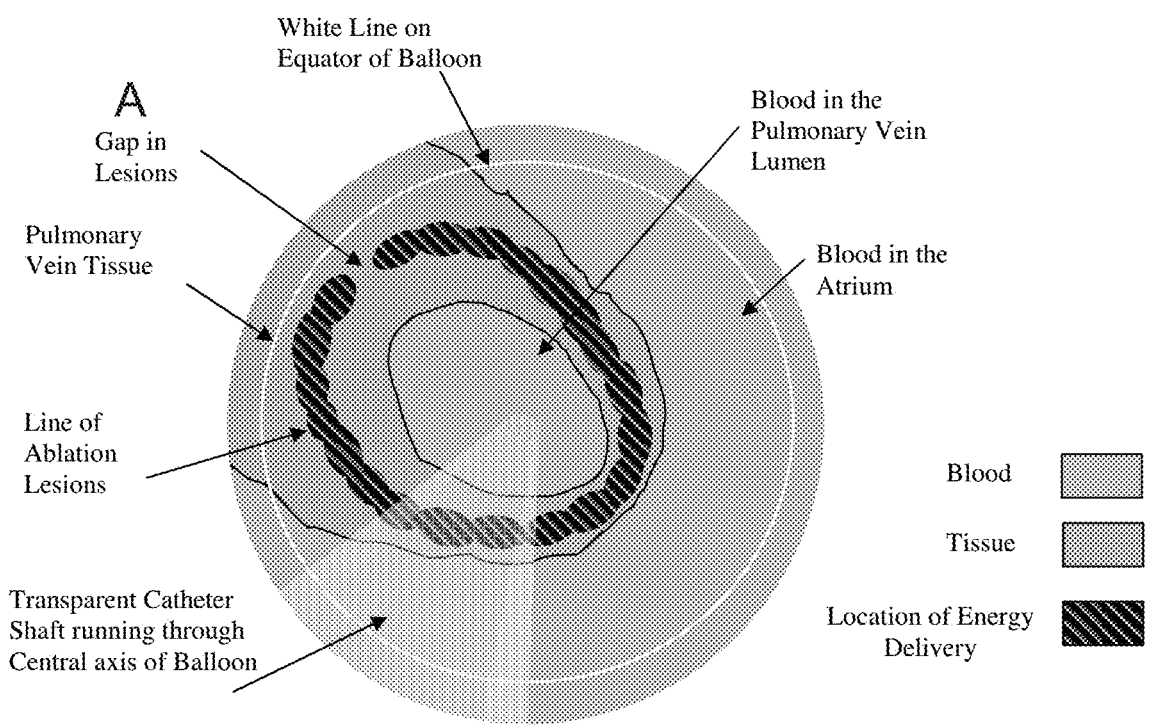
FIG. 11 is a representative view of a treatment site, after completion of the ablation procedure, from along a longitudinal axis of a catheter.

In FIGS. 10 and 11, the areas of blood/tissue are visually differentiated from the locations of the energy delivery (the formation of the lesions) by the use of cross-hatching. The catheter shaft and balloon are also visually distinguished from the blood/tissue and the lesions (by cross-hatching). As discussed herein, in FIGS. 10 and 11, the cross-hatched areas denote blood/tissue.

The principles of the present invention are readily appreciated in view of FIG. 10 and FIG. 11 in which FIG. 10 shows the treatment site prior to beginning the ablation procedure, while FIG. 11 shows the treatment site after completion of the ablation procedure and after a complete ablation is formed. As will be apparent from viewing FIGS. 10 and 11, the blood pool in FIG. 10 is shown as having increased perturbation as a result of contraction of the muscles at the target site. For example, the target site can be the pulmonary vein and thus, the contraction of muscles around the pulmonary vein causes such perturbation in the distal blood pool. Visually, the blood pool will have the appearance similar to a rough ocean in that there is high degree of waves and other local disturbances particularly evident at the borders between blood and tissue. Conversely and after the pulmonary vein has been effectively isolated as a result of a complete continuous lesion (ablation) being formed around the pulmonary vein, the distal blood pool (i.e., the blood in the pulmonary vein) has a much reduced visible pattern of perturbation (due to a reduction in electrical activity/electrical isolation at the target site). Visually, the blood pool will have a more placid appearance compared to the initial appearance (which is more vigorous and choppy, etc.). Thus, as described herein, a comparison between the initial image (which serves as a baseline) and a real-time image is indicative and can be used to determine, in real-time, if the ablation is complete (i.e., if the lesion was formed successively so as to isolate the target tissue, which in this case is around pulmonary vein).

The Imaging System

The imaging system in accordance with the present invention includes an appropriate imaging device that is configured to monitor, in real time, the condition of the tissue at the treatment site and in particular, allow the physician to readily distinguish between ablated tissue and de novo tissue that has not been ablated. The imaging system also further allows the physician to monitor, in real-time, the conditions of the distal blood pool (e.g., blood within the pulmonary vein) prior to beginning the procedure, during the procedure and after the procedure is complete. The imaging system allows the observed image to be displayed in real-time on a display and/or recorded and stored in memory.

An endoscope (as discussed previously) can be used to obtain an image of the ablated tissue as described herein. The endoscope is inserted into the body of the catheter and positioned adjacent the area of interest to allow viewing in real-time of the area.

It will be appreciated that the imaging system of the present invention is not limited to the use of an endoscope but instead, any number of different types of imaging systems can be used so long as they provide a real-time image of the treatment site that can be observed on the display.

Image Analysis (Software)

The software of the present invention can be configured such that the visual patterns of the distal blood pool can be analyzed. As discussed herein, contraction of the muscles at the target site is caused by electrical conduction across the tissue and this normal muscle traction will cause the distal blood pool (e.g., the blood in the pulmonary vein) to have increased perturbation. Increased perturbation can be observed visually in that the blood will have certain characteristics that are indicative of blood motion or perturbation. For example, highly perturbed blood will have a set of visual characteristics/patterns such as an increased appearance of waves and other local distortions/disturbances that are visible especially at the blood/tissue border. The blood will not have a smooth, flat uniform appearance when the muscles are contracting at the target site. Thus, the baseline image that is preferably stored in memory before the procedure begins will show the visual condition of the blood pool when it is subjected to muscle contraction.

As the ablation procedure begins and the lesion series (ablation) is formed at the target site, decreased electrical activity occurs due to the lesion formation causing progressive electrical isolation of the target (e.g., the objective can be to electrically isolate the pulmonary vein). The decreased electrical activity is a result of less muscle contraction at the target site and therefore, the characteristics of the distal blood pool will likewise change. For example, there will be a progressive lessening in the degree of perturbation (degree of local disturbances) of the distal blood pool. In other words, as the ablation procedure continues, the distal blood pool increasingly has more of a placid visual appearance due to a lessening in the perturbation characteristics (local disturbances) that are present in the baseline image.

The software can also be configured such that a degree of turbulence in the distal blood pool or the actual displacement of the blood/tissue border can be classified using a scoring system which includes analyzing the degree of correlation between the visual image of the distal blood pool prior to beginning the ablation procedure (i.e., the baseline image) and the real-time image of the distal blood pool. More specifically, the software has a processor that compares the real-time image to the baseline image and determines the degree of correlation. An algorithm can be used to calculate the degree of correlation between the real-time image and the baseline image and it is desirable in such comparison that the degree of correlation is low. In other words, it is desirable that the real-time image not have the visual characteristics of the baseline image since it is desirable that the distal blood pool have a placid appearance or close thereto after a complete lesion is formed.

Alternatively, the processor can be configured to compare the real-time image with an optimal image that represents a placid blood pool (i.e., an ideal condition indicative of complete electrical isolation of the target tissue (e.g., pulmonary vein)). In this embodiment, it is desirable to have a high degree of correlation between the real-time image and the optimal image since the optimal image represents perfect electrical isolation of the target. In yet another embodiment, the processor can use both the initial pre-procedure image and the optimal image to calculate the quality of the ablation and more particularly, calculate the level of isolation of the target tissue. The software and method of the present invention thus provides for visual confirmation of pulmonary vein isolation during the ablation procedure.

It will also be appreciated that the processor can be used to compare or contrast more characteristics that are indicative of blood perturbation in order to assess the degree of electrical isolation of the target tissue. By comparing the one or more characteristics, the processor can be configured to calculate the degree of completeness of the ablation by analyzing the real-time image relative to the baseline image.

It will also be appreciated that the baseline image can be visually distinguished from the real-time image by use of different colors for each of the images. For example, the baseline image can be displayed with a first color of the display (e.g., monitor) and the real-time image can be displayed with a second color that is visually distinguishable relative to the first color. Thus, when the two images are superimposed (e.g., the real-time image overlies the baseline), the differences in the level of perturbation of the distal blood pool can be visually detected. For example, the baseline image, in the first color, is represented by visual indicia (such as wave lines), while the real-time image is represented by much less visual indicia (such as wave lines) in the second color or alternatively, a smooth placid blood pool will be represented by a lack of indicia that represents perturbation (i.e., a lack of wave lines). Thus, the lack of indicia, in the second color, is indicative that the ablation is complete and the target site (e.g., the pulmonary vein) has been electrically isolated. Image registration software can then be used to combine the two images in proper alignment.

The type of visualization is especially important in intra-operational use where it is desirable for the physician to understand the quality of the formed ablation and whether the main objective of electrically isolating the target tissue has been achieved.

In accordance with the present invention, one technique for detecting a significant change in the movement of the distal blood pool border comprises measuring the excursion of the border of the blood pool and involves the following steps: (a) provide a signal gated to either a high voltage recurring component of the ECG or at the point of photographic evidence of the maximum excursion of the blood pool border throughout the cardiac cycle; (b) measure the length of two or more orthogonal diagonals at the time of activation gated to either of these signals; (c) compute a first maximum, minimum, and average length measurement; (d) measure the length of two or more orthogonal diagonals at a recurring isoelectric ECG phase in between gated activation or at the point of photographic evidence of the minimum excursion of the blood pool border throughout the cardiac cycle; (e) compute a second maximum, minimum and average length measurement; (f) calculate a difference between the first and second measurements; (g) provide a means to program an indicator representing an achievement of a predetermined percentage reduction in the excursion of the border of the blood pool measurements or at a point potentially referencing a representative point at which electrical activity has been shown to have been eliminated.

Review of Ablation Quality

The present invention thus allows the electrophysiologist to view the formed ablation(s) (lesion) in real-time and to evaluate the quality of the formed ablation(s) to allow the electrophysiologist to decide whether additional ablation treatment is needed. For example, if the electrophysiologist views the display and receives feedback that the target tissue (pulmonary vein) has not been electrically isolated as a result of the formed ablation(s) including a defect, such as a void (gap or break) along its length, or is otherwise not acceptable, then the electrophysiologist can continue the procedure and correct the deficiencies in the ablation.

A gap formed along the length of the lesion will prevent the distal blood pool from assuming the desired, lessened perturbation condition and thus, once the electrophysiologist reevaluates and locates the gap or other deficiency, the electrophysiologist can correct such deficiency. After such correction, the electrophysiologist can compare the real-time image which will allow visual confirmation of the desired isolation of the target tissue (pulmonary vein) as represented by the reduced perturbation (placid) condition of the distal blood pool.

The feedback presented to the electrophysiologist can also include other qualitative information such as a calculated degree of change in the perturbation of the distal blood pool and other information that can be displayed at the same time that the real-time image of the target site is displayed. It will be appreciated that the electrophysiologist uses all of the information provided to him/her, including the information concerning the degree of perturbation of the distal blood pool and other visual information concerning the quality/sufficiency of the ablation (i.e., visual information that indicated a gap or break in the ablation (lesion)). The user can then use other means for assessing the location of the gap(s) in the lesion to allow for corrective action to be taken.

U.S. patent application publication No. 2009/0326320 discloses other details of exemplary imaging systems that can be implemented, at least in part, and is hereby incorporated by reference in its entirety. It will be understood that one or more of the features disclosed in that document can be implemented in the imaging system of the present invention in that the imaging system can include more than one means for visualizing the treatment site and providing the user (electrophysiologist) with helpful feedback and information concerning the quality of the lesion (i.e., whether the lesion is a continuous, uninterrupted structure, etc.).

Modular Motor Unit for Handle

In accordance with one embodiment of the present the ablation device is motorized so as to allow motorized control over the movement of the ablation element. More specifically, FIGS. 16-29, depict another embodiment of the present invention in which an ablation instrument (device) 1000 is provided. The ablation instrument 1000 is similar to the ablation instrument 100 and includes many of the features described hereinbefore with reference to ablation instrument 100. Generally, the ablation instrument 1000 includes an elongated handle (body) 1010 that has a proximal end 1012 and an opposing distal end 1014. As shown in the figures, the handle 1010 can be formed of two separate halves, namely, a first half or top (upper) handle portion 1100 and a second half or bottom (lower) handle portion 1200. The top and bottom handle portions 1100, 1200 together to form the assembled handle 1010. Each of the top handle portion 1100 and the bottom handle portion 1200 can be thought of as being a shell in that there is a hollow space 1101, 1201, respectively, defined therein and when the top handle portion 1100 and the bottom handle portion 1200 are assembled to one another, these hollow spaces define an at least partially enclosed interior space in which working components of the instrument 1000 are contained as described herein.

As illustrated, the distal end of the top handle portion 1100 that in part defines the distal end 1014 of the handle body 1010 is narrower than the proximal end of the top handle portion 1100 that in part defines the proximal end 1012 of the handle body 1010. For example, the distal end of the top handle portion 1100 can have a tapered construction. The top handle portion 1100 also includes an intermediate portion 1110 between the proximal and distal ends. As shown, the intermediate portion 1110 includes an opening (through hole) 1120. The opening 1120 can have any number of different shapes and/or sizes so long as the opening 1120 can allow user access for the intended purpose described herein. The illustrated opening 1120 is generally rectangular shaped.

The top handle portion 1100 is thus defined by an outer wall 1102 and a peripheral side wall 1104 that extends around the edge of the outer wall 1102. A proximal portion of the peripheral side wall 1104 can be thought of as being an end wall and is identified at 1105. The end wall 1105 includes one or more notches 1107, 1109 to allow passage of other parts into the hollow interior space 1005. The notches 1107, 1109 can be laterally spaced apart from one another and can have different shapes and/or sizes. For example, the notch 1107 can be larger than the notch 1109.

The top handle portion 1100 can include a number of integral reinforcing or support elements and/or divider elements.

As illustrated, the distal end of the bottom handle portion 1200 that in part defines the distal end 1014 of the handle body 1010 is narrower than the proximal end of the bottom handle portion 1200 that in part defines the proximal end 1012 of the handle body 1010. For example, the distal end of the bottom handle portion 1200 can have a tapered construction. The bottom handle portion 1200 also includes an intermediate portion 1210 between the proximal and distal ends. As shown, the intermediate portion 1210 includes an opening (through hole) 1220. The opening 1220 can have any number of different shapes and/or sizes so long as the opening 1220 can allow user access for the intended purpose described herein. The openings 1120, 1220 are formed in their respective handle portions 1100, 1200, respectively, such that they overlie one another when the top and bottom handle portions 1100, 1200 are assembled to one another. As discussed herein, this through hole or window defined by the openings 1120, 1220 provides access to a controller that allows for controlled movement of the ablation element.

The bottom handle portion 1200 is thus defined by an outer wall 1202 and a peripheral side wall 1204 that extends around the edge of the outer wall 1202. A proximal portion of the peripheral side wall 1204 can be thought of as being an end wall and is identified at 1205. The end wall 1205 includes one or more notches 1209 to allow passage of other parts into the hollow interior space 1005. When there is more than one notch, the notches 1209 can be laterally spaced apart from one another and can have different shapes and/or sizes.

The bottom handle portion 1200 includes a tubular extension 1230 that extends outwardly from the proximal end of the bottom handle portion 1200. The tubular extension 1230 can thus be located along one side of the bottom handle portion 1200. As shown, the tubular extension 1230 can be in the form of a cylindrically shaped structure that has a hollow interior 1231. The end wall 1205 is thus formed so as to accommodate the tubular extension 1230 and provide communication between the hollow interior space of the bottom handle portion 1200 and the hollow interior of the tubular extension 1230. As described herein, the tubular extension 1230 is configured to receive and removably hold a motor unit 1300.

As with the ablation instrument 100, the ablation instrument 1000 includes an inflatable balloon (e.g., compliant balloon) and an energy emitter (e.g., fiber optic) that is movably disposed within the inflatable balloon. In particular, the inflatable balloon is coupled to the distal end 1012 of the housing 1010. As described in more detail herein, the energy emitter can move both in an axial direction and a rotational direction with the two motions being independent from one another. Thus, the energy emitter can be moved axially in a distal/proximal direction and the energy emitter can be rotated to change a rotational position of the energy emitter.

In order to control both the axial movement and the rotation of the energy emitter, an actuator 1045 is provided and is directly coupled to the energy emitter (e.g., fiber optic) so that manipulation of the actuator 1045 is directly translated into movement of the energy emitter. In the illustrated embodiment, the actuator 1045 can be in the form of a knob. The knob 1045 is contained within the open space (window) defined by the openings 1120, 1220 and can be ribbed to allow the user to easily grip, hold and manipulate the knob 1045.

The degree of travel of the knob 1045 is limited by the ends of the openings 1120, 1220 in that the knob 1045 can only travel between one end of the openings 1120, 1220 to the other end of the openings 1120, 1220. This movement between the ends of the openings 1120, 1220 is in the axial direction and thus, when the knob 1045 moves axially toward the distal end of the openings 1120, 1220, the energy emitter is likewise translated in the distal direction and similarly, when the knob 1045 moves axially toward the proximal end of the openings 1120, 1220, the energy emitter 1040 is likewise translated in the proximal direction. In addition, when the knob 1045 is rotated within the openings 1120, 1220, this motion is directly translated into controlled rotation of the energy emitter.

The user can thus independently move the energy emitter axially within the inflatable balloon by moving the knob 1045 in either a distal or proximal direction within the openings 1120, 1220 and can rotate the energy emitter within the inflatable balloon by rotating the knob 1045. For example, when the user wishes to move the energy emitter in a distal direction within the balloon and wishes to change the degree of emission of the energy, the knob 1045 is moved distally and then is rotated a select number of degrees.

When the energy emitter is in the form of an optical fiber (FIG. 27), the knob 1045 is attached or otherwise coupled (e.g., indirectly) to the optical fiber. As shown in the figures, the knob 1045 is attached to a stem (outer jacket) 1047, which can have a tubular shape, such that movement of the knob 1045 is translated into movement of the stem 1047 (both in an axial direction and a rotational direction).

As discussed herein, the fiber optic is surrounded by a torsionally stiff torque tube (in the figures, the reference character 1049 represents a combined fiber optic and torque tube) and thus, when the fiber optic is described herein, it will be appreciated that the physical fiber optic is preferably surrounded by the torque tube. The fiber optic can be attached to the torque tube 1049 at its distal end (this attachment can be accomplished using traditional techniques such as bonding, etc.

The stem 1047 can be formed of any number of different materials, including but not limited to metals and plastics.

Figure 27:
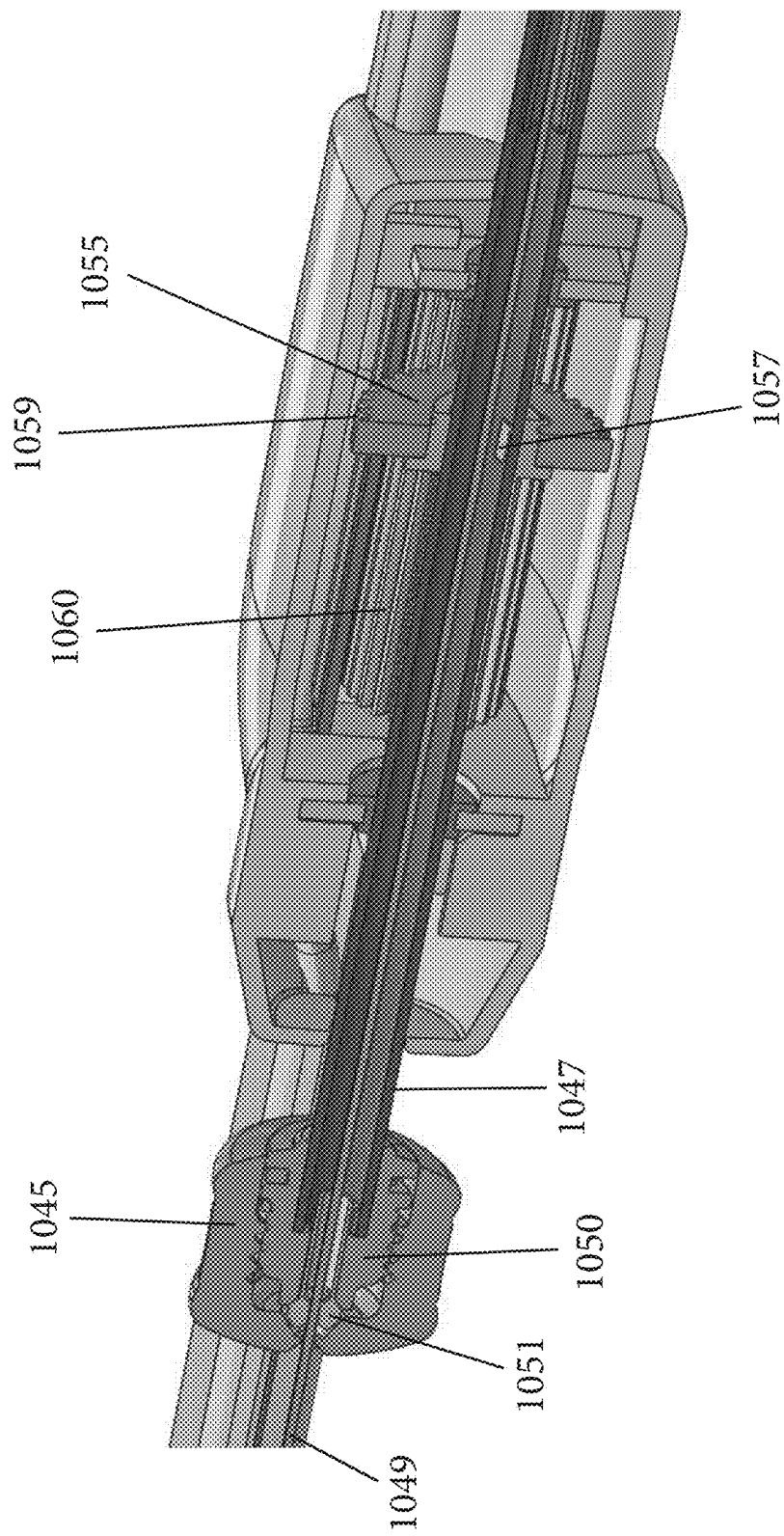
FIG. 27 is a cross-sectional view of an actuator and stem.
Figure 28:
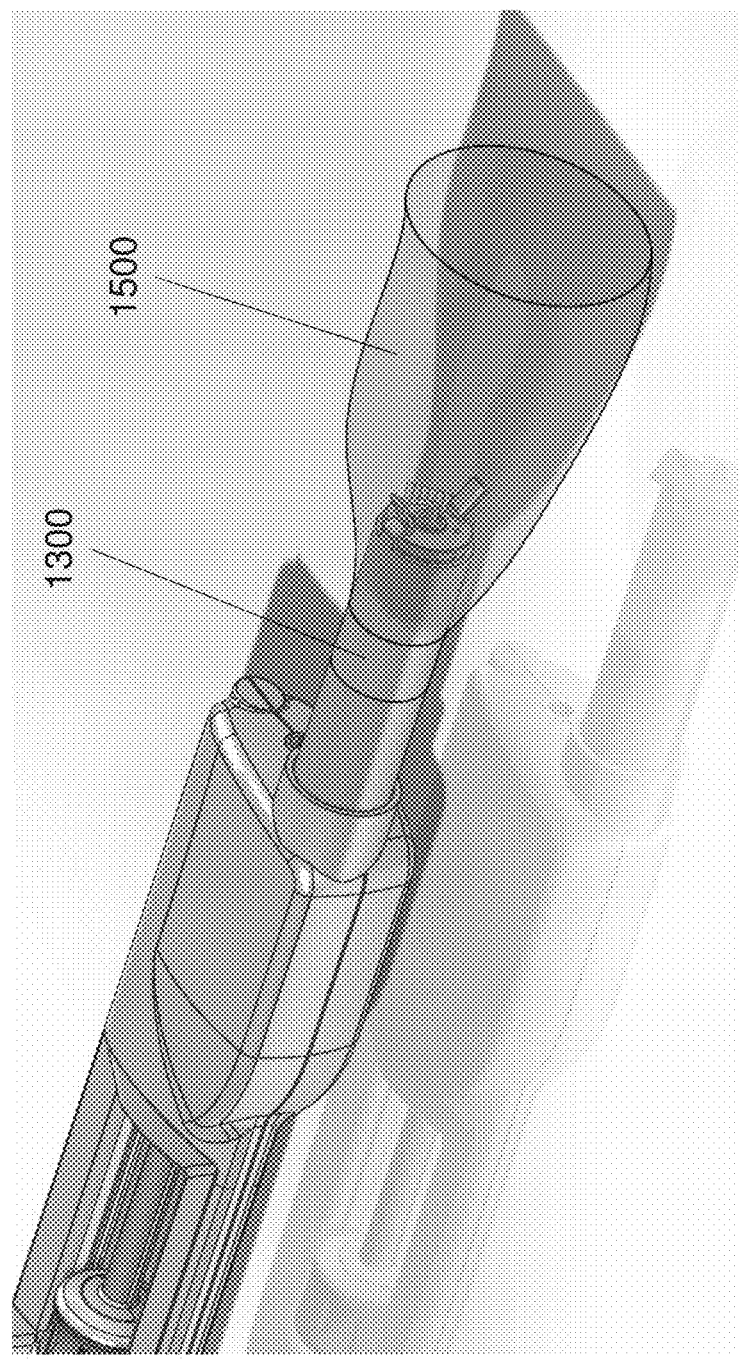
FIG. 28 is a perspective view of the motor with a protective sterilized sheath over the motor.
Figure 29:
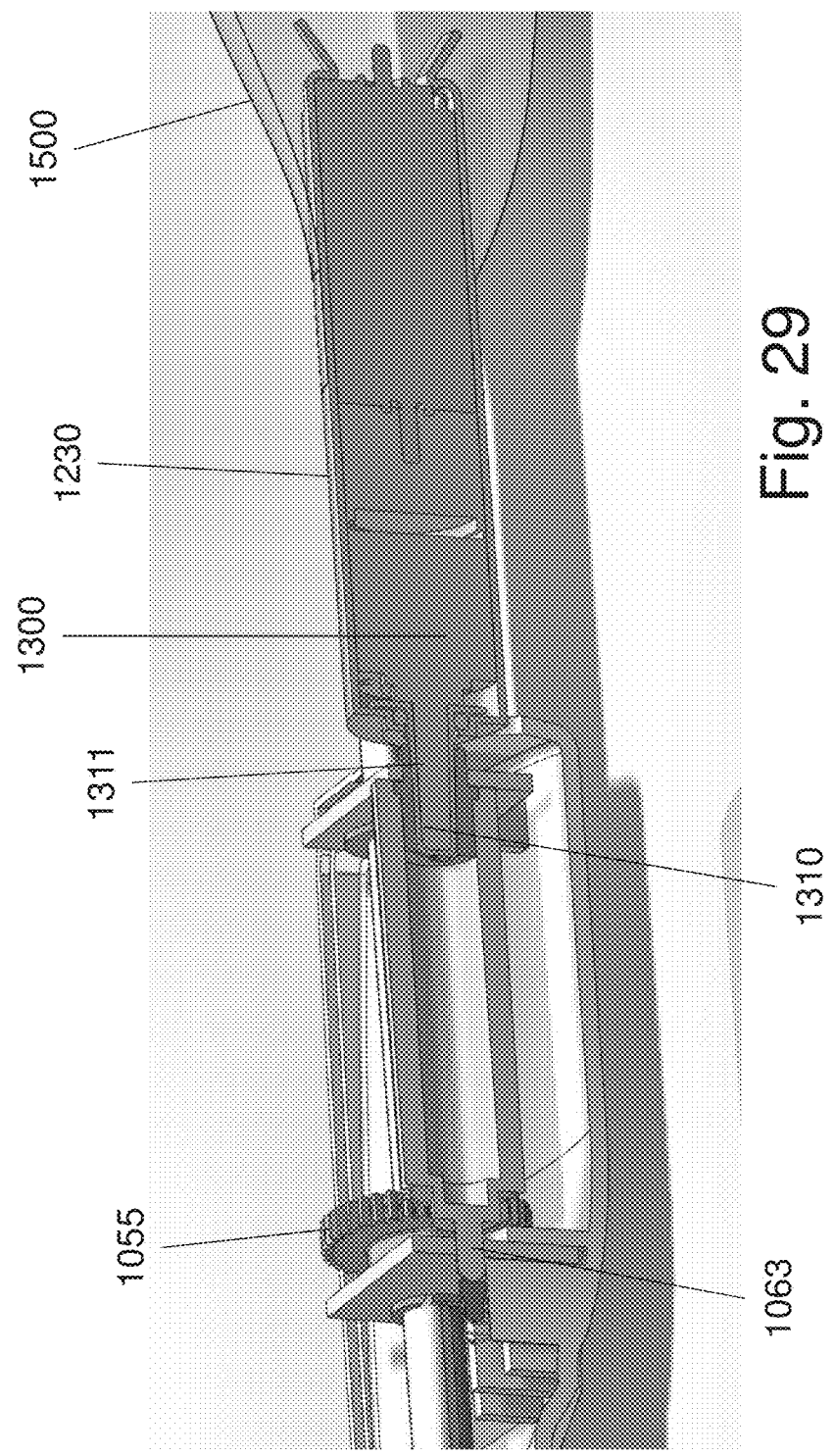
FIG. 29 is a perspective cross-sectional view of protective sterilized sheath and motor.

As shown in FIG. 27, the stem 1047 includes a lumen through which the fiber optic and the torsionally stiff torque tube 1049 can be routed. A distal end of the stem 1047 can be coupled the knob 1045, while a proximal end of the stem 1047 can protrude beyond the proximal end 1012 of the housing 1010. The torsionally stiff torque tube 1049 can thus be in the form of a rod or sheath that surrounds the fiber optic. As will be understood, the fiber optic extends from the proximal end 1012 of the housing 1010 and is operatively connected to the main controller (main control unit). The fiber optic and the torsionally stiff torque tube 1049 thus passes through the knob 1045.

As shown in FIG. 27 and according to one embodiment, a first connector 1050 can be provided and is attached to the distal end of the stem 1047 using any number of suitable techniques, including but not limited to, use of bonding agents/adhesives. The first connector 1050 can be configured to be received within a hollow interior of the knob 1045. For example, the first connector 1050 can include outer threads that mate with inner threads contained within the hollow interior of the knob 1045. The first connector 1050 has a through hole formed therein to allow for passage of the fiber optic and the torsionally stiff torque tube 1049.

A keyed type connection can be formed between the stem 1047 and the first connector 1050 to form a secure connection therebetween and prevent the stem 1047 from slipping relative to the first connector 1050.

FIG. 27 illustrates an embodiment in which a collet 1051 is provided and surrounds the fiber optic 1049 (torque tube) and is designed to pinch the fiber optic (torque tube) when a force is applied to the collet (the torque tube can be formed of nitinol or similar material). The collet 1051 is a slotted structure such that when a tightening force is applied thereto, the collet 1051 exerts a clamping force on the torsionally stiff torque tube 1049 when the collet 1051 is tightened. In particular, the surrounding knob 1045 is tightened, the collet 1051 tightens onto the torque tube 1049 that carries the fiber optic. The slots formed in the collet 1051 facilitates the tightening down of the collet 1051.

Spline Gear Configuration

Along a length of the stem 1047, a first gear 1055 is provided and is fixedly attached to the stem 1047. The first gear 1055 thus extends about the stem 1047 and since the first gear 1055 is fixedly attached to the stem 1047, a driving rotation of the first gear 1055 is translated into rotation of the stem 1047 and the fiber optic 1049 for that matter.

The attachment between the stem 1047 and the first gear 1055 can be made with a gear hub 1057 to which the stem 1047 is fixedly attached, as by bonding. The gear hub 1057 thus extends about (surrounds) the stem 1047. A keyed type connection can be formed between the stem 1047 and the gear hub 1057 to form a secure connection therebetween and prevent the stem 1047 from slipping relative to the gear hub 1057. The first gear 1055 includes teeth 1059 that extend about the periphery thereof. As shown, the first gear 1055 has a circular shape.

The stem 1047 extends longitudinally within the housing 1010 and the first gear 1055 is disposed within the proximal end section of the housing 1010. As mentioned previously, the top and bottom handle portions 1100, 1200 include internal supports that can be used to position and hold the stem 1047 in place, while permitting rotation of the stem 1047.

In one embodiment, a second gear 1060 is provided and is configured to mesh with the first gear 1055 and therefore includes teeth 1061 that mesh with teeth 1059. The second gear 1060 can be in the form of a spline gear that has a length that is substantially longer than the first gear 1055. This difference in lengths between the gears 1055, 1060 permits the first gear 1055 to axially move relative to the fixed second gear 1060 while still remaining in meshed connection therewith. This gear arrangement allows for the axial movement of the stem 1047 and knob 1045 when the user axially moves the energy emitter 1040. In other words, the first gear 1055 can slide in an axial direction along the teeth 1061 while the respective teeth 1059, 1061 remain intermeshed so as to allow rotation of the second gear 1060 is translated into rotation of the first gear 1055.

Figure 18:
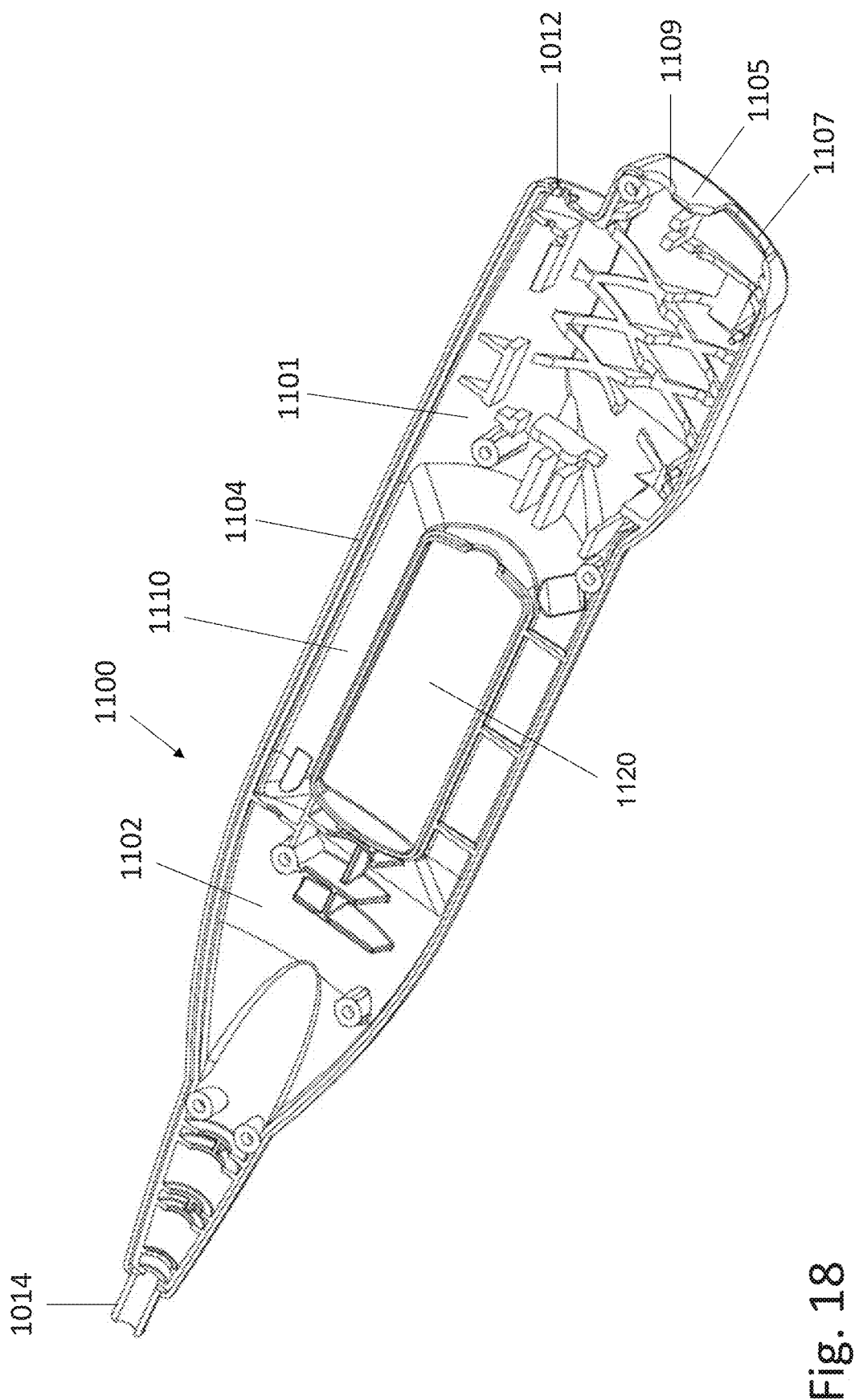
FIG. 18 is a perspective view of a top handle housing part.

The second gear 1060 is thus positioned in the proximal end of the housing 1010 and is positioned along an axis that is parallel to the axis of the stem 1047 and the first gear 1055. The second gear 1060 is also held in place by one or more supports that form part of at least one of the top handle portion 1100 and the bottom handle portion 1200. For example, as shown in FIG. 18, a first support 1072 is formed along the top housing 1100 and is contoured to allow the stem 1047 and a first shaft 1063 of the second gear 1060 to pass. The first support 1072 thus limits the lateral movement of the stem 1047 and the first shaft 1063 and thus, restricts lateral movement of the first gear 1055 and the second gear 1060. The first shaft 1063 thus faces the distal end 1014 of the housing 1010. At the opposite end of the second gear 1060, a second shaft or adapter, such as adapter 1311, can be provided. Similar to the first support 1072, a second support 1074 (FIG. 17) is provided and can extend across a width of the housing 1010 at a location proximate the end wall of each of the top handle portion 1100 and the second handle portion 1200. The second support 1074 also includes a pair of openings through which the stem 1047 and the adapter 1311 of the second gear 1060 pass. The second support 1074 thus limits the lateral movement of the stem 1047 and the adapter 1311 and thus, restricts lateral movement of the first gear 1055 and the second gear 1060.

In addition, there can be a pair of bearing plates that are not positively attached to any structure. More particularly, the bearing plates are floating plates that are sandwiched between the top handle portion 1100 and the bottom handle portion 1200 which serves to hold the first support 1072 and the second support 1074 in place (similar to a guillotine). The bearing plates are spaced from one another in a longitudinal direction and each of the first and second bearings are thus disposed within a receiving slot formed between a pair of walls (such as walls 1072, 1074) that serves to locate each of these bearing plates. The second gear 1060 is thus disposed between the two bearing plates.

Figure 20:
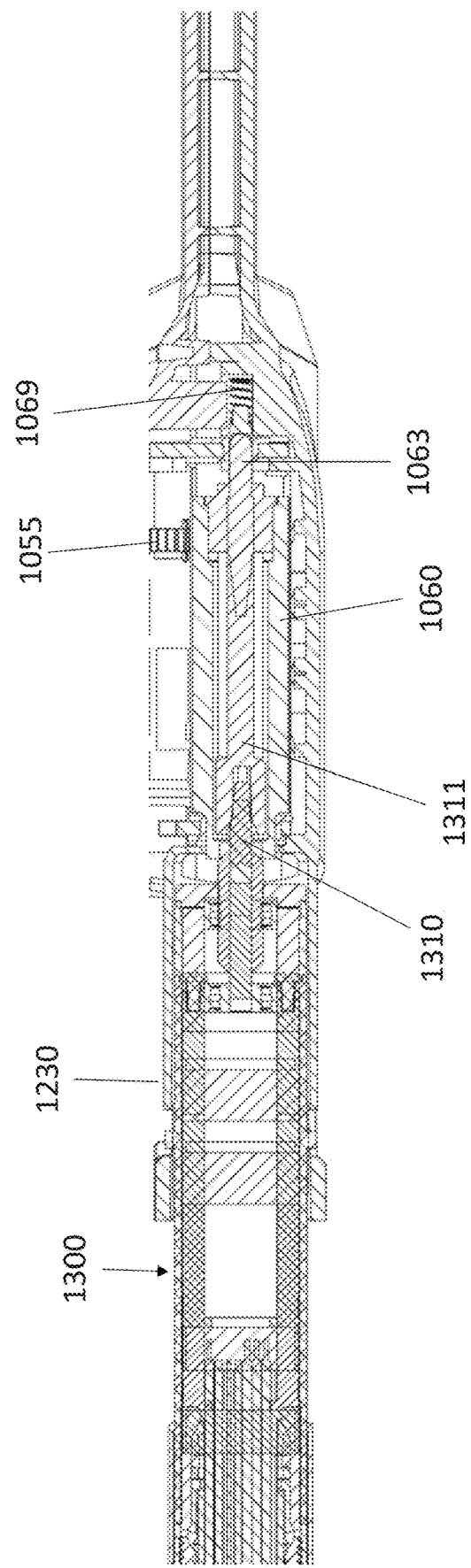
FIG. 20 is a cross-sectional view of the motor and drive and gear assembly.

With reference to FIG. 20, the second gear 1060 can be a spring loaded (biased) structure in that a biasing element 1069, such as a spring, can be disposed adjacent the first shaft 1063 and a support wall associated with the housing. The spring 1069 is thus disposed between the first shaft 1063 and the support wall and thus applies a biasing force to the second gear 1060 in a direction toward the motor unit. This ensures that the second gear 1060 remains engages with the motor unit. As shown, a pin can be installed on the spring.

As shown, the adapter 1311 is disposed at least partially within the hollow interior of the second gear body. The adapter 1311 is configured to mate with the modular motor unit 1300 (e.g., in a keyed manner) such that the two are directly coupled to one another and operation of the motor unit 1300 causes controlled rotation of the second gear 1060. Any number of different types of connections can be formed between the motor unit 1300 and the second gear 1060 and more particularly, the motor unit 1300 includes a driven main shaft 1310 that is configured to mate with adapter 1311 of the second gear 1060. For example, a keyed connection can be formed therebetween.

In one embodiment, the sleeve (adaptor) 1311 can have a shape, such as a hexagon, and represents a socket that receives the complementary shaped distal tip of the main shaft 1310. To couple the motor unit 1300 with the second gear 1060, the motor unit 1300 is inserted into the hollow interior of the tubular extension 1230 and is pushed forward until the main shaft 1310 is received within the socket. The tubular extension 1230 thus surrounds at least a portion of the motor unit 1300 and therefore protects the motor unit 1300 and prevents the user from accessing the rotating main shaft 1310.

The motor unit 1300 can be coupled and secured within the tubular extension 1230 using any number of different means including but not limited to using a bayonet type connection (mount). As shown, the tubular extension 1230 can include slot that has a receiving end and a locking end. The motor unit 1300 has a complementary protrusion (pin) that is received within the slot and is manipulated within the slot and rotated to cause the pin to move to the locking end of the slot.

Sliding Splined Gear Arrangement

Figure 21:
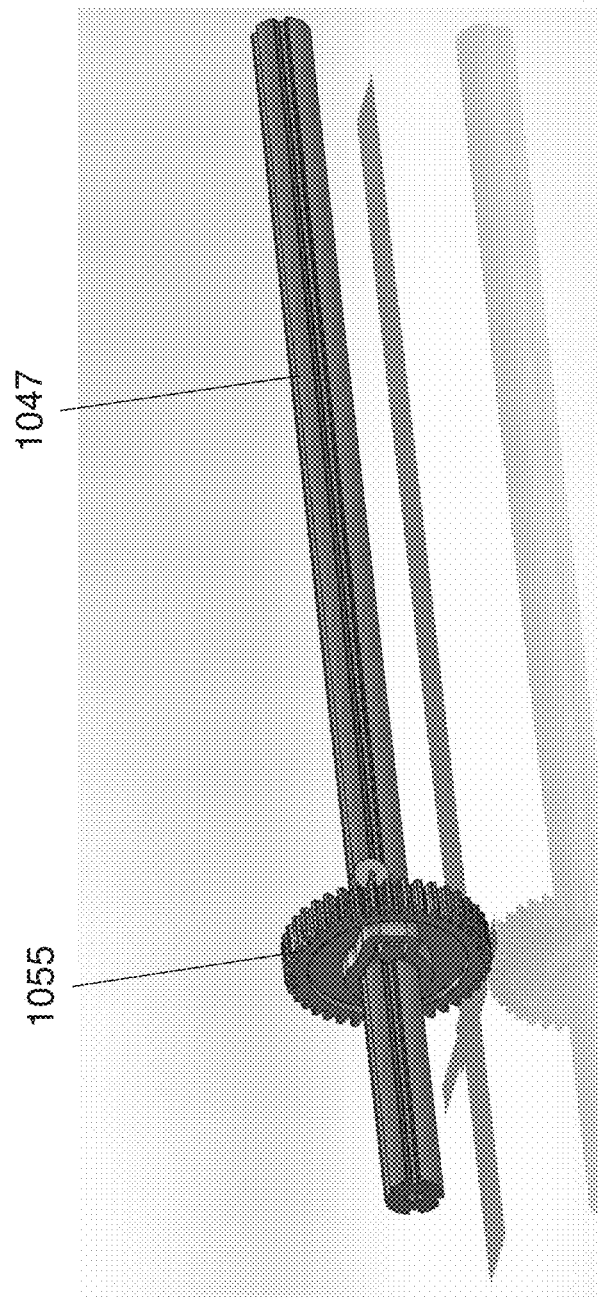
FIG. 21 is a perspective view of a sliding preloaded splined gear and stem.

As shown in FIG. 21, in another embodiment, the second gear 1060 (FIG. 19) is a fixed gear and the first gear 1055 is slidingly coupled to the stem 1047 such that the stem 1047 can move axially with respect to the first gear 1055 which remains fixedly attached to the fixed second gear 1060. Thus, unlike the previous embodiment, the first gear 1055 does not move axially with the stem 1047 but instead, the stem 1047 slides axially within a center opening of the first gear 1055 which remains at least substantially fixed in the axial direction and in fixed engagement with the second gear 1060. For example, the first gear 1055 can include a plurality of ball bearings that are located at least partially within the center opening of the first gear 1055 and can rotate therein. The center opening is thus not a perfect circle due to the presence of the ball bearings and thus, instead it can be thought of as being a keyed opening. For example, there can be four sets of ball bearings that define four protrusions that extend into the center opening. In this embodiment, the stem 1047 can be a slotted shaft that is configured to receive the protrusions (defined by the ball bearing sets). In other words, when there are four protrusions, the stem 1047 has four axially (longitudinally) extending slots (channels), with one protrusion being received with one of the corresponding slots. The ball bearings thus promote axially movement of the stem 1047 relative to the fixed first gear 1055. In other words, when the user axially moves the stem 1047, the stem 1047 rolls over the ball bearings.

However, the keyed coupling between the stem 1047 and the first gear 1055 prevents the first gear from rotating relative to the stem 1047. Thus, when the first gear 1055 is rotatably driven by the second gear 1060, not only does the first gear 1055 rotate but also the stem 1047, resulting in controlled rotation of the ablation element coupled to the stem 1047. In this embodiment, the second gear 1060 can be a smaller gear in that it does not have the extended length that the spline gear 1060 of the previous embodiment since in that embodiment, the first gear 1055 rides axially along the extended length of the second gear 1060.

It will also be understood that the ball bearings of the second gear 1060 can be biased (spring biased) within the second gear 1060 so to ensure that the ball bearings are placed with and maintained in contact with the stem 1047.

Roller Splined Gear Arrangement

Figure 19:
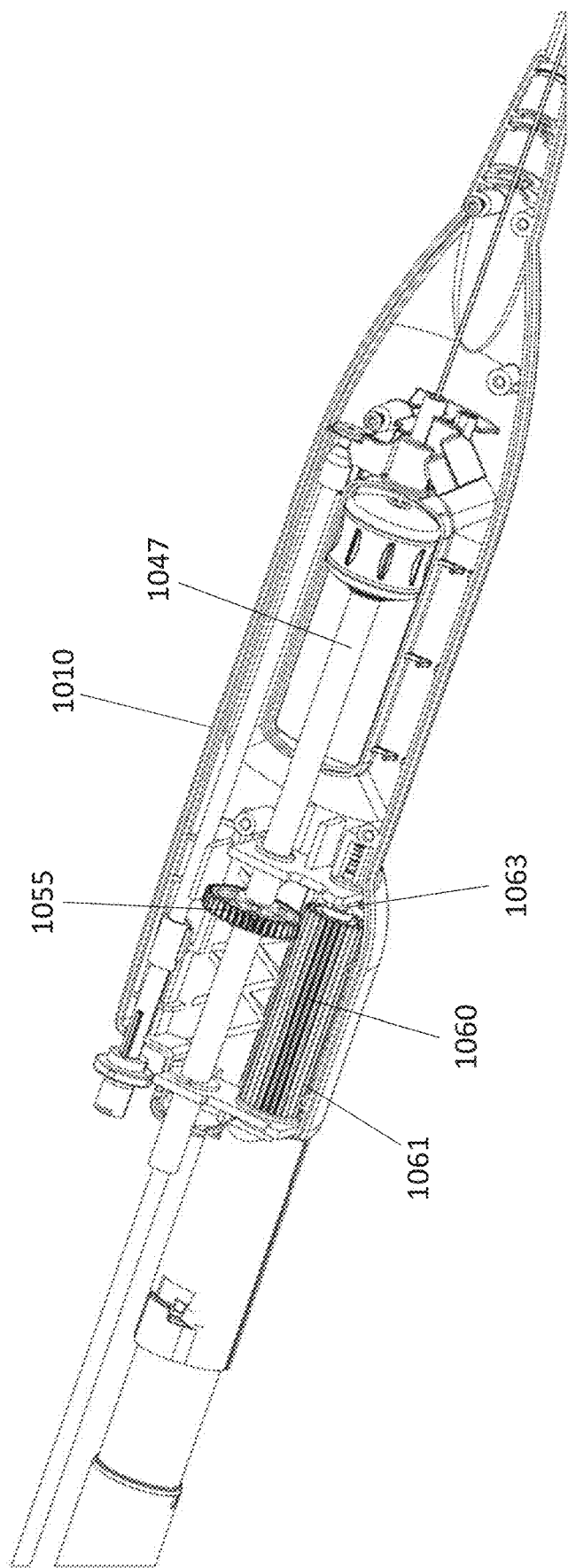
FIG. 19 is a perspective view of a portion of the handle housing with a gear arrangement according to a first embodiment.
Figure 22:
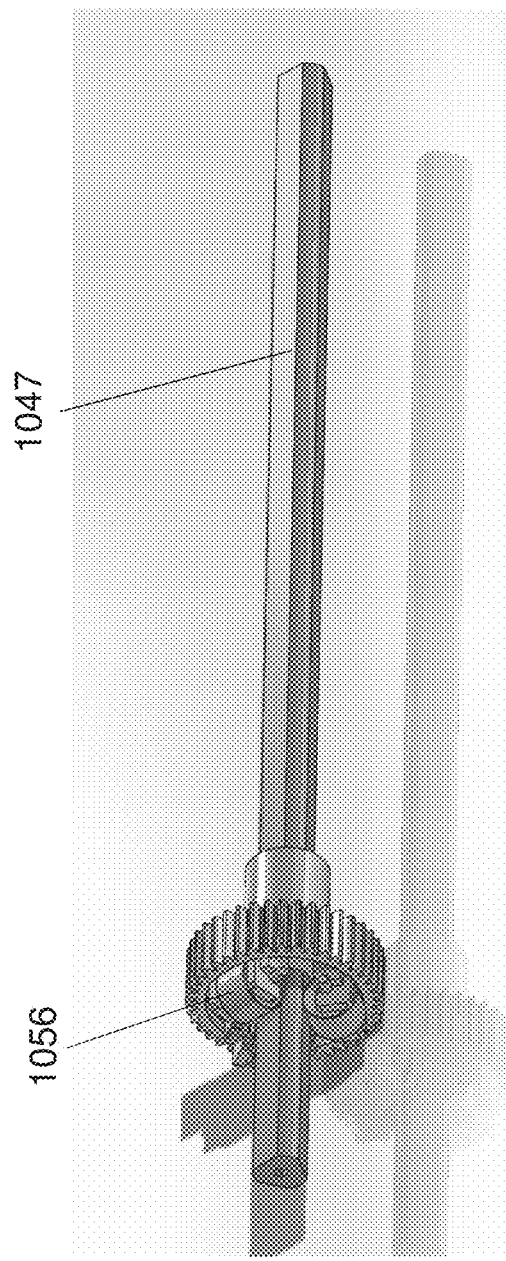
FIG. 22 is a roller splined gear with stem.
Figure 23:
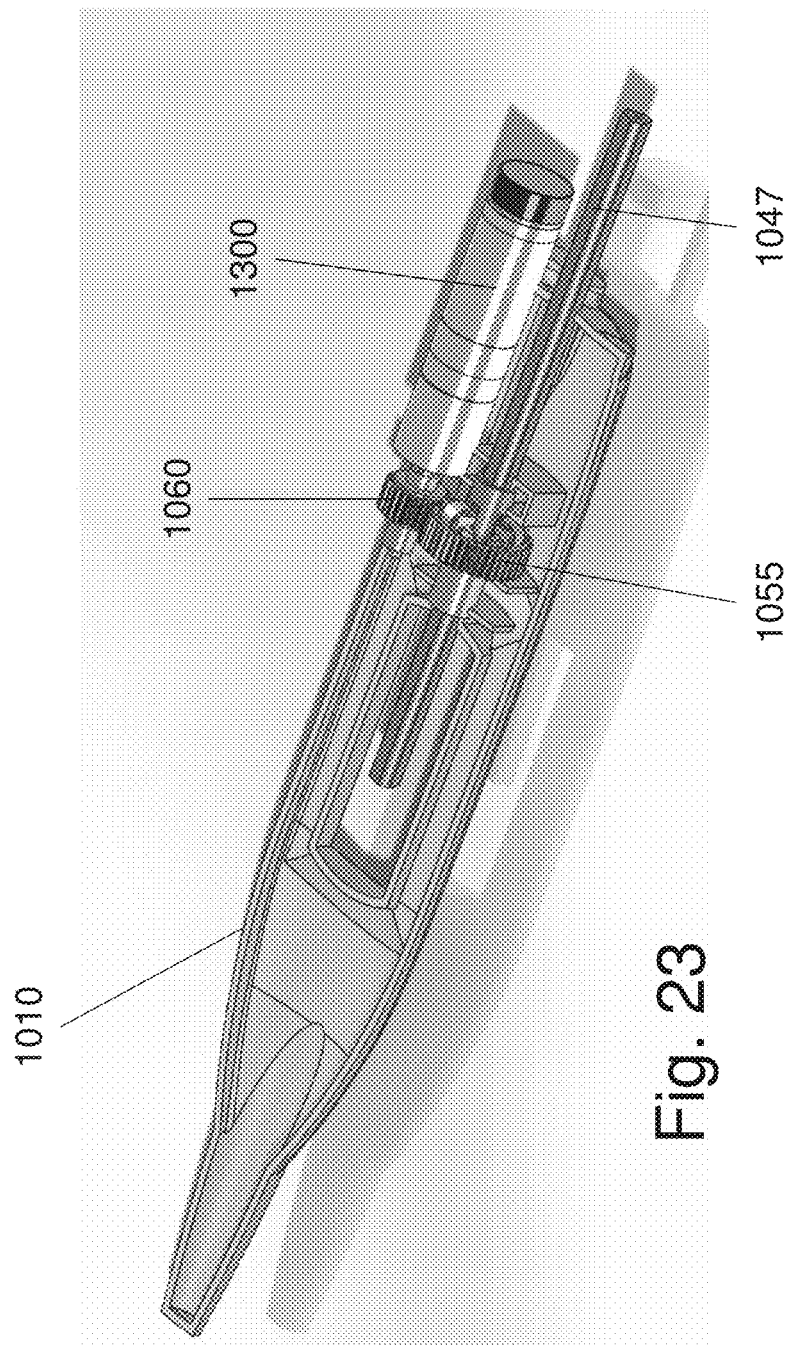
FIG. 23 is a perspective view of the roller gear and motor installed into the housing.
Figure 24:
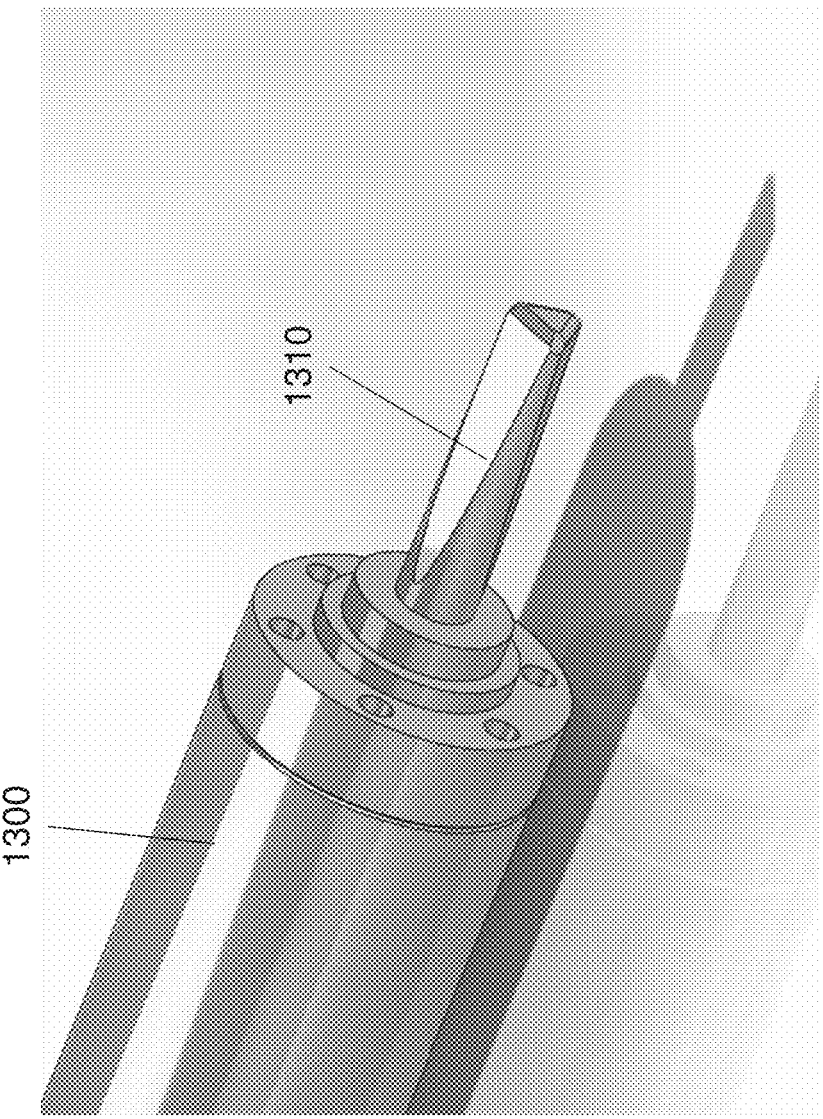
FIG. 24 is a perspective view of a portion of the motor with drive shaft.

As shown in FIG. 22, in another embodiment, the second gear 1060 is a fixed gear and the first gear 1055 is slidingly coupled to the stem 1047 such that the stem 1047 can move axially with respect to the first gear 1055 which remains fixedly attached to the fixed second gear 1060 (FIG. 19). This embodiment is similar to the previous ball bearing arrangement; however, instead of using pairs of ball bearings, the first gear 1055 has a plurality of rollers 1056. For example, the second gear can have an annular shape and the rollers 1056 are located within the hollow center. The body of the first gear 1055 can include a body structure to which the rollers 1056 are rotatably coupled. Each roller 1056 can include a shaft which is rotatably coupled to the body structure. For example, there can be three rollers 1056 spaced equidistant (e.g., 120 degrees apart from one another). As with the previous embodiment, the rollers 1056 permit the stem 1047 to axially move relative to the first gear 1055 which remains in a relatively fixed position due to it being intermeshingly coupled to the second gear 1060.

It will be understood that the stem (also can be referred to as a shaft or outer jacket) 1047 includes a plurality of flat portions that extend axially along the length of the stem 1047 and the rollers 1056 seat on and are in contact with these flat portions to allow the stem 1047 to freely move axially within the first gear 1055 due to the flat portions riding along and causing rotation of the rollers when the stem 1047 is moved axially as by axial movement of the knob 1045.

Tube Guard

As described herein, the ablation instrument 1000 is intended to be operatively connected to a control unit that includes one or more pumps for circulating fluid(s) to and from the ablation instrument 1000 and also includes other controls for one or more light sources and for the ablation element itself. As a result, a number of tubes are routed within the hollow interior space of the housing 1010. In particular, one or more tubes can be routed within the housing 1010 in a first direction (toward the proximal end 1012 of the housing 1010) and along one side of the housing 1010 and along the opposite side of the housing 1010 in the opposite second direction. Since there are a number of working/moving components within the housing 1010, there is a need to isolate and protect these tubes from the moving components.

Figure 25:
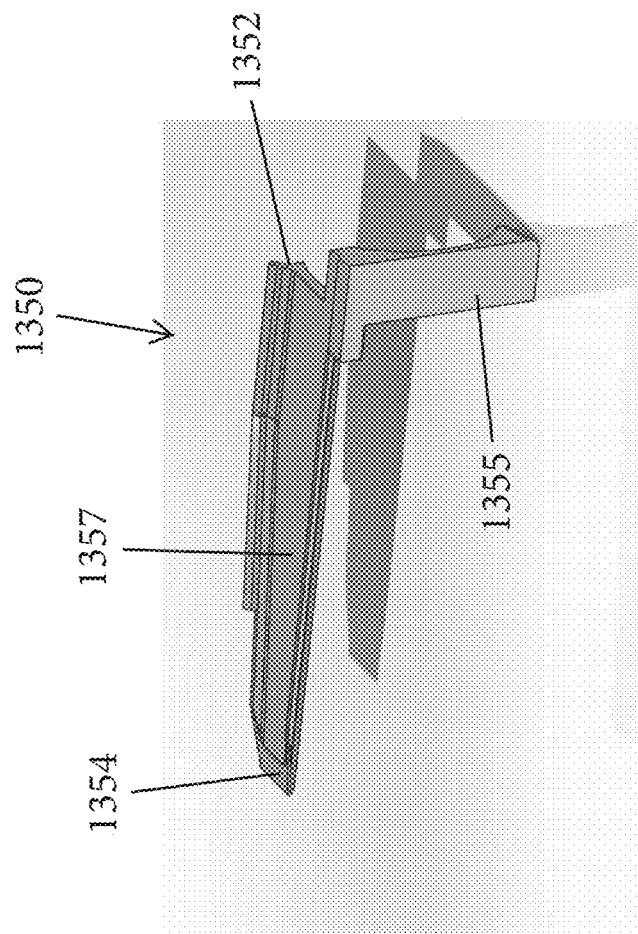
FIG. 25 is a perspective view of a tube guard.
Figure 26:
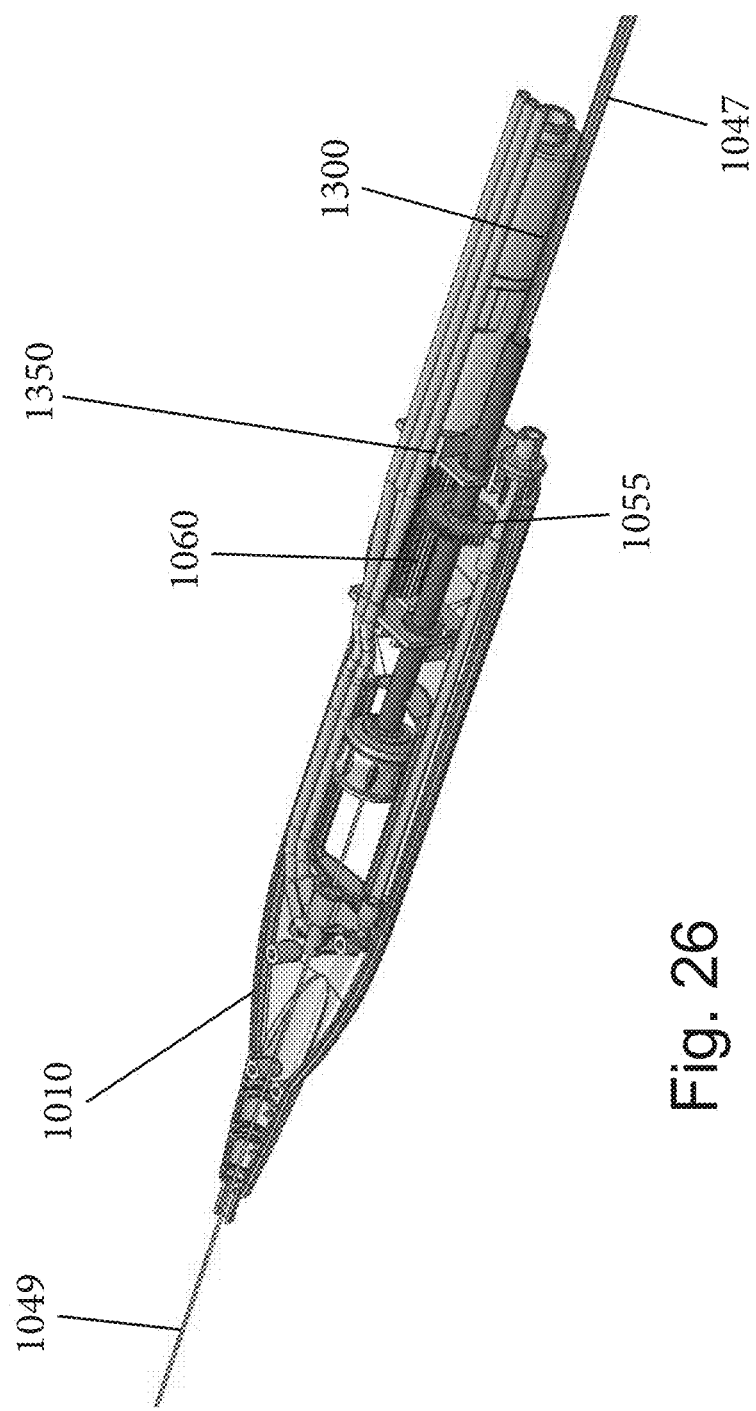
FIG. 26 is a perspective view of the tube guard installed above the gears.

As shown in FIGS. 25-26, a tube guard 1350 is shown and is mounted within the hollow interior of the housing 1010. For example, the bottom handle portion 1200 can contain the tube guard 1350. The tube guard 1350 has a first end 1352 and an opposite second end 1354. The first end 1352 has a leg 1355 that depends downwardly from a track portion 1357 of the tube guard 1350. As shown, the track portion 1357 can be generally linear in shape and includes opposing raised side walls that extend upwardly from a floor of the track portion 1357. An inner surface of the leg 1355 has an arcuate shape since the leg 1355 is intended to be placed about the tubular extension 1230. As shown, the leg 1355 is placed in contact with the tubular extension 1230 near or at the distal end of the tubular extension 1230, with the track portion 1357 extending over the second gear 1060 to allow the tubing to be routed above the rotating second gear 1060.

The motor unit 1300 is preferably modular in nature and can be thought of as being a motor pack. The motor unit 1300 thus can have a cylindrical shape with a distal end and a proximal end. The distal end of the motor unit 1300 includes the driven main shaft 1310 which, as mentioned previously, can have a specific shape to allow a keyed connection with the second gear 1060 or as illustrated, the adapter 1311 can have a keyed connection with the second gear 1060. The motor unit 1300 can be formed of any number of different materials and in particular, the outer housing (casing) (cylindrical shaped) of the motor unit 1300 can be formed of a plastic, while the driven main shaft 1310 is formed of a metal.

Within the outer housing, the motor unit 1300 includes a controllable motor which is operatively coupled to the driven main shaft 1310. Any number of different types of motors can be used, including but not limited to, a stepper motor, etc. The motor unit 1300 is thus operatively connected to the main control unit to allow for control over the motor. For example, the motor can be turned on/off, the speed of the motor can be varied, the direction of rotation can be varied, etc. As will be appreciated, rotation of the driven main shaft 1310 in a first direction is translated into the energy emitter rotating in the first direction, while rotation of the driven main shaft 1310 in a second direction is translated into the energy emitter rotating in the second direction. This permits the location at which the energy is emitted to be easily varied.

The power source for the motor unit 1300 can either be a battery or it can include an electrical cable for direct connection to an electrical outlet, such as an outlet in the main controller.

Sterile Sheath for Motor Unit

Since the catheter device 1000 is intended to be used in a sterile environment (e.g., the surgical field), all components of the catheter device 1000 must be sterile. However, it will be appreciated that the motor unit (with its electronic components) is not suitable for placement in sterilization devices, such as an autoclave, etc.). A sterile sheath (bag) 1500 can be provided and configured for about the motor unit. For example, the sterile sheath 1500 can be coupled to the tubular extension and stored in a furled manner. The sterile sheath 1500 can be coupled to the tubular extension using conventional means such as taping the sterile sheath 1500 to the tubular extension or by using a rubber band or the like. The furled sterile sheath 1500 can thus be bunched up along the tubular extension and then the person in the sterile environment that is wearing sterile clothing unfurls the sheath 1500 over the motor unit. For example, a person from outside the sterile environment can present the motor unit to the sterile person in the sterile environment and in particular, this person can insert and lock the motor unit within the tubular extension 1230 as described herein. Once the motor unit is installed and locked relative to the tubular extension, the sterile actor then unfurls the sheath over the motor unit thereby encapsulating the motor unit in the sterile sheath.

It is to be appreciated that the catheter body is intended to be disposable, while the motor unit is intended to be recycled after the procedure is completed. In particular, motor unit can be used again with a new sterile ablation catheter.

It will be appreciated that the ablation catheter of the present invention is configured so that the position of the ablation element can be constantly changed over time using the motor unit and/or user involvement. As discussed herein, the user can axially move the ablation element using the knob 1045 in that axial movement of the knob 1045 within the window and this causes the axial movement of the ablation element. The controlled rotation of the ablation element is preferably caused by the controlled operation of the motor unit. Alternatively, the user, under select circumstances, can manually rotate the knob 1045 to cause rotation of the ablation element. In one embodiment, the ablation catheter can include a lockout feature that prevents the user from being able to manually rotate the knob 1045 while the motor unit 1300 is operating and is in the process of rotating the ablation element in an automated manner.

It will also be understood that the position of the ablation element is preferably based on imaging feedback that is received and viewed in real time by the user. For example, the imaging feedback can be in the form of endoscopic feedback. In other words, anatomical feedback obtained via the endoscope is used to guide the position of the ablation element and guides the future controlled movement of the ablation element.

It will also be appreciated that a second motor unit could be provided to allow for controlled axial movement of the energy emitter. In particular, the first shaft to which the energy emitter is coupled can be coupled to the second motor unit such that operation of the first motor causes controlled axial movement of the first shaft and thus, the energy emitter.

Figure 30:
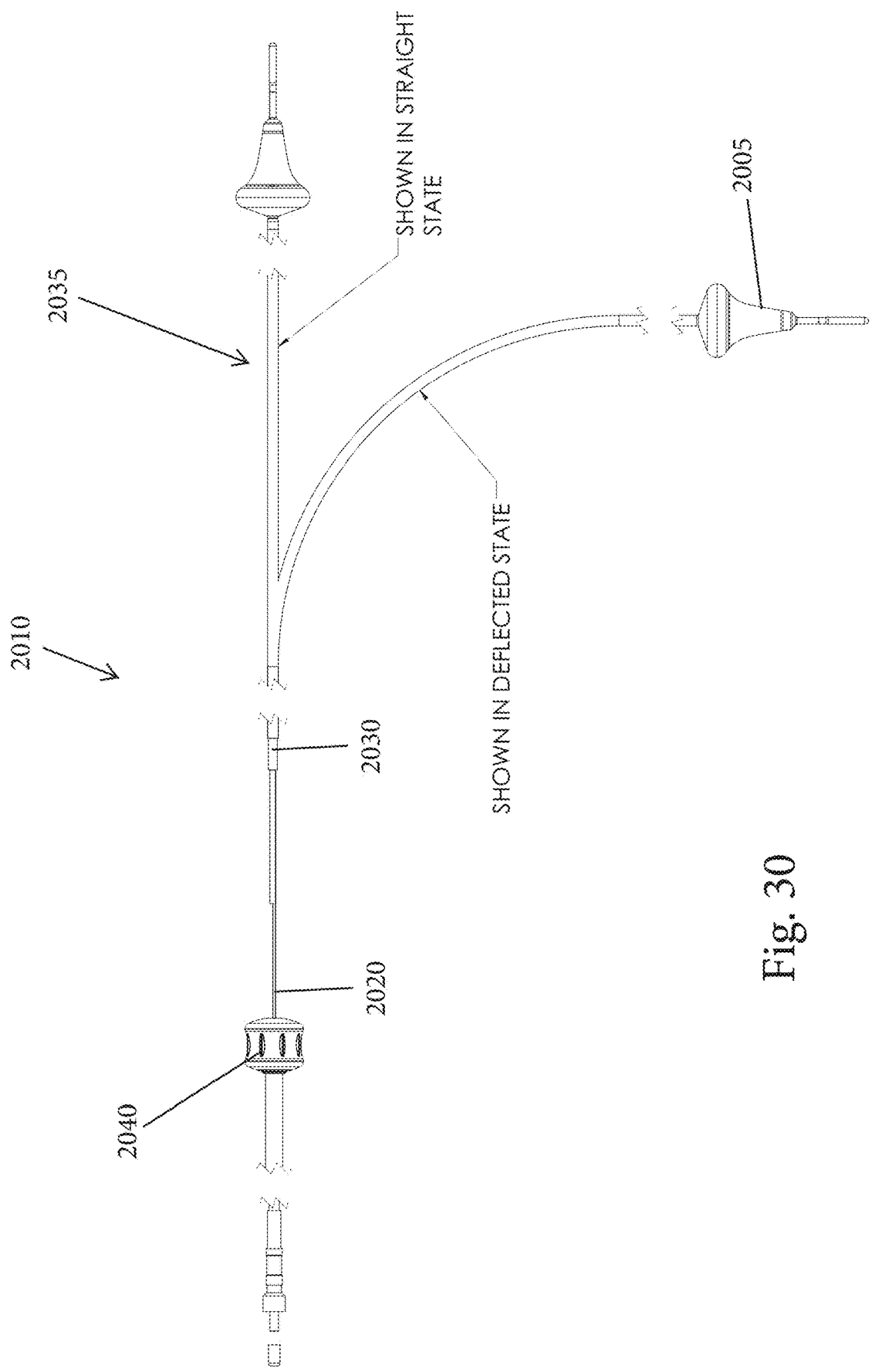
FIG. 30 is a partial side elevation view of a distal portion of a cardiac ablation device according to another embodiment and with improved rotational control over the cardiac ablation device.

FIG. 30 shows a distal portion 2010 of a cardiac ablation device (balloon catheter) 2000 similar to those disclosed herein and therefore, the device 2000 includes similar or identical elements as those other devices disclosed hereinbefore. The device 2000 includes a lesion generator optics package that is mounted on a distal end of a delivery fiber 2020. The delivery fiber (an energy emitter) 2020 is threaded through and is attached to a nitinol tube (outer jacket or sheath) 2030. The delivery fiber 2020 is attached to the distal end of the nitinol tube 2030 and extends a predetermined distance, such as about 9 cm to about 10 cm, distal to the distal end of the nitinol tube 2030. A control knob 2040 is attached to or close to the proximal end of the nitinol tube 2030 and is located in the catheter handle. For ease of illustration, the catheter handle is not shown in FIG. 30. As discussed herein, the control knob enables the physician to slide the optics package distally or proximally as well as rotationally within the balloon as required for the desired energy delivery location (as described herein and in commonly assigned U.S. Ser. No. 15/399,304, filed Jan. 5, 2017.

The distal portion 2010 of the balloon catheter 2000 must be able to deflect to various degrees to enable the physician to place the balloon and energy application correctly and efficiently. The nitinol tube 2030 ends proximal to the distal portion 2010 to the allow the shaft of the device 2000 to deflect more easily. FIG. 30 shows an exemplary deflection zone 2035 that is distal to the nitinol tube 2030 and extends to a proximal end of a balloon 2037 that forms a part of the device 2000. In one exemplary embodiment, the length of the deflection zone 2035 is about 9 cm. FIG. 30 also shows the device 2000 in both a linear (straight) state and a deflected (curved) state. As can be seen, the incorporation of the deflection zone 2035 allows for deflection of the distal end portion of the device 2000. The device 2000 is of a balloon catheter type and includes an inflatable balloon 2005 that houses a lesion generator that includes optics as disclosed below.

FIGS. 31 and 32 illustrate a distal end portion 2100 including a lesion generator 2110 in accordance with one exemplary embodiment of the present invention. FIG. 31 is shown in broken away format to show the various shaft segments of the distal end portion 2100. In the distal end portion 2100, the delivery fiber in the lesion generator 2110 has a protective outer jacket 2120 called the "buffer" that protects the fiber cladding 2111 and the fiber core 2113. In one embodiment, the jacket 2120 can be formed of ethylene tetrafluorethylene. The manufacturing process that deposits the buffer 2120 is such that there is only so much control over the concentricity of the buffer 2120 with respect to the core 2113 and fiber cladding 2111, which results in the delivery fiber having a "preferred" rotational orientation if the eccentricity is pronounced. It will be seen that a segment of the catheter shaft that is proximal to the distal end portion (deflection zone) defined by the buffer 2120 can be defined by a structure that surrounds the delivery fiber (cladding 2111 and core 2113) and can be formed of FEP (fluorinated ethylene propylene) heat shrink with adhesive.

FIG. 32 is a cross-sectional view showing the buffer 2120 surrounding the cladding 2111 and the core 2113.

FIGS. 33 and 34 illustrate a distal end portion 2200 including the lesion generator 2110 in accordance with another embodiment that is configured to overcome the deficiencies associated with the distal end portion 2100 shown in FIGS. 31 and 32 and more particularly, overcomes the eccentricity issue that can be imparted by the construction shown in FIGS. 31 and 32.

The distal end portion 2200 addresses the eccentricity issue by removing the buffer (jacket) 2120 from the delivery fiber in the deflection zone and replacing it with a thin walled, small diameter jacket 2220. In one embodiment, the jacket 2220 can be in the form of a PET (polyethylene terephthalate) tube that can be attached to the cladding 211 by means of an adhesive 2221. The wall thickness of the jacket 2220 is more accurately produced (manufactured) to yield a new improved "jacket" or "buffer" that has less effect on the rotation of the delivery fiber (defined by cladding 2111 and core 2113) when in use, enabling the physician to have more precise control of positioning of the lesion generator energy delivery, whereas the rotation of the (lesion generator) optics package tracks more precisely with respect to the input rotation applied to the control knob 2040. It will also be appreciated that the same improvement over control applies to the motorized mode of operation as described herein. In other words, the improved construction of the distal end portion 2220 applies equally to both manually and automated modes of operation of the optics package. It will be appreciated that the foregoing delivery fiber construction can be used in any of the devices disclosed herein and illustrated in the figures.

Figure 38:
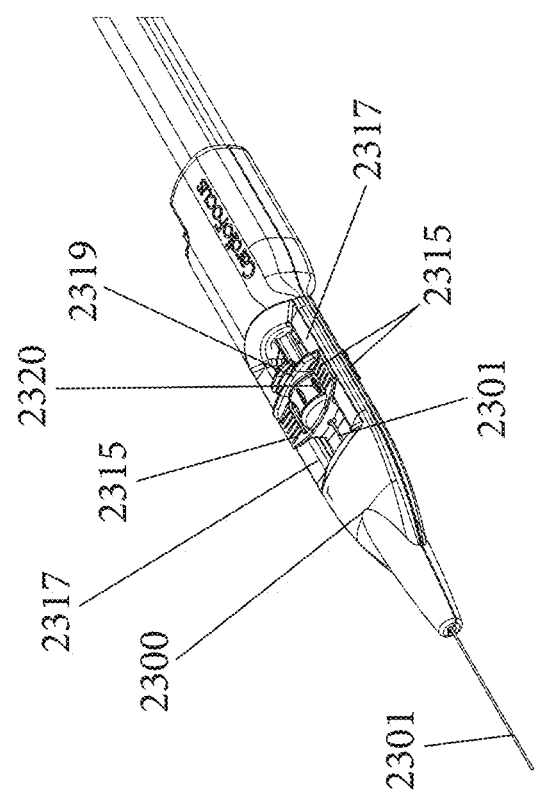
FIG. 38 is a perspective view of the catheter handle of FIG. 35 showing the sliding part surrounding the rotatable knob.

FIGS. 35-38 illustrate another aspect of the present invention in which a portion of a catheter handle 2300 is shown. As mentioned herein, the ablation device includes a movable energy emitter (ablation element (lesion generator) including optics) that is contained within a balloon and moves both longitudinally (axially) within the balloon and also is rotatable within the balloon. Thus, there is a need to provide a mechanism that allows the energy emitter to move axially without disrupting the rotation of the energy emitter. In other words, there is a need and desire to allow the energy emitter to move both axially and rotationally at the same time. FIG. 35 shows a first side elevation view; FIG. 36 is a top plan view; and FIG. 37 is a second side elevation view; and FIG. 38 is a perspective view of the portion of the catheter handle 2300.

In accordance with this embodiment, there is a sliding part (a slider) 2310 that surrounds a rotating knob 2320 that is similar or identical to the rotating knobs (e.g., knob 1045) disclosed herein and that are part of the material incorporated by reference herein. As shown, the rotating knob 2320 is contained and moves axially and rotationally within a window that is formed in the catheter handle. The rotating knob 2320 is coupled to the delivery fiber so that movement of the rotating knob 2320 is directly translated into movement of the delivery fiber (in both a longitudinal (axial) direction and rotational direction). The rotating knob 2320 thus surrounds the delivery fiber and can be a generally cylindrical shaped part that includes surface features, such as ribs or the like, that can be gripped by the user.

The sliding part 2310 is configured such that the rotational movement (motion) of the rotating knob 2320 is not impeded by the surrounding sliding part 2310. The sliding part 2310 is constructed such that it can be easily contacted by the user to axially (longitudinally) advance the rotating knob 2320 and thus, the axially move the delivery fiber (energy emitter).

As illustrated, the sliding part 2310 is contained within the window (through hole) of the catheter handle such that the two ends of the window define the ends of travel of the sliding part 2310. It will be appreciated that the ends of the window likewise define the ends of travel of the rotating knob 2320 and thus, define the degree of longitudinal movement of the energy emitter (lesion generator).

As best shown in FIG. 38, the sliding part 2310 can be formed as two parts 2330, 2231 (symmetric parts) that mate together to form a shell that surrounds the rotating knob 2320 and contains aligned holes that permit the delivery fiber 2301 to passes therethrough (the sliding part 2310 thus slides along the delivery fiber). The window is in part defined by a pair of side rails 2317 that extend longitudinally and are located opposite one another. The sliding part 2310 is configured such that it is coupled to the side rails 2317 and in particular, wing shaped sides of the sliding part 2310 slides longitudinally along the side rails 2317. The side rails 2317 thus act as guide rails for the sliding part 2310.

The sliding part 2310 includes ribs 2315 that project outward on each side of the sliding part 2310 allow the user to firmly grip the sliding part 2310 with the thumb and forefinger and hence control the longitudinal motion of the sliding part 2310 and also the longitudinal motion of the rotating knob 2320 which the sliding part 2310 surrounds. In this manner, the user can precisely control the longitudinal position of the rotating knob 2320 attached to the lesion generator without impeding the rotation motion when the rotational motion is being controlled by the motor. As discussed herein, the motor can be utilized to controllably rotate the rotating knob 2320 in order to controllably rotate the delivery fiber (energy emitter).

As illustrated, the sliding part 2310 can thus be constructed such that there is a center opening through which the rotating knob 2320 is visible and could be contacted. In particular, in the illustrated embodiment in which the sliding part 2310 is formed as a shell defined by two housing parts 2330, 2331 that mate together to form the shell, each housing part includes a center opening 2335 (FIG. 47) such that the rotating knob is accessible along each side of the handle body. Each housing part also includes a pair of side ribs 2315 with one side rib 2315 seated against one side rail 2317 and the other side rib 2315 seated against the other side rail 2317. When assembled, one pair of side ribs 2315 is disposed about one side rail 2317 with the one pair of side ribs 2315 defining a slot through which the one side rail 2317 passes to allow the sliding part 2310 to axially travel. Similarly, the other pair of side ribs 2315 is disposed about the other side rail 2317 with the other pair of side ribs 2315 defining a slot through which the other side rail 2317 passes. The side ribs 2315 thus provide a means by which the sliding part 2310 is coupled to the side rails 2317 to allow longitudinal (axial) movement of the sliding part 2310 within the window.

The sliding part 2310 can be formed such that it has a distal end portion that is located distal to the rotating knob 2320 and a proximal end portion that is located proximal to the rotating knob 2320. The sliding part 2310 can thus be in the form of a hollow shell that surrounds the rotating knob 2320 but is not directly fixed to the rotating knob 2320. Instead, the sliding part 2310 is meant to urge the rotating knob 2320 in either a forward or rearward direction within the window. The sliding part 2310 moves independent from the rotating knob 2320 and is limited to sliding along the side rails 2317 and cannot rotate. In contrast, the rotating knob 2320 is not attached to the sliding part 2310 and thus can independent move axially and rotationally. Since the rotating knob 2320 is contained (nested) within the center opening of the assembled sliding part 2310, longitudinal movement of the sliding part 2310 is translated into longitudinal movement of the rotating knob 2320 since the sliding part 2310 urges (contacts) the rotating knob 2320 in the longitudinal direction of the urging action. The urging of the rotating knob 2320 does not prevent rotation of the rotating knob 2320 since the rotating knob 2320 slides across the faces (bearing surfaces) of the sliding part 2310 even when the sliding part 2310 urges the rotating knob 2320 in the longitudinal direction.

One or more of the ribs 2315 can include surface features, such as textured lines that provide a grip feature.

As shown in FIG. 38, the sliding part 2310 also includes a rear rib 2319 that is formed at one end, namely, the proximal end of the sliding part 2310. Each housing part 2330, 2331 can include one rear rib 2319. Similar to the side ribs 2315, the rear rib 2319 can be formed as part of each of the two housing parts that assembled together form the sliding part 2310. A portion of the rear rib 2319 can be disposed at a right angle to the slide ribs 2315 and at least a portion of the rear rib 2319 projects rearwardly so as to be easily accessible to the user. More specifically, the user can grasp one or both of the side ribs 2315 and rear rib 2319 for urging (sliding) the sliding part 2310 in order to translate the rotating knob 2320 in the longitudinal direction due to the rotating knob 2320 being nested within the sliding part 2310.

Disposable Motor Embodiment

As discussed herein, in one embodiment, the ablation (balloon catheter) device can be of a type which includes a modular, reusable motor unit. However, in another embodiment, which is disclosed below, the ablation (balloon catheter) device can be constructed such that it includes a disposable motor and includes a gear arrangement similar to those described herein and shown in other figures.

FIGS. 39-48 illustrate one exemplary embodiment in which a cardiac ablation device 3000, including a motor 3001, is disposable. The cardiac ablation device 3000 is similar to the other cardiac ablation devices described and illustrated herein and therefore, like elements are numbered alike.

Figure 39:
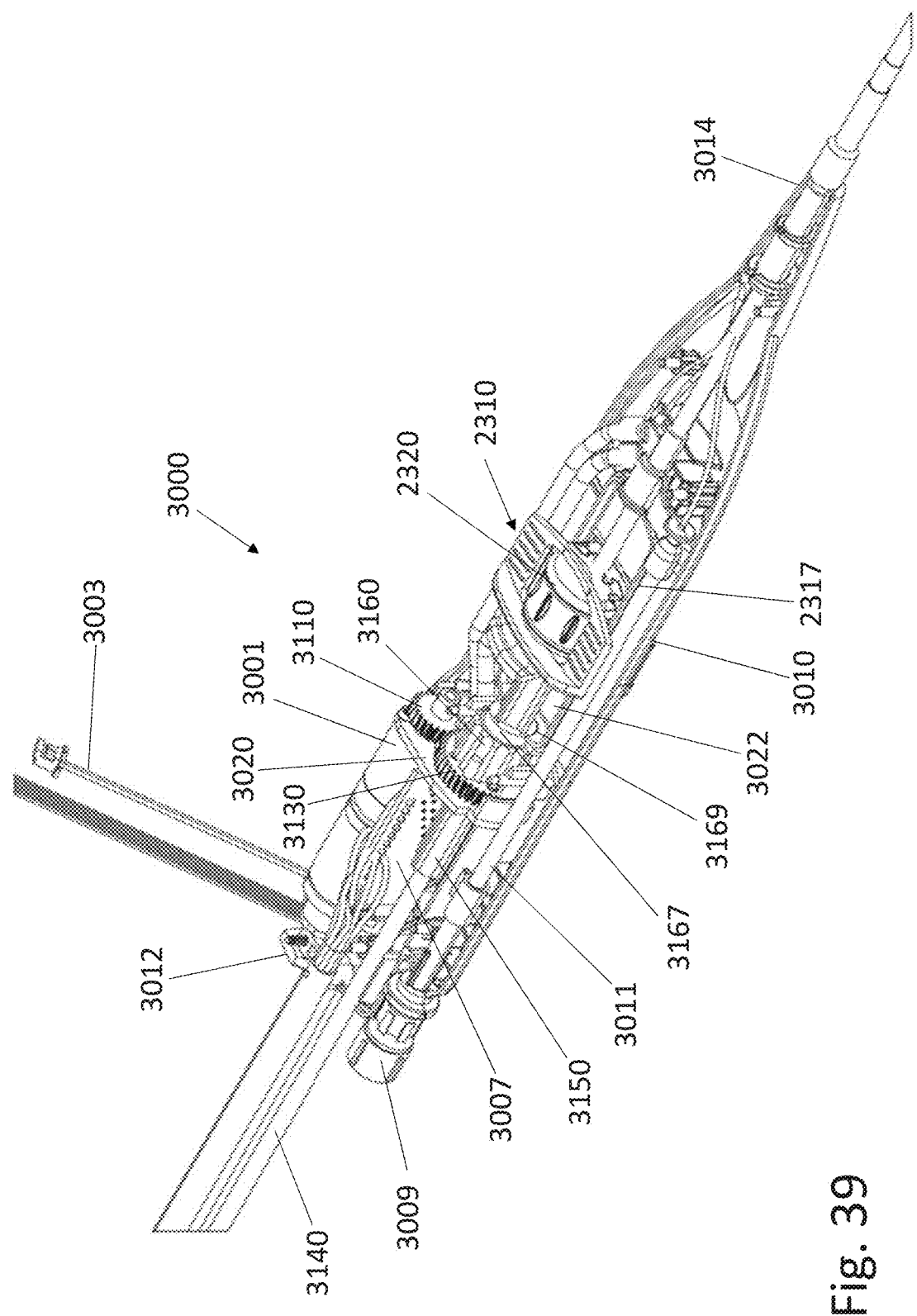
FIG. 39 is a perspective view of an ablation instrument according to another embodiment with one half of a housing being shown along with internal parts.

In general, and like the other embodiments, the cardiac ablation device 3000 is formed of a housing that contains the internal components of the device. The housing can be formed of two parts, namely, a top part and a bottom housing 3010 that is shown in FIG. 39 and designed to close off of the top part as in the other embodiment(s) described herein. The bottom housing 3010 has a proximal end 3012 and an opposing distal end 3014. Between the sides of the bottom housing 3010 there is a floor on which the internal components of the device 3000 are disposed. The bottom housing 3010 has an intermediate portion 3020 that include a slot or opening (window) 3022.

As in the previous embodiment, a top housing mates with the bottom housing 3010 to form the complete housing for the cardiac ablation device 3000 as shown in the other embodiments disclosed herein. The top housing is thus complementary to the bottom housing 3010 and a hollow space is defined therebetween in which the internal components of the device 3000 are contained. As with the bottom housing 3010, the top housing has an intermediate portion that also includes a slot or opening (window) that overlies the slot 3022 so as to form a complete through hole or window that receives and allows the user to access a controller that is disposed within this slot 3022.

The top housing and bottom housing 3010 thus can be of a clam shell type construction which the two halves close to form the complete housing. Any number of different techniques can be used to attach the top housing and the bottom housing 3010 to one another, including snap-fit, the use of fasteners, etc.

Figure 41:
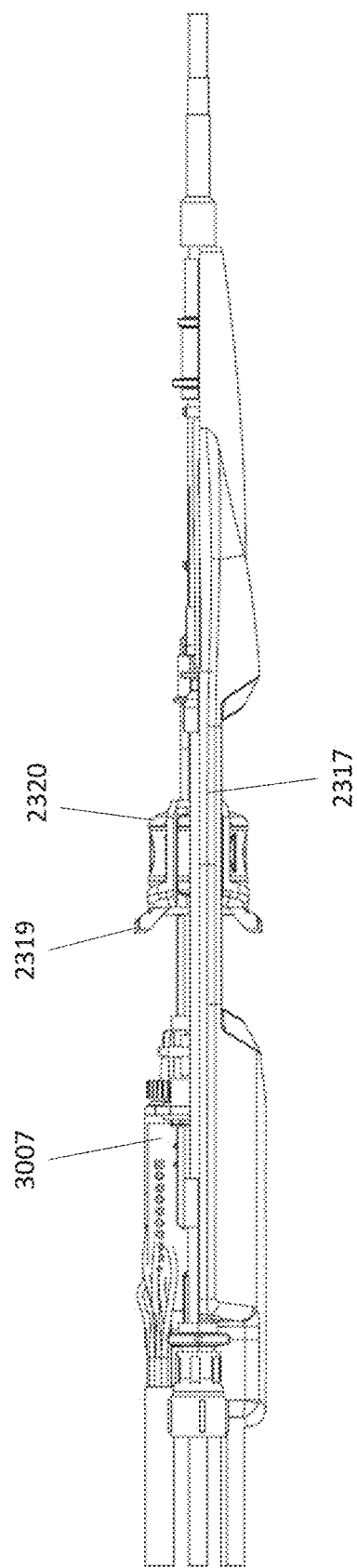
FIG. 41 is a side elevation view of the ablation instrument of FIG. 39.
Figure 42:
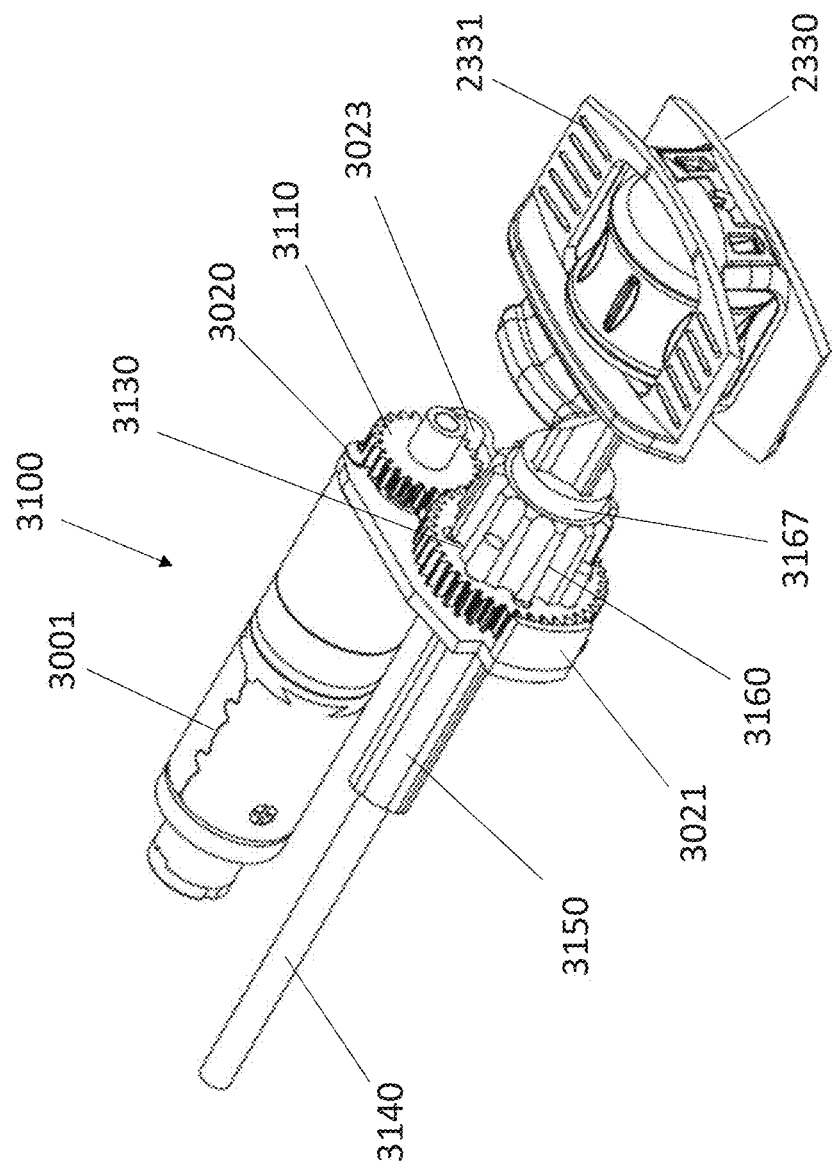
FIG. 42 is a top and side perspective view of a motor and gear subassembly of the ablation instrument of FIG. 39.
Figure 43:
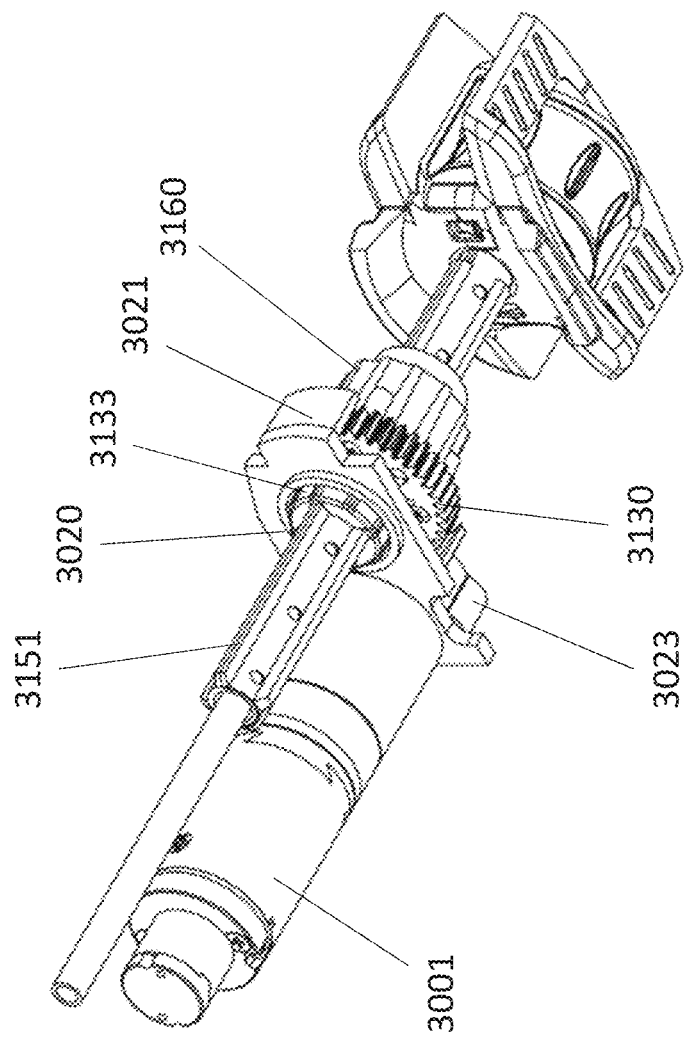
FIG. 43 is a bottom and side perspective view of the motor and gear subassembly of the ablation instrument of FIG. 39.
Figure 44:
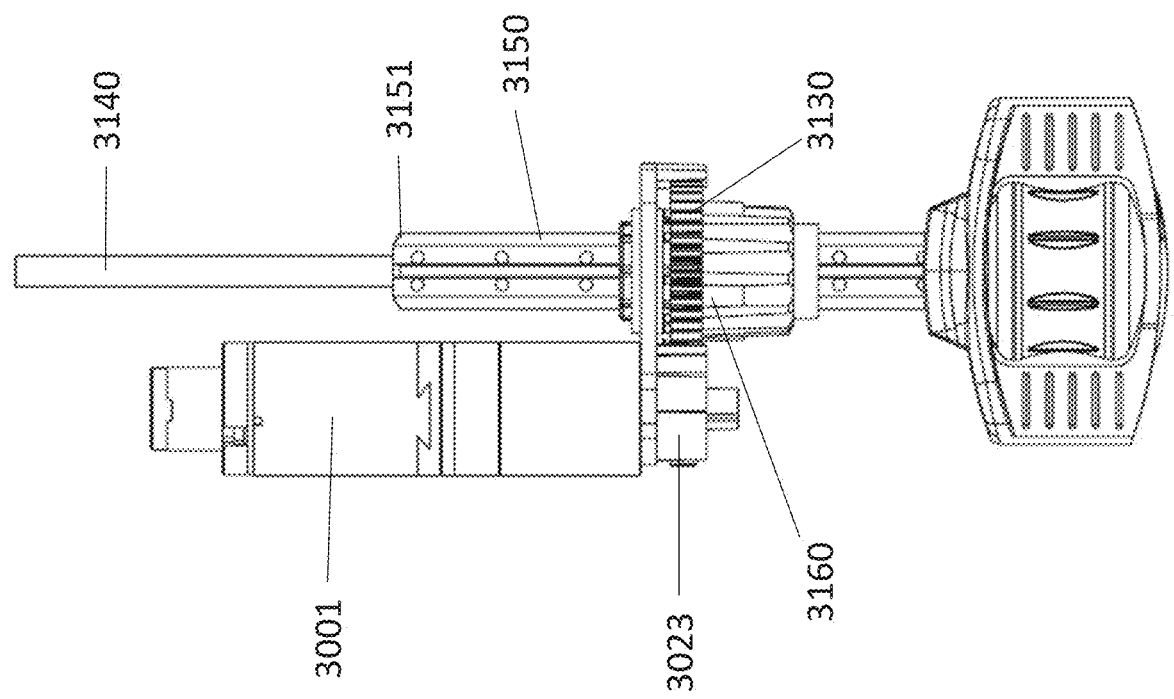
FIG. 44 is a top plan view of the motor and gear subassembly.
Figure 45:
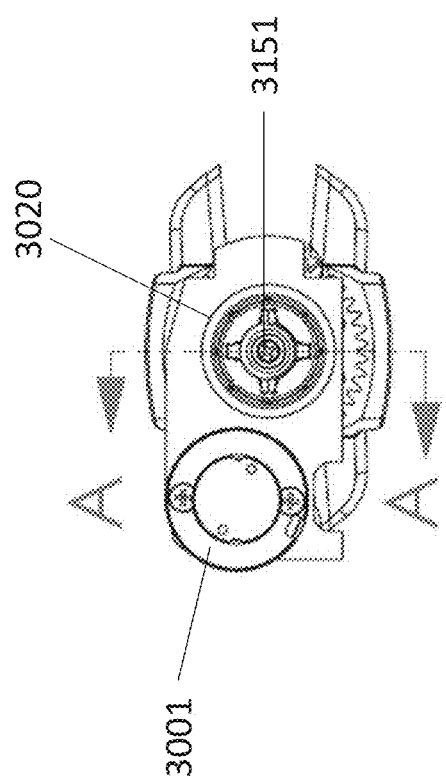
FIG. 45 is an end view of the motor and gear subassembly.
Figure 46:
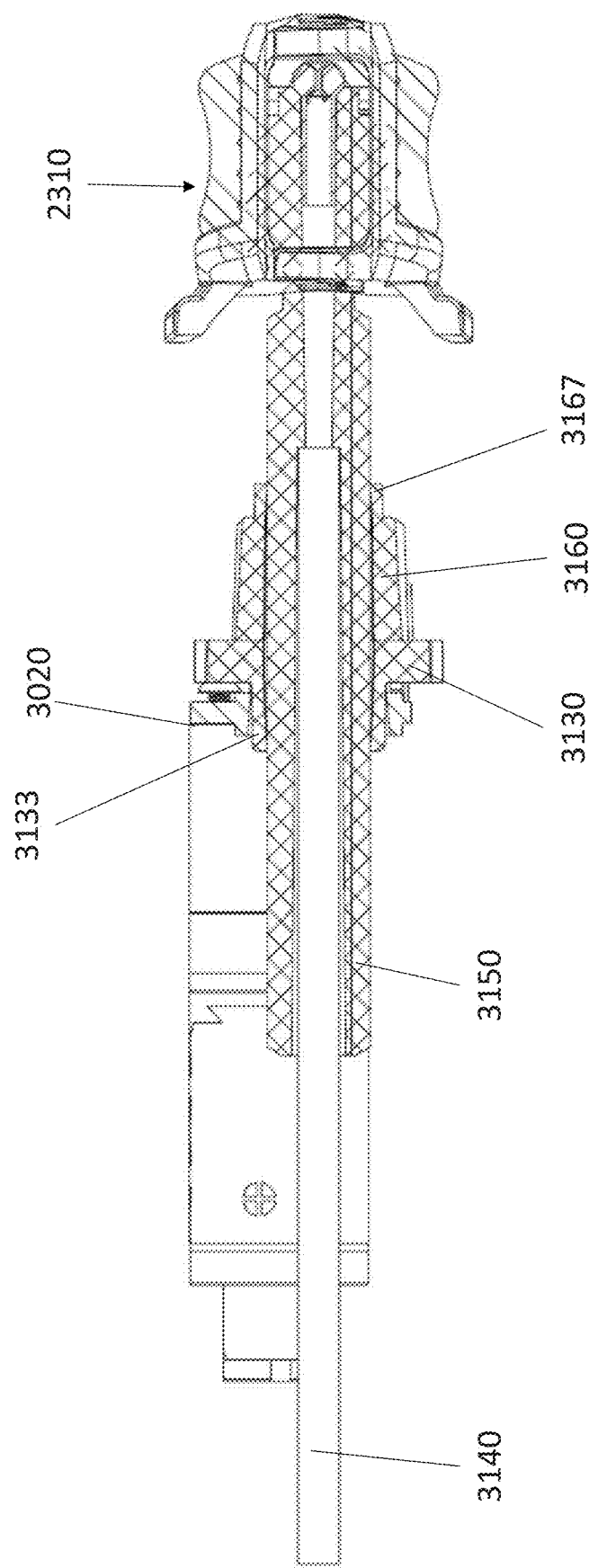
FIG. 46 is a cross-sectional view taken along the line A-A in FIG. 45.

In this embodiment, the motor 3001 is disposed internally within the housing of the device 3000. More particularly, the motor 3001 is disposed within the housing at the proximal end 3012 along one side of the housing. The motor 3001 includes connectors 3003 and the like that can be coupled to electronic equipment, such as a printed circuit board 3007 (PCB) (FIG. 41). As with the other electronic components of the device 3000, the motor 3001 is powered and in particular and as discussed previously, the device 3000 can include a power cord (power cable) that can connect to an external console and a means for powering the device 3000.

Unlike the prior embodiment in which the motor 1230 is modular and reusable, the motor 3001 is disposable along with the entire catheter body. Since the motor 3001 is disposable, the motor 3001 is fully integrated into the structure of the device 3000 and more particularly, the motor 3001 is contained in the housing and is not accessible to the user nor is intended to be removed by the user. The motor 3001 is thus fixedly located and held within the housing.

There is also an imaging connector 3009 that is disposed also at the proximal end 3012 and allows for imaging equipment, such as an endoscope, to be received within the device 3000. When the endoscope is in the form of a fiber (e.g., fiber optic), it is received and passes through the connector 3009 and can be routed within a protective sheath as shown in FIG. 39. As described herein, the endoscope is ultimately routed internally within the balloon of the catheter.

As with the previous embodiment, the device 3000 includes the sliding part (a slider) 2310 that surrounds a rotating knob 2320 that is similar or identical to the rotating knobs disclosed herein and that are part of the material incorporated by reference herein. As shown, the rotating knob 2320 is contained and moves axially and rotationally within a window that is formed in the catheter handle. The rotating knob 2320 is coupled to the delivery fiber or outer sheath thereof so that movement of the rotating knob 2320 is directly translated into movement of the delivery fiber (in both a longitudinal (axial) direction and rotational direction). The rotating knob 2320 thus surrounds the delivery fiber and can be a generally cylindrical shaped part that includes surface features, such as ribs or the like, that can be gripped by the user.

The sliding part 2310 is configured such that the rotational movement (motion) of the rotating knob 2320 is not impeded by the surrounding sliding part 2310. The sliding part 2310 is constructed such that it can be easily contacted by the user to axially (longitudinally) advance the rotating knob 2320 and thus, the axially move the delivery fiber (energy emitter or ablation element or ablation emitter).

As illustrated, the sliding part 2310 is contained within the window of the catheter handle such that the two ends of the window define the ends of travel of the sliding part 2310 as described previously. It will be appreciated that the ends of the window likewise define the ends of travel of the rotating knob 2320 and thus, define the degree of longitudinal (axial) movement of the energy emitter (lesion generator).

As described previously with reference to FIG. 38, the sliding part 2310 can be formed as two parts (symmetric parts) that mate together to form a shell that surrounds the rotating knob 2320 and contains aligned holes that permit the delivery fiber contained with sheath 3015 to passes therethrough (the sliding part 2310 thus slides along the delivery fiber/sheath 3015). The window is in part defined by a pair of side rails 2317 that extend longitudinally and are located opposite one another. The sliding part 2310 is configured such that it is coupled to the side rails 2317 and in particular, the sliding part 2310 slides longitudinally along the side rails 2317. The side rails 2317 thus act as guide rails for the sliding part 2310.

In addition, each of the parts 2330, 2331 has a center portion 2337 that sits within the window and moves axially therein. The outwardly flared sides of each part 2330, 2331 prevent the assembled slider 2310 from falling out of the window since they are enlarged and extend beyond the window edges. Parts 2330, 2331 can be assembled by a snap-fit as by providing snap-fit features in the center portions 2337.

The sliding part 2310 includes ribs 2315 that project outward on each side of the sliding part 2310 allow the user to firmly grip the sliding part 2310 with the thumb and forefinger and hence control the longitudinal motion of the sliding part 2310 and also the longitudinal motion of the rotating knob 2320 which the sliding part 2310 surrounds. In this manner, the user can precisely control the longitudinal position of the rotating knob 2320 attached to the lesion generator without impeding the rotation motion when the rotational motion is being controlled by the motor. As discussed herein, the motor can be utilized to controllably rotate the rotating knob 2320 in order to controllably rotate the delivery fiber.

As illustrated, the sliding part 2310 can thus be constructed such that there is a center opening through which the rotating knob 2320 is visible and could be contacted. In particular, in the illustrated embodiment in which the sliding part 2310 is formed as a shell defined by two housing parts that mate together to form the shell, each housing part includes a center opening such that the rotating knob is accessible along each side of the handle body. Ribs 2315 can be provided on each housing part. As in the previous embodiment, the sliding part 2310 slides along the rails 2317. The side ribs 2315 thus provide a means by which the sliding part 2310 is coupled to the side rails 2317 to allow longitudinal (axial) movement of the sliding part 2310 within the window.

The sliding part 2310 can be formed such that it has a distal end portion that is located distal to the rotating knob 2320 and a proximal end portion that is located proximal to the rotating knob 2320. The sliding part 2310 can thus be in the form of a hollow shell that surrounds the rotating knob 2320 but is not directly fixed to the rotating knob 2320. Instead, the sliding part 2310 is meant to urge the rotating knob 2320 in either a forward or rearward direction within the window. The sliding part 2310 moves independent from the rotating knob 2320 and is limited to sliding along the side rails 2317 and cannot rotate. In contrast, the rotating knob 2320 is not attached to the sliding part 2310 and thus can independent move axially and rotationally. Since the rotating knob 2320 is contained (nested) within the center opening of the sliding part 2310, longitudinal movement of the sliding part 2310 is translated into longitudinal movement of the rotating knob 2320 since the sliding part 2310 urges (contacts) the rotating knob 2320 in the longitudinal direction. The urging of the rotating knob 2320 does not prevent rotation of the rotating knob 2320 since the rotating knob 2320 can freely rotate in the center opening of the assembled slider and the slider 2310 surrounds the knob but is not fixedly attached thereto and thus, when the slider slides along the catheter housing, it contacts and urges the knob 2340 in an axial (longitudinal) direction (however, the knob 2320 can continue to rotate within the window of the slider).

As shown in FIG. 38, the sliding part 2310 also includes a rear rib 2319 that is formed at one end, namely, the proximal end of the sliding part 2310. Similar to the side ribs 2315, the rear rib 2319 can be formed as part of each of the two housing parts that assembled together form the sliding part 2310. A portion of the rear rib 2319 can be disposed at a right angle to the slide ribs 2315 and at least a portion of the rear rib 2319 projects rearwardly so as to be easily accessible to the user. More specifically, the user can grasp one or both of the side ribs 2315 and rear rib 2319 for urging (sliding) the sliding part 2310 in order to translate the rotating knob 2320 in the longitudinal direction due to the rotating knob 2320 being nested within the sliding part 2310.

FIGS. 42-47 illustrate a motor and gear subassembly 3100 that includes the motor 3001 and is intended to be inserted and contained within the handle housing. The motor 3001 includes a drive shaft 3003 (FIG. 47) to which a first gear 3110 is coupled. The first gear 3110 is thus a driven gear that is driven by the action of the motor 3001 and thus can be rotated in a first direction due to rotation of the drive shaft 3003 in the first direction and can be rotated in the opposite second direction due to rotation of the drive shaft 3003 in the opposite second direction.

The subassembly 3100 includes a first support 3020 that can be in the form of a plate that is coupled to and secured to the housing of the device 3000. As shown, the motor 3001 is disposed on a proximal side of the first support 3020, while the first gear 3110 is disposed on the distal side of the first support 3020. As illustrated, the first support 3020, the first support 3020 can include a first protector (first gear guard) 3021 in the form of a curved wall that is located at one end of the first support 3020 opposite the end at which the first gear 3110 is located. The first support 3020 also includes a second protector (second gear guard) 3023 that is located at the end of the first gear 3110 and along one side of the first support 3020. The two protectors (guards) 3021, 3023 can be integrally formed with the body of the first support 3020.

It will be appreciated that the first gear 3110 is not axially movable but remains at least substantially at a fixed axial location.

The subassembly 3100 also includes a second gear 3130 that meshes with the first gear 3110 such that the driven rotation of the first gear 3110 as a result of operation of the motor 3001 is directly translated into rotation of the second gear 3130. As with the first gear 3110, the second gear 3130 is not axially movable but remains an at least substantially fixed axial location within the handle housing.

The subassembly 3100 includes a stem 3140 that can be similar to stem 1047 and can be a tubular structure. When the energy emitter that forms a part of the device 3000 is in the form of an optical fiber as described herein, the knob 2320 is attached or otherwise coupled to the optical fiber or an outer sheath or similar structure that surrounds the optical fiber which comprises the energy emitter. As shown in the figures, the knob 2320 can be attached to the stem 3140, which can have a tubular shape, such that movement of the knob 2320 is translated into movement of the stem 3140 (both in an axial direction and a rotational direction).

As discussed herein, the fiber optic (part of the energy emitter) can be surrounded by the torsionally stiff torque tube (an outer jacket or sheath) 1049 and thus, when the fiber optic is described herein, it will be appreciated that the physical fiber optic is preferably surrounded by the torque tube 1049. The fiber optic can be attached to the torque tube 1049 at its distal end (this attachment can be accomplished using traditional techniques such as bonding, etc. The stem 3140 includes a lumen through which the fiber optic and the torsionally stiff torque tube 1049 can be routed.

The stem 3140 can be formed of any number of different materials, including but not limited to metals and plastics.

A sliding splined shaft 3150 is provided and can be constructed to be coupled to the stem 3140 in a surrounding and fixed manner. The sliding splined shaft 3150 is thus fixedly attached to the stem 3140 and therefore, both of these parts move in unison is an axial direction and in response to axial movement of the knob 2320 and both move in a rotational directional as a result of rotation of the knob 2320 or by action of motor 3001 as described herein. The splined shaft 3150 includes a plurality of longitudinal splines (ribs/rails) 3151 that are spaced radially from one another. In the illustrated embodiment, there are four splines 3151 that extend longitudinally along the length (entire length) of the splined shaft 3150. The splined connection allows for axial movement but prevents rotational movement.

The splined shaft 3150 includes a connector (coupling member) 3157 formed at one end. The connector 3157 is configured to attach the knob 2330 to the splined shaft 3150. A fastener 3159 can be used to attach the knob 2320 to the splined shaft 3150.

The second gear 3130 is a toothed gear that meshes with the teeth of the first gear 3110 and also includes a hub 3133 (FIG. 46) that is integral to the second gear 3130 and extends rearwardly from the toothed portion. The hub 3133 thus extends toward the proximal end 3012 of the housing.

Figure 47:
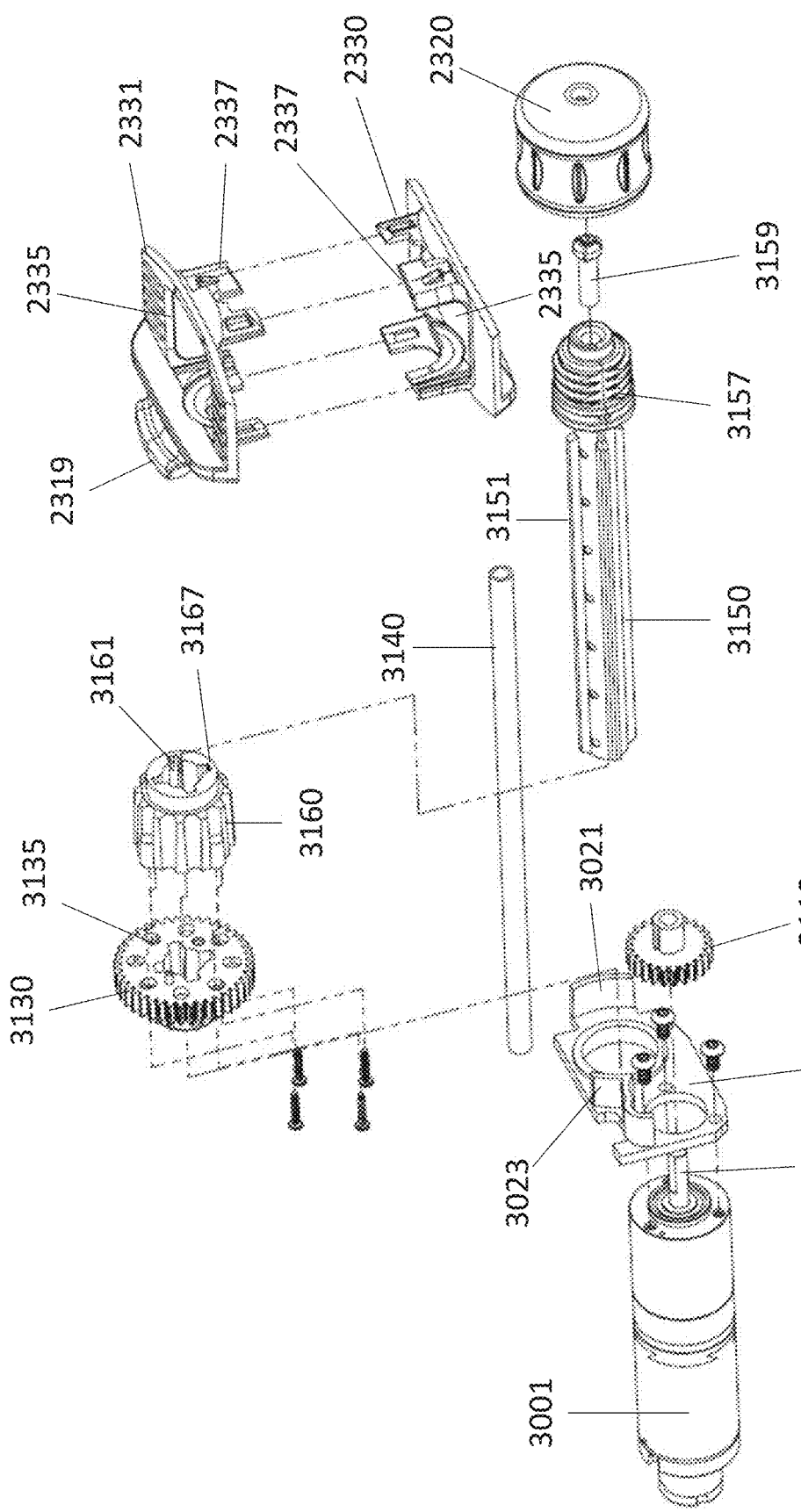
FIG. 47 is an exploded perspective view of the motor and gear subassembly.

As shown in the exploded view of FIG. 47, a contoured bore (keyed through hole) 3135 is formed centrally through the second gear 3130 and the hub 3133 and includes a plurality of recessed channels that extend axially (longitudinally along the length of the second gear). The contoured bore 3135 is complementary to the splined shaft 3150 such that the splined shaft 3150 can move axially relative to the second gear 3130 and in particular, the splined shaft 3150 axially moves within the contoured bore 3135. In the illustrated embodiment, the bore 3115 includes four indents extending radially outward from a center hole into which the four splines 3151 are received. More specifically, like the first gear 3110, the second gear 3130 is at least substantially fixed in the axial direction. As a result of the second gear 3130 being fixed in the axial direction, the splined shaft 3150 and the stem 3140 are the structures that move in the axial direction in direct response to axial movement of the knob 2320. In other words, the splined shaft 3150 is designed to slidingly travel in the axial direction within the bore 3135 to accommodate axial movement of the knob 2320.

The first protector (first gear guard) 3021 is designed to guard the second gear 3130 and is located along one side thereof.

The second protector 3023 is configured such that a first end portion covers the first gear 3110 and a second end portion also partially covers the second gear 3130. This second protector 3023 can act, as shown in FIG. 39, as a conduit (tube) guard that shields one or more conduits from the rotating first gear 3110. In FIG. 39, the conduits are shown as traveling below the second protector 3023.

A spacer 3160 is provided and comprises a hollow part that has a bore (keyed through hole) 3161 formed therethrough. The bore 3161, like the bore 3135, is contoured and configured to permit the splined shaft 3150 to slidingly travel therein in the axial direction. In the illustrated embodiment when the splined shaft consists of four splines (rails or ribs), the bore 3161 can consist of four spaced indents or slots that receive the four splines 3151 and permit axially sliding of the splined shaft 3150.

The spacer 3160 is designed to be axially fixed in place within the housing much like the second gear 3130, while the spacer 3160 freely rotates as with the second gear 3130. The spacer 3160 also has a front hub 3167 that is circular in shape. The bore 3161 also extends through the front hub 3167. As shown in the figures, the spacer 3160 is disposed adjacent the second gear 3130 on the same side of the first support 3020.

The spacer 3160 also acts as a seal element in that the spacer 3160 seals the window 3022 (FIG. 40) formed in the housing in which the knob 2320 travels. More particularly, one end (proximal end) of the window 3022 includes a slot 3169 through which the splined shaft 3150 passes. Since the window 3022 is open to environment, the slot 3169 represents an area of the device that could potentially serve as an entrance for unwanted debris or liquid which could thus come into contact with the electronics (PCB) and motor 3001. As a result, it is desirable to seal the slot 3169 as best possible. The spacer 3160 is configured to provide such sealing and in particular, the front hub 3167 is received within the slot 3169. The slot 3169 is arcuate shaped and thus, the front hub 3167 is complementary to the slot 3169 and is received and nested within the slot 3169. The front hub 3167 thus serves to effectively plug the slot 3169; however, the front hub 3167 can freely rotate within the slot 3169 since both have curved surfaces.

Figure 40:
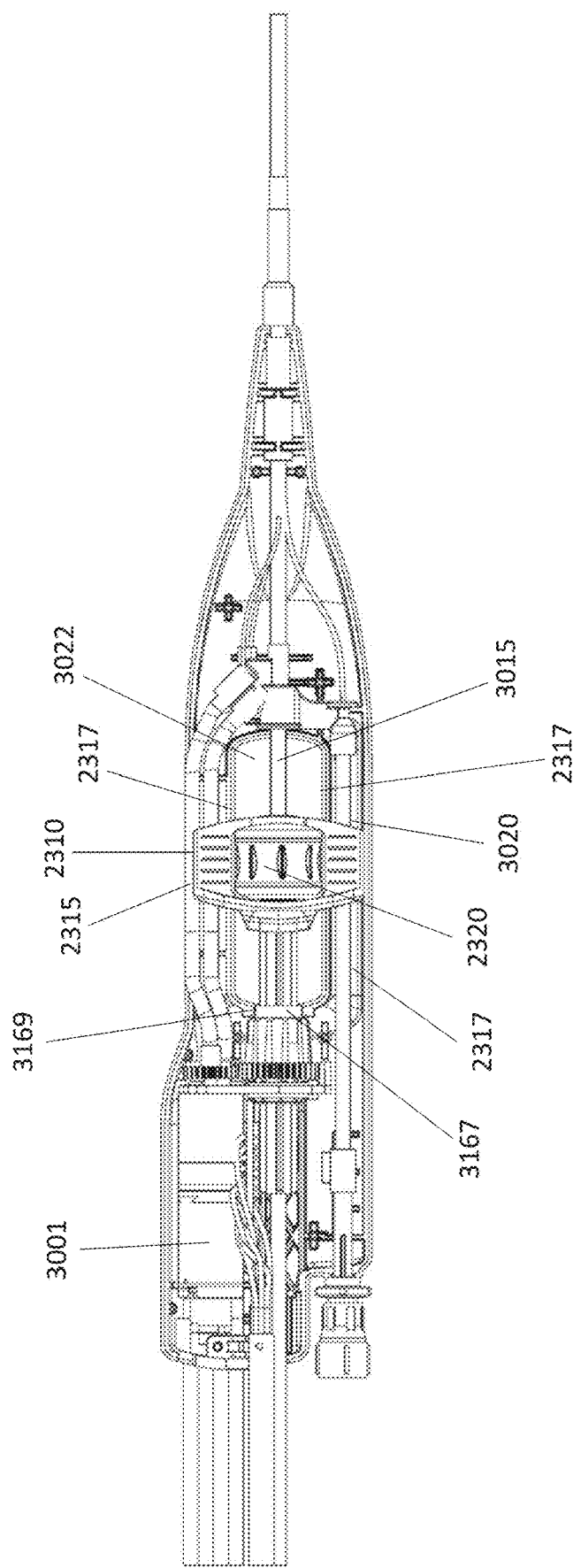
FIG. 40 is a top plan view of the ablation instrument of FIG. 39.

As shown in FIGS. 39-40, the device includes other fluid conduits that are routed adjacent to the window 3022 so as to carry fluid along a length of the device.

As discussed herein, the motor 3001, like the previously described disposable motor module, is configured to automate the rotation of the knob 2320 which directly causes a controlled rotation of the energy emitter (e.g., fiber optic fiber) that delivers the ablation energy. Axial movement of the knob 2320 and the energy emitter is performed manually in the illustrated embodiment; however, this too can be motorized to allow for a controlled axial movement.

In another mode of operation (e.g., standard operation), the knob 2320 can be manually rotated as when the motor 3001 is placed offline. It will be appreciated that since the motor 3001 is rotationally connected to the knob 2320 via the pair of gears 3110, 3130, the gearing of the motor 3001 has to be specially tailored not be too high since it must accommodate the rotation of the knob 2320 manually by the user which in turn causes the coupled splined shaft 3150 to rotate and causes the two gears 3110, 3130 to rotate as well as the drive shaft of the motor 3001 to also rotate. In other words, the user must be able to rotate the drive shaft of the motor 3001 in the standard mode of operation when the knob 2320 is manually rotated with ease and without damaging the motor 3001.

Figure 48:
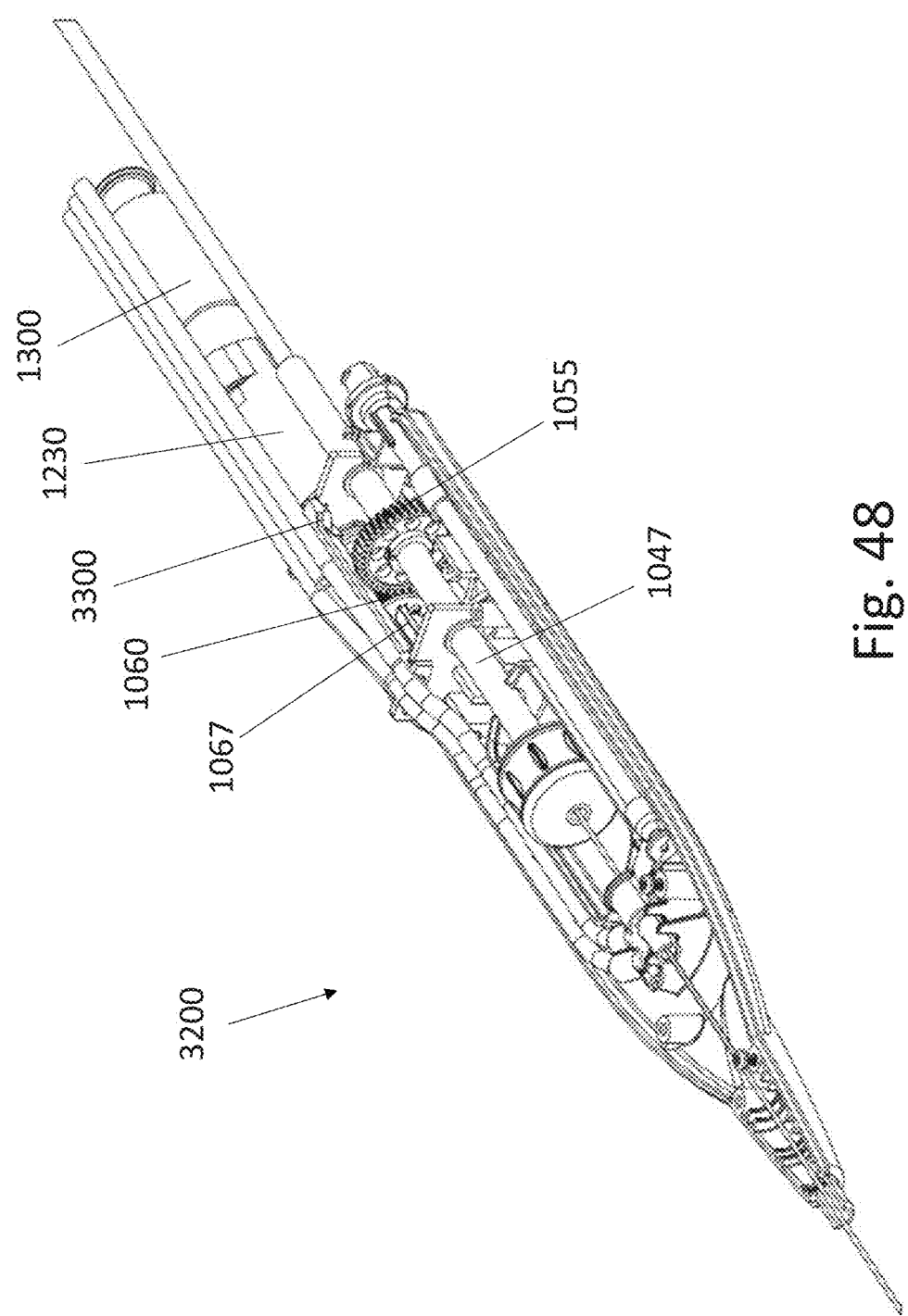
FIG. 48 is a perspective view of an ablation instrument according to another embodiment.
Figure 49:
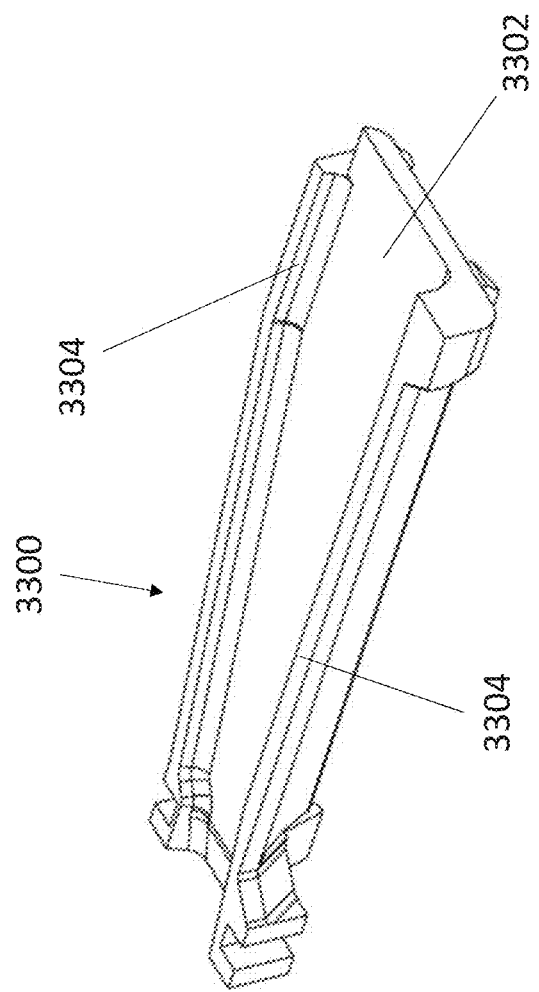
FIG. 49 is a perspective view of a tube guard used in the instrument of FIG. 48.

FIGS. 48 and 49 illustrate yet another embodiment of an ablation instrument 3200 that is similar to the instrument 1000 in that it contains a disposable motor (modular unit) contained within the tubular extension 1230. The motor 1300 includes a main drive shaft that is coupled to a splined shaft 1067. The second gear 1060 has a center through hole (keyed hole) that has recessed channels that receive the splines of the splined shaft 1067 to allow for axial movement of the second gear 1060 along the splined shaft 1067. In this embodiment, the first gear 1055 is fixedly attached to the stem (outer jacket) 1047 and remains engaged with the second gear 1060. Thus, as the stem 1047 moves axially due to movement of the knob 1045, the first gear 1055 moves axially and since it is engaged with the second gear 1060, the second gear 1060 is driven axially along the splined shaft 1067. However, rotation of the splined shaft 1067 under action of the motor causes rotation of the two meshed gears 1055, 1060 and thus rotation of the energy emitter.

FIG. 49 is a tube guard 3300 that is intended to be disposed within the instrument 3200 for routing conduits (tubes). The tube guard 3300 has a first face or surface 3302 that can be in the form of a trough due to the presence of opposing side walls 3304 that are raised relative to the first face 3302. As shown in FIG. 48, the tube guard 3300 is disposed over the second gear 1060 to allow routing of tubes over the movable second gear 1060.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An ablation instrument comprising:
an elongate catheter having a housing with an opening formed therein and being accessible along an exterior of the housing;
an energy emitter that is coupled to the elongate catheter and is configured to deliver ablative energy;
a controller that is received within the opening and is coupled to the energy emitter such that axial movement of the controller within the opening is translated to axial movement of the energy emitter and rotation of the controller within the opening is translated into rotation of the energy emitter;
a motor that is at least partially disposed within the housing of the catheter;
a first gear that is operatively connected to and driven by the motor; and
a second gear that is coupled to the energy emitter and is driven by the first gear to cause rotation of the energy emitter, while allowing the energy emitter to move axially;
wherein the energy emitter comprises a fiber optic that is at least partially contained within an elongated outer tube that surrounds a length of the fiber optic, the outer tuber being fixedly attached to the controller at a first end of the outer tube and the second gear is coupled to the outer tube such that the outer tube can slide axially through the second gear in response to axial movement of the controller within the opening;
wherein the fiber optic is fixedly attached to the controller distal to the first end of the outer tube and the fiber optic passes through and extends distal to the controller, while the outer tube terminates within the controller.

2. The ablation instrument of claim 1, wherein the first gear comprises an elongated spline gear and the second gear is fixedly attached to the outer tube and configured to move axially along the spline gear in response to axial movement of the controller within the opening.

3. The ablation instrument of claim 1, wherein the outer tube includes at least one recessed channel formed therein and the second gear includes a through hole with at least one protrusion that is disposed within the at least one channel resulting in the second gear being coupled to the outer tube such that rotation of the second gear results in rotation of the outer tube however the outer tube can move axially within the through hole of the second gear to permit axial movement of the controller, while the second gear remains at least substantially stationary in the axial direction and engages to the first gear.

4. The ablation instrument of claim 1, wherein the second gear includes a through hole with a plurality of rollers disposed within the through hole with the outer tube passing between and being in contact with the rollers resulting in the second gear being coupled to the outer tube such that rotation of the second gear results in rotation of the outer tube however the outer jacket can move axially within the through hole and between the rollers to permit axial movement of the controller, while the second gear remains at least substantially stationary in the axial direction and engaged to the first gear.

5. The ablation instrument of claim 4, wherein the outer tube has a plurality of flat portions that extend axially and on which respective rollers sit to permit the outer tube to freely slide in the axial direction relative to the second gear.

6. The ablation instrument of claim 1, wherein the motor is connected to a drive shaft that includes a plurality of longitudinally formed splines, the first gear includes a through hole with a plurality of longitudinally extended channels that receive the plurality of splines resulting in the first gear being coupled to the drive shaft in such a way that the first gear can move axially along the drive shaft in response to axial movement of the outer tube while the first gear remains engaged to the second gear such that rotation of the drive shaft is translated into rotation of the outer tube and the energy emitter.

7. The ablation instrument of claim 1, wherein the second gear and the outer tube rotate in unison; however, the outer tube is free to move axially relative to the second gear, wherein the controller rotates about a longitudinal axis of the handle.

8. The ablation instrument of claim 1, wherein the outer tube comprises a splined shaft and the second gear has a first keyed through hole formed therein that receives splines of the splined shaft such that the splined shaft can move axially relative to the second gear in response to axial movement of the controller while the second gear remains engaged to the first gear such that rotation of the drive shaft is translated into rotation of the outer tube and the energy emitter.

9. The ablation instrument of claim 8, wherein the opening has a proximal edge that has an arcuate shaped slot formed therein and a spacer element is fixedly attached to the second gear and rotates in unison with the second gear and includes a second keyed hole that receives the spines of the splined shaft to permit the splined shaft to move axially relative to the spacer element, the spacer element including a front hub that is received within the arcuate shaped slot so as to seal a proximal space of the housing in which the motor, the first gear and the second gear are located.

10. The ablation instrument of claim 9, wherein the front hub has an annular shape and the first keyed through hole and the second keyed through hole have the same shape.

11. The ablation instrument of claim 1, wherein the controller includes a knob that is fixedly coupled to the outer tube of the energy emitter and a slider that has a hole in which the knob is captured in such a way that the knob can freely rotate within the hole of the slider for rotating the energy emitter, the slider having a housing that is slidingly coupled to the exterior of the housing of the catheter such that the slider, along with the knob, slide axially with the opening of the catheter housing for axially moving the energy emitter, the slider being configured to axial contact and urge the knob to effectuate axial movement of the knob and the energy emitter does not interfere with simultaneous rotation of the knob within the hole of the slider.

12. The ablation instrument of claim 11, wherein the slider has side wings that extend beyond sides of the hole for coupling the slider to the catheter housing.

13. The ablation instrument of claim 1, wherein the motor is part of a disposable modular unit that is received within a tubular extension of the housing.

14. The ablation instrument of claim 13, wherein the motor has a main drive shaft mates with an adapter having a distal tip that is received within a socket formed at a proximal end of a secondary drive shaft to which the first gear is coupled so as to allow for free disengagement of the motor from the secondary drive shaft and removal of the disposable modular unit from the tubular extension.

15. The ablation instrument of claim 1, wherein gearing of the motor and the first gear and the second gear is selected such that manual rotation of the controller is translated through the first gear and the second gear into rotation of a drive shaft of the motor.

16. The ablation instrument of claim 15, wherein the gearing of the first gear and the second gear is such that the motor has a 1:1 gear ratio in that there is 1 motor rotation for every 1 rotation of the controller which comprises a rotatable knob.

17. The ablation instrument of claim 1, further including:
an expandable member that is attached to the catheter, the expandable member being substantially transparent to radiant ablative energy and having an elastic portion configured to conform to the shape of a target tissue region upon expansion;
wherein the energy emitter is movably disposed within a lumen of the catheter, the energy emitter being axially movable within a hollow interior of the expandable member, the energy emitter being configured to deliver an arc-shaped segment of radiant ablative energy through the expandable member to the target tissue region.

18. The ablation instrument of claim 1, wherein the fiber optic is integrally combined with a torque tube that itself is located within an outer tube and the controller comprises a rotatable knob, one end of the outer tube being attached to a connector that is disposed within and coupled to the knob, the connector having a through hole through which the fiber optic and the torque tube pass, wherein there is a collet that surrounds and pinches the torque tube for fixedly attaching the torque tube to the knob.

19. An ablation instrument comprising:
an elongate catheter having a housing with an opening formed therein and being accessible along an exterior of the housing;
an energy emitter that is coupled to the elongate catheter and is configured to deliver ablative energy;
a controller that is received within the opening and is coupled to the energy emitter such that axial movement of the controller within the opening is translated to axial movement of the energy emitter and rotation of the controller within the opening is translated into rotation of the energy emitter;
a motor that is at least partially disposed within the housing of the catheter;
a first gear that is operatively connected to and driven by the motor;
a second gear that is coupled to the energy emitter and is driven by the first gear to cause rotation of the energy emitter, while allowing the energy emitter to move axially; and
a slider formed of a first slider part slidingly disposed along a top exterior surface of the housing and a second slider part slidingly disposed along a bottom exterior surface of the housing, the first and second slider parts attaching to one another to form the assembled slider, the slider having a hole in which the controller is captured in such a way that the controller can freely rotate within the hole of the slider for rotating the energy emitter, the slider being configured such that the slider, along with the controller, slide axially with the opening of the catheter housing for axially moving the energy emitter, the slider being configured to axial contact and urge the controller to effectuate axial movement of the controller and the energy emitter does not interfere with simultaneous rotation of the controller within the hole of the slider, the first slider part having an upwardly extending rear wall that comprises a contact surface for urging the slider and the controller axially.

* * * * *